(12) United States Patent
Broadhurst et al.

(10) Patent No.: US 6,281,363 B1
(45) Date of Patent: Aug. 28, 2001

(54) CYCLIC HYDRAZINE DERIVATIVES

(75) Inventors: Michael John Broadhurst, Royston; William Henry Johnson, Bodmin; Daryl Simon Walter, Knebworth, all of (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/457,798

(22) Filed: Dec. 9, 1999

(30) Foreign Application Priority Data

Dec. 11, 1998 (GB) .................................................. 9827408
Oct. 25, 1999 (GB) .................................................. 9925211

(51) Int. Cl.$^7$ ........................ C07D 233/40; C07D 233/44
(52) U.S. Cl. .................................. 548/318.5; 548/318.1; 548/316.4; 548/300.1
(58) Field of Search ............................. 548/318.5, 316.4, 548/300.1, 318.1

(56) References Cited

U.S. PATENT DOCUMENTS

| 5,304,549 | 4/1994 | Broadhurst et al. ............... 514/80 |
| 5,399,589 | 3/1995 | Rentzea et al. ..................... 514/80 |

FOREIGN PATENT DOCUMENTS

| 198 29 229 | 1/1999 | (DE) . |
| 497 192 | 8/1992 | (EP) . |
| WO 95/33709 | 12/1995 | (WO) . |
| 9855449 | * 12/1998 | (WO) . |
| WO 99/01428 | 1/1999 | (WO) . |
| WO 99/40063 | 8/1999 | (WO) . |
| WO 00/00465 | 1/2000 | (WO) . |

OTHER PUBLICATIONS

Chemical Abstracts, vol. 104, No. 9, Abstract No. 61519p, Mar. 3, 1986.
Abstract for B2.
Coffey, R. J. et al., Nature (1987) 328, pp. 817–820.
Karashima, T. et al., Dermatol. Sci. (1996) 12, pp. 246–254.
Olanrian A. et al., Arch. Dermatol. Res. (1995) 287, pp. 231–236.
Chemical Abstr., General Substances Index, vol. 11$^{th}$ Collective, 1982–1986, p. 14, 583 CS, Compound with RN 87362–025 which is 2–(phenylsulfonyl)hydrazide.
Chernyk et al., "Biologically Active Substances in Hydrazide Derivatives of Succinic Heterylamides", Khimiko–farmatsevticheskii Zhurnal, vol. 23, No. 7, pp. 825–828.
Kratasyuk et al., "The Effect of Succinic Acid Sulfoderivatives on Bacterial Luminescence", Prikl. Biokhim. Mikrobiol., vol. 27(1): 127–133.

* cited by examiner

*Primary Examiner*—Mukund J. Shah
*Assistant Examiner*—Sudhaker B. Patel
(74) *Attorney, Agent, or Firm*—George W. Johnston; William H. Epstein

(57) ABSTRACT

Hydrazine derivatives and their pharmaceutically acceptable salts useful for the treatment of inflammatory and autoimmune diseases, osteoarthritis, respiratory diseases, tumors, cachexia, cardiovascular disease, fever, hemorrhage, and sepsis.

16 Claims, No Drawings

CYCLIC HYDRAZINE DERIVATIVES

BACKGROUND OF THE INVENTION

Release of such cytokines as tumor necrosis factor α (TNF-α) and transforming growth factor α (TNF-α) can cause adverse reactions ranging from psoriasis to sepsis. Many of these reactions are related to inflammanation or autoimmune conditions, such as psoriasis and arthritis.

Hydroxamic acid derivatives are known to have some inhibitory effect against certain cytokines, however they also inhibit matrix metalloproteinase enzymes (MMPs) such as collagenases, stromelysins, and gelatinases, leading to undesirable side effects. Thus it is desirable to find compounds capable of inhibiting TNF-α and TGF-α which do not have these side effects. In contrast to structurally related hydroxamic acid derivatives, the hydrazine derivatives provided by the present invention show only weak inhibitory activity against the matrix metalloproteinase (MMP) family of enzymes, such as collagenases, stromelysins and gelatinases.

SUMMARY OF THE INVENTION

1. This invention provides a hydrazine derivative, being a compound of the formula

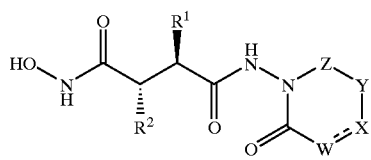

(I)

wherein

W is O, S, CO, $NR^5$, $(CR^3R^4)_m$, or $CR^{11}$;
X is CO, $NR^6$, $(CH_2)_n$, $CR^{12}$ or $CHR^{13}$;
Y is CO, $NR^7$, $(CH_2)_p$, or $CHR^{14}$;
Z is CO, CS, $SO_2$, or $CH_2$;
m is 0 or 1;
n and p are each independently 0, 1 or 2;
$R^1$ is unsubstituted lower alkyl, unsubstituted lower alkenyl, unsubstituted lower cycloalkyl, unsubstituted lower cycloalkyl-lower alkyl, unsubstituted or substituted aryl, or aryl-lower alkyl in which the aryl is unsubstituted or substituted and the lower alkyl is unsubstituted;
$R^2$ is unsubstituted lower alkyl, unsubstituted lower alkenyl, unsubstituted lower cycloalkyl, unsubstituted lower cycloalkyl-lower alkyl, —V-aryl in which the aryl is unsubstituted or substituted, —V-heterocyclyl in which the heterocyclyl is unsubstituted or substituted, or —$(CH_2)_q$—CH=$CR^8R^9$;
$R^3$, $R^4$, $R^5$, $R^6$ and $R^7$ are each independently hydrogen, unsubstituted or substituted lower alkyl, lower alkenyl, lower cycloalkyl, lower cycloalkyl-lower alkyl in which the lower alkyl is unsubstituted and the cycloalkyl is unsubstituted, unsubstituted or substituted aryl, aryl-lower alkyl in which the aryl is unsubstituted or substituted and the lower alkyl is unsubstituted, unsubstituted or substituted heterocyclyl or heterocyclyl-lower alkyl in which the the heterocyclyl is unsubstituted or substituted and the lower alkyl is unsubstituted; or $R^3$ and $R^4$ together with the carbon atom to which they are attached form a saturated carbocyclic ring having from 3 to 8 ring atoms in which zero or one ring atom is a heteroatom selected from the groups consisting of N, O and S wherein the ring nitrogen is unsubstituted or substituted; or $R^5$ and $R^6$ or $R^5$ and $R^7$ together with the nitrogen atoms to which they are attached form a saturated carbocyclic ring having from 3 to 8 ring atoms; or $R^{11}$ and $R^{12}$ together with the sp$^2$ carbon atoms to which they are attached form a fused unsubstituted lower cycloalkenyl, unsubstituted or substituted aryl or unsubstituted or substituted heteroaryl ring; or $R^5$ with either $R^{13}$ or $R^{14}$ together are lower alkylene in which zero or one $CH_2$ of the lower alkylene is replaced by a heteroatom selected from the group consisting of N, O and S wherein the N is unsubstituted or substituted; or either $R^6$ or $R^7$ with either $R^3$ or $R^4$ together are lower alkylene in which zero or one $CH_2$ of the lower alkylene is replaced by a heteroatom selected from the group consisting of N, O and S wherein the N is unsubstituted or substituted;

V is —$(CH_2)_r$—U—$(CH_2)_s$— in which r and s are each independently 0, 1, 2 or 3 and wherein U is absent or is —CH=CH—, —C≡C—, —S—, —O—, —NH—, —NHCO—, —CONH—, —$SO_2$—, —$NHSO_2$—, —$SO_2NH$—, —NHCONH— or —$NHSO_2NH$—;

$R^8$ and $R^9$ together are lower alkylene in which zero or one $CH_2$ of the lower alkylene is replaced by a heteroatom selected from the group consisting of N,O and S wherein the N is unsubstituted or substituted; and q is 1 or 2;

wherein (i) at least one of W, X and Y is one of the heteroatoms previously indicated for these substituents or CO, (ii) if W is O, Z must be CO or $SO_2$ or CS; (iii) W, X, Y and Z are not all CO; (iv) W, X and Y are not all $NR^5$, $NR^6$ and $NR^7$, respectively; and (v) when either W is $CR^{11}$, X is $CR^{12}$, or the bond between W and X is a double bond or an aromatic bond, then W is $CR^{11}$, X is $CR^{12}$ and the bond between W and X is a double bond or an aromatic bond;

or a mixture containing the compound and one or more optical isomers thereof, or a pharmaceutically acceptable salt of said compound or said mixture.

The hydrazine derivatives provided by the present invention are inhibitors of tumour necrosis factor alpha (TNF-α) release from cells. TNF-α has been associated with various cellular processes including inflammatory and cytotoxic processes. In particular TNF-α has been associated with inflammatory and autoimmune diseases (such as rheumatoid arthritis[1], inflammatory bowel disease[2], psoriasis[16,17]), osteoarthritis[5,6], respiratory diseases (such as chronic obstructive pulmonary disease[7,8] and asthma[8,9]), tumor growth and angiogenesis[10], cachexia[11,12], cardiovascular diseases (such as congestive heart failure[13,14]), dermatological diseases (such as graft-versus-host-disease[15] and), fever[18,19], haemorrhage[20,21] and sepsis[22]. Therefore the compounds of formula I are useful in treating the TNF-α dependent cellular processes associated with these diseases.

DETAILED DESCRIPTION OF THE INVENTION

2. In a more specific embodiment of the hydrazine derivative described above, the compound has the formula

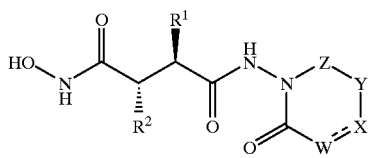

(Ia)

wherein
W is O, S, CO, $NR^5$ or $(CR^3R^4)_m$;
X is $NR^6$ or —$(CH_2)_n$—;
Y is CO, $NR^7$ or —$(CH_2)_p$—;
Z is CO, $SO_2$ or $CH_2$;
m is 0 or 1;
n and p are each independently 0, 1 or 2;
$R^1$ is unsubstituted lower alkyl, lower alkenyl, lower cycloalkyl, unsubstituted lower cycloalkyl-lower alkyl, unsubstituted or substituted aryl, or aryl-lower alkyl in which the aryl is unsubstituted or substituted and the alkyl is unsubstituted;
$R^2$ is unsubstituted lower alkyl, lower alkenyl, lower cycloalkyl, unsubstituted lower cycloalkyl-lower alkyl, —V-aryl in which the aryl is unsubstituted or substituted, —V-heterocyclyl in which the heterocyclyl is unsubstituted or substituted or —$(CH_2)_q$—CH=$CR^8R^9$;
$R^3$, $R^4$, $R^5$, $R^6$ and $R^7$ are each independently hydrogen, unsubstituted lower alkyl, lower alkenyl, lower cycloalkyl, unsubstituted lower cycloalkyl-lower alkyl, unsubstituted or substituted aryl, aryl-lower alkyl in which the aryl is unsubstituted or substituted and the alkyl is unsubstituted, unsubstituted or substituted heterocyclyl, or heterocyclyl-lower alkyl in which the heterocyclyl is unsubstituted or substituted and the lower alkyl is unsubstituted; or $R^3$ and $R^4$ together with the carbon atom to which they are attached form a saturated carbocyclic ring having from 3 to 8 ring atoms in which zero or one ring atom is a heteroatom selected from the group consisting of N, O and S wherein the ring nitrogen is unsubstituted or substituted; or $R^5$ and $R^6$ or $R^5$ and $R^7$ together with the nitrogen atoms to which they are attached form a saturated carbocyclic ring having from 3 to 8 ring atoms;
V is —$(CH_2)_r$—U—$(CH_2)_s$— in which r and s are each independently 0, 1, 2 or 3 and wherein U is absent or is —CH=CH—, —C≡C—, —S—, —O—, —NH—, —NHCO—, —CONH—, —$SO_2$—, —$NHSO_2$—, —$SO_2NH$—, —NHCONH— or —$NHSO_2NH$—;
$R^8$ and $R^9$ together are lower alkylene in which zero or one $CH_2$ is replaced by a heteroatom selected from the group consisting of N, O and S wherein the N is unsubstituted or substituted; and
q is 1 or 2;
wherein (i) at least one of W, X and Y is one of the heteroatoms previously indicated for these substituents or CO and (ii) if W is O Z must be CO or $SO_2$ and (iii) W, X and Y are not all $NR^5$, $NR^6$ and $NR^7$, respectively.

As used herein, the term "lower alkyl", alone or in combination as in "lower cycloalkyl-lower alkyl", "aryl-lower alkyl" or "heterocyclyl-lower alkyl", means a straight-chain or branched-chain alkyl group containing up to 8, preferably up to 4, carbon atoms, e.g. methyl, ethyl, n-propyl, isopropyl, n-butyl, isobutyl, sec.butyl, tert-butyl, n-pentyl and n-hexyl.

The term "optionally substituted" with reference to a lower alkyl group means an alkyl group which may be substituted by e.g. hydroxyl, amino, amino-lower alkyl, mono- or di-(lower alkyl)amino, lower alkylthio, lower alkoxycarbonyl or lower alkoxy.

The term "lower cycloalkyl", alone or in combination as in "lower cycloalkyl-lower alkyl", means a cycloalkyl group containing 3 to 7 carbon atoms, i.e. cyclopropyl, cyclobutyl, cyclopentyl, cyclohexyl and cycloheptyl. Cyclopropylmethyl, 2-cyclobutyl-ethyl and 3-cyclohexyl-propyl are examples of lower cycloalkyl-lower alkyl groups.

The term "lower alkenyl" means an alkenyl group containing from 2 to 7 carbon atoms and one double bond, e.g. allyl, vinyl and butenyl.

The term "lower cycloalkenyl" means a cycloalkenyl group containing from 4 to 8 carbon atoms and one double bond, e.g. cyclopentene, cyclohexene and cycloheptene.

The term "lower alkynyl" means an alkynyl group containing from 2 to 7 carbon atoms, e.g. propargyl or butynyl.

The term "lower alkylene" means an alkylene group containing from 2 to 6 carbon atoms, e.g. dimethylene, trimethylene, tetramethylene etc. Thus, $R^3$ and $R^4$ or $R^8$ and $R^9$ together with the carbon atom to which they are attached can represent a cyclopropane, cyclobutane, cyclopentane, cyclohexane or tetrahydropyranyl ring. Similarly, either $R^6$ or $R^7$ with either $R^3$ or $R^4$, together with the carbon and nitrogen atoms to which they are attached, can represent, for example, a pyrrolidinyl, piperidinyl, or piperazinyl ring.

The term "aryl", alone or in combination as in "aryl-lower alkyl", means phenyl or naphthyl optionally substituted by halogen, i.e. fluorine, chlorine, bromine or iodine, lower alkyl, lower alkoxy, trifluoromethyl, hydroxy, lower alkoxycarbonyl, nitro, phenyl or the like, e.g. phenyl, 1-naphthyl, 2-methylphenyl, 4-methoxyphenyl, 2,4-difluorophenyl, 4-nitrophenyl and 4-methoxycarbonylphenyl. Benzyl, 4-chlorobenzyl, 4-bromobenzyl, 3-hydroxybenzyl, 4-methoxybenzyl, 4-nitrobenzyl, 2-phenylethyl, 3,4-dimethoxy-phenethyl and the like are typical examples of aryl-lower alkyl groups.

The term "heteroaryl" means a 5- or 6-membered aromatic heterocyclic ring which contains one or more heteroatoms selected from nitrogen, sulphur and oxygen and/or a SO or $SO_2$ group and which is optionally substituted by e.g. halogen, lower alkyl, lower alkoxy and/or oxo and/or optionally benz-fused.

The term "heterocyclyl", alone or in combination as in "heterocyclyl-lower alkyl", means a 4-, 5-, 6- or 7-membered saturated or partially unsaturated or 5- or 6-membered aromatic heterocyclic ring which is bonded via a C atom or secondary N atom (i.e. —NH—), which contains one or more hetero atoms selected from nitrogen, sulphur and oxygen and/or a SO or $SO_2$ group and which is optionally substituted by e.g. halogen, lower alkyl, lower alkoxy and/or oxo and/or optionally benz-fused. Examples of such heterocyclyl groups are pyrrolidinyl, pyrrolinyl, pyrazolinyl, piperidinyl, N-methylpiperidinyl, morpholinyl, thiamorpholinyl, thiamorpholinyl S,S-dioxide, hexahydroazepinyl, tetrahydropyranyl, tetrahydrothiopyranyl, furyl, thienyl, thiazolyl, oxazolyl, isoxazolyl, oxetanyl, imidazolidinyl, dioxolanyl, pyrrolyl, pyridyl, pyrimidinyl, benzofuranyl, benzothienyl, benzthiazolyl, indolyl, isoindolyl, e.g. phthalimido, quinolyl and isoquinolyl.

The term "heteroatom" means nitrogen, sulphur or oxygen or a SO or $SO_2$ group, wherein the nitrogen is optionally substituted by e.g. lower alkyl, amido-lower alkyl, amino-lower alkyl, mono- or di-(lower alkyl)amino-lower alkyl, aryl-lower alkyl, heterocyclyl-lower alkyl, aryl, heterocyclyl, lower alkylcarbonyl, amino-lower alkylcarbonyl, aryl-lower alkylcarbonyl, arylcarbonyl, heterocyclylcarbonyl, lower alkoxycarbonyl, aryl-lower alkoxycarbonyl, aryloxycarbonyl, heterocyclyloxycarbonyl, lower alkylsulphonyl, arylsulphonyl, heterocyclylsulphonyl, or any other N-protecting group.

The symbol "CO" refers to carbonyl. The symbol "CS" refers to thiocarbonyl.

Compounds of formula (I) or (Ia) which are acidic form pharmaceutically acceptable salts with bases such as alkali metal hydroxides, e.g. sodium hydroxide and potassium hydroxide, alkaline earth metal hydroxides, e.g. calcium hydroxide, barium hydroxide and magnesium hydroxide, and the like. Those compounds of formula (I) or (Ia) which are basic can form pharmaceutically acceptable salts with inorganic acids, e.g. with hydrohalic acids such as hydrochloric acid and hydrobromic acid, sulphuric acid, nitric acid and phosphoric acid, and with organic acids, e.g. with acetic acid, tartaric acid, succinic acid, fumaric acid, maleic acid, malic acid, salicylic acid, citric acid, methanesulphonic acid and p-toluenesulphonic acid.

It will be appreciated that, although the formulae presented herein show the respective compounds in their absolute stereochemistry, the invention embraces not only the depicted stereoisomers, but also the corresponding racemates and diastereoisomeric mixtures. Further, when the spacer group denoted by V contains an olefinic double bond, as in —CH$_2$—CH=CH—, this can have the (E) or (Z) configuration, preferably the (E) configuration.

Further embodiments of compounds (I) or (Ia) according to 1., or 2., mentioned above are set forth below.

3. In compounds according to 1, the ring incorporating W, X, Y and Z preferably has one of the following formulae (a) to (u) in which $R^3$, $R^4$, $R^5$, $R^6$, $R^7$, $R^{11}$, $R^{12}$ and $R^{13}$ have the significance given earlier except that if $R^3$ or $R^4$ is hydrogen the other is not hydrogen:

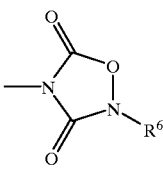 (a)

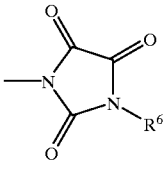 (b)

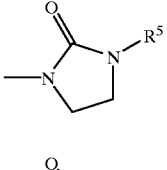 (c)

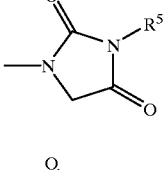 (d)

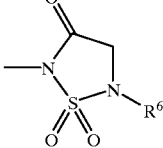 (e)

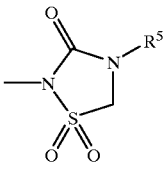 (f)

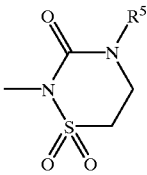 (g)

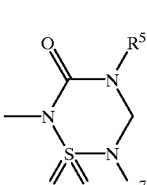 (h)

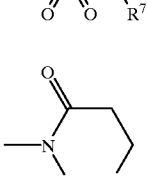 (i)

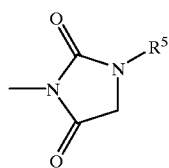 (j)

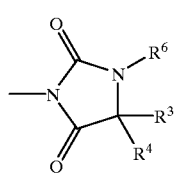 (k)

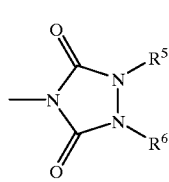 (l)

(m) 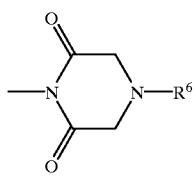

(n) 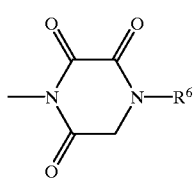

(o) 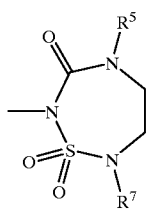

(p) 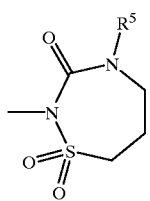

(q) 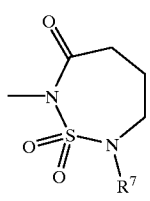

(r) 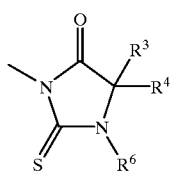

(s) 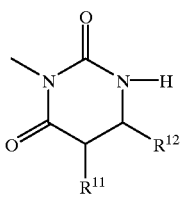

(t) 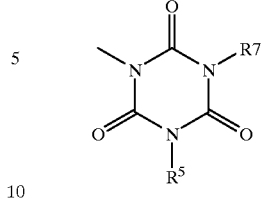

(u) 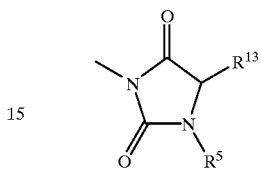

Examples of rings incorporating W, X, Y and Z of formula (s) above are:

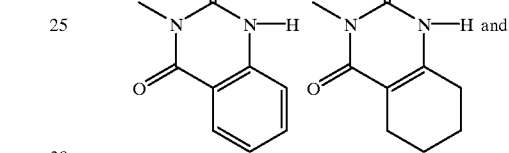

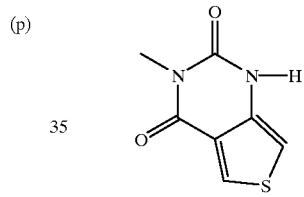

4. Preferred compounds according to 2 are those in which the ring incorporating W, X, Y and Z has formula (a) to (q) as shown above and wherein $R^3$, $R^4$, $R^5$, $R^6$ and $R^7$ have the significance given earlier.

5. Preferred compounds according to 1., or 3 are those in which the ring incorporating W, X, Y and Z has formula (a), (b), (j), (m) (r), (s) or (u) as shown hereinbefore.

6. More preferred compounds according to 1 to 5 are those in which the ring incorporating W, X, Y and Z has formula (a), (j) or (m).

7. Within embodiments 1., to 6., the spacer group denoted by V can be, for example, a group of the formula —$(CH_2)_r$—U—$(CH_2)_s$— in which r and s each independently stand for 0, 1, 2 or 3 and wherein U is absent or represents —CH=CH—, —C≡C—, —S—, —O—, —NH—, —NHCO—, —CONH—, —$SO_2$—, —$NHSO_2$—, —$SO_2NH$—, —NHCONH— or —$NHSO_2NH$—.

8. Regarding embodiments 1 to 7 those compounds of formula (I) or (Ia) are preferred in which $R^1$ represents lower alkyl, especially isobutyl.

9. Within embodiments 1 to 8 an embodiment of compounds of formula (I) or (Ia) is preferred in which $R^2$ represents lower cycloalkyl-lower alkyl, especially 3-cyclohexylpropyl, or in which $R^2$ represents a group of the formula —$(CH_2)_3$-aryl or —$CH_2$—CH=CH-aryl, especially where "aryl" represents unsubstituted phenyl, or in which $R^2$ represents phenyl benzyl.

10. More particularly the following are examples of preferred compounds of formula (I) or (Ia):

(E)-2(R)-[1(S)-(Hydroxycarbamoyl)-4-phenyl-3-butenyl]-4-methyl-N-(2,5-dioxo-1-imidazolidinyl)valeramide,
(E)-N-(hexahydro-2,6-dioxo-1-pyrimidinyl)-2(R)-[1(S)-(hydroxycarbamoyl)-4-phenyl-3-butenyl]-4-methylvaleramide,
2(R)-[4-cyclohexyl-1(S)-(hydroxycarbamoyl)butyl]-4-methyl-N-(2,5-dioxo-1-imidazolidinyl)valeramide,
(E)-N-(tetrahydro-3-oxo-2H-1,2,4-thiadiazin-2-yl)-2(R)-[1(S)-(hydroxycarbamoyl)-4-phenyl-3-butenyl]-4-methylvaleramide S,S-dioxide;
2(R)-[1(S)-(hydroxycarbamoyl)-4-phenylbutyl]-4-methyl-N-(2,6-dioxo-1-piperazinyl)valeramide,
2(R)-[1(S)-(Hydroxycarbamoyl)-4-phenylbutyl]-N-(4(S)-isopropyl-2,5-dioxo-1-imidazolidinyl)-4-methylvaleramide,
2(R)-[1(S)-(Hydroxycarbamoyl)-4-phenylbutyl]-4-methyl-N-[4(S)-(1(S)-methylpropyl)-2,5-dioxo-1-imidazolidinylvaleramide,
(E)-2(R)-[1(S)-(Hydroxycarbamoyl)-4-phenyl-3-butenyl]-N-[4(S)-(1(S)-methylpropyl)-2,5-dioxo-1-imidazolidinyl]-4-methylvaleramide,
2(R)-[1(S)-(Hydroxycarbamoyl)-4-phenylbutyl]-4-methyl-N-(2,5-dioxo-1-imidazolidinyl)valeramide, and
2(R)-[2-(4-Biphenylyl)-1(S)-(hydroxycarbamoyl)ethyl]-N-(2,5-dioxo-1-imidazolidinyl)-4-methylvaleramide.

Other preferred compounds of formula (I) are

2(R)-[1(S)-(Hydroxycarbamoyl)-4-phenylbutyl]-4-methyl-N-[4(S)-[2-(methylthio)ethyl]-2,5-dioxo-1-imidazolidinyl]valeramide,
2(R)-[1(S)-(Hydroxycarbamoyl)-4-phenylbutyl]-N-[4(S)-(hydroxymethyl)-2,5-dioxo-1-imidazolidinyl]-4-methylvaleramide,
2(R)-[1(S)-(Hydroxycarbamoyl)-4-phenylbutyl]-N-(4(S)-isopropyl-5-oxo-2-thioxo-1-imidazolidinyl)-4-methylvaleramide,
(E)-2(R)-[1(S)-(Hydroxycarbamoyl)-4-phenyl-3-butenyl]-N-[4(S)-(hydroxymethyl)-2,5-dioxo-1-imidazolidinyl]-4-methylvaleramide,
Benzyl 3-[2(R)-[1(S)-(hydroxycarbamoyl)-4-phenylbutyl]-4-methylvaleramido]-2,4-dioxo-1,3,8-triazaspiro[4,5]decane-8-carboxylate,
N-(1,2,3,4-Tetrahydro-2,4-dioxothieno[3,2-d]pyrimidin-3-yl)-2(R)-[1(S)-(hydroxycarbamoyl)-4-phenylbutyl]-4-methylvaleramide,
N-(1,2,3,4-Tetrahydro-2,4-dioxothieno[3,4-d]pyrimidin-3-yl)-2(R)-[1(S)-(hydroxycarbamoyl)-4-phenylbutyl]-4-methylvaleramide,
2(R)-[1(S)-(Hydroxycarbamoyl)-4-phenylbutyl]-N-[4(S)-methoxymethyl)-2,5-dioxo-1-imidazolidinyl]-4-methylvaleramide, and
1-(8-Acetyl-2,4-dioxo-1,3,8-triazaspiro[4.5]decan-3-yl)-2(R)-[1(S)-(hydroxycarbamoyl)-4-phenylbutyl]-4-methylvaleramide.

According to the process provided by the present invention, the novel hydrazine derivatives of embodiments 1 to 10 as set forth hereinbefore are manufactured by cleaving off the protecting group denoted by $R^{10}$ from a compound of the formula

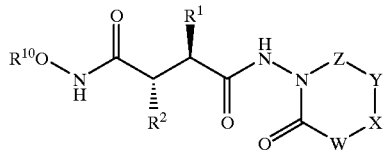

(II)

wherein $R^1$, $R^2$, W, X, Y and Z have the significance given earlier and $R^{10}$ represents a protecting group
and, if desired, converting a compound of formula (I) or (Ia) obtained into a pharmaceutically acceptable salt.

Alternatively, the novel hydrazine derivatives set forth hereinbefore, wherein W represents $NR^5$ and $R^5$ represents H, and their pharmaceutically acceptable salts, may be manufactured by cleaving off the protecting groups denoted by $R^{10}$ and P from a compound of the formula

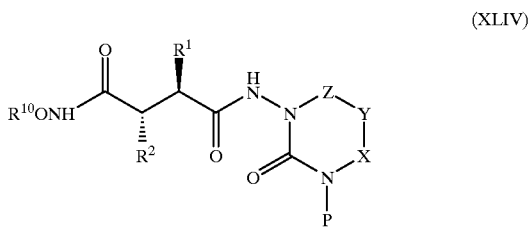

(XLIV)

wherein $R^1$, $R^2$, X, Y and Z have the significance given earlier and $R^{10}$ and P each represent a protecting group
and, if desired, converting a compound of formula (I) or (Ia) obtained into a pharmaceutically acceptable salt.

The protecting group denoted by $R^{10}$ in a compound of formula (II) or (XLIV) can be any conventional protecting group, but is preferably tetrahydropyranyl, 4-methoxybenzyl, benzyl, or tri(lower alkyl)silyl, especially tert-butyldimethylsilyl.

The cleavage of the protecting group denoted by $R^{10}$ in a compound of formula (II) or (XLIV) is carried out according to methods known per se. For example, the tetrahydropyranyl group can be cleaved off by treatment with a sulphonic acid, e.g. methanesulphonic acid or p-toluenesulphonic acid, in a lower alkanol, e.g. methanol, or by treatment with hydrogen chloride. Cleavage of the 4-methoxybenzyl group can be effected, for example, using trifluoroacetic acid. Hydrogenolysis in the presence of a catalyst, e.g. palladium, and in a lower alkanol, e.g. methanol, can be used for the cleavage of the benzyl group. A tri(lower alkyl)silyl group can be cleaved off using water or a medium having a low pH, with this cleavage normally taking place during the working up of the respective compound of formula (II) or (XLIV) from the medium in which it is prepared (i.e. the cleavage takes place in situ).

The conversion of a compound of formula (I) or (Ia) into a pharmaceutically acceptable salt is carried out by any conventional technique for forming such salts, i.e. by conventional treatment with the corresponding acid or base.

The compounds of formula (II) and (XLIV) used as starting materials in the foregoing processes are novel and form further objects of the present invention.

The compounds of formula (I) or (Ia), (II) and (XLIV) can be prepared by a variety of routes as illustrated in the Reaction Schemes A, B, C, D, E, F, G, H, I, J, K and L hereinafter.

The compounds of formula (II) in which Z represents CO or $SO_2$ may be prepared, for example, as illustrated in Reaction Scheme A in which $R^1$, $R^2$, W, X and Y have the significances given earlier, Z represents CO or $SO_2$, tBu represents tert-butyl and P indicates that any amino group present is protected by a conventional amino protecting group, e.g. benzyl, benzyloxycarbonyl, 9-fluorenylmethyloxycarbonyl, phthalimido and the like.

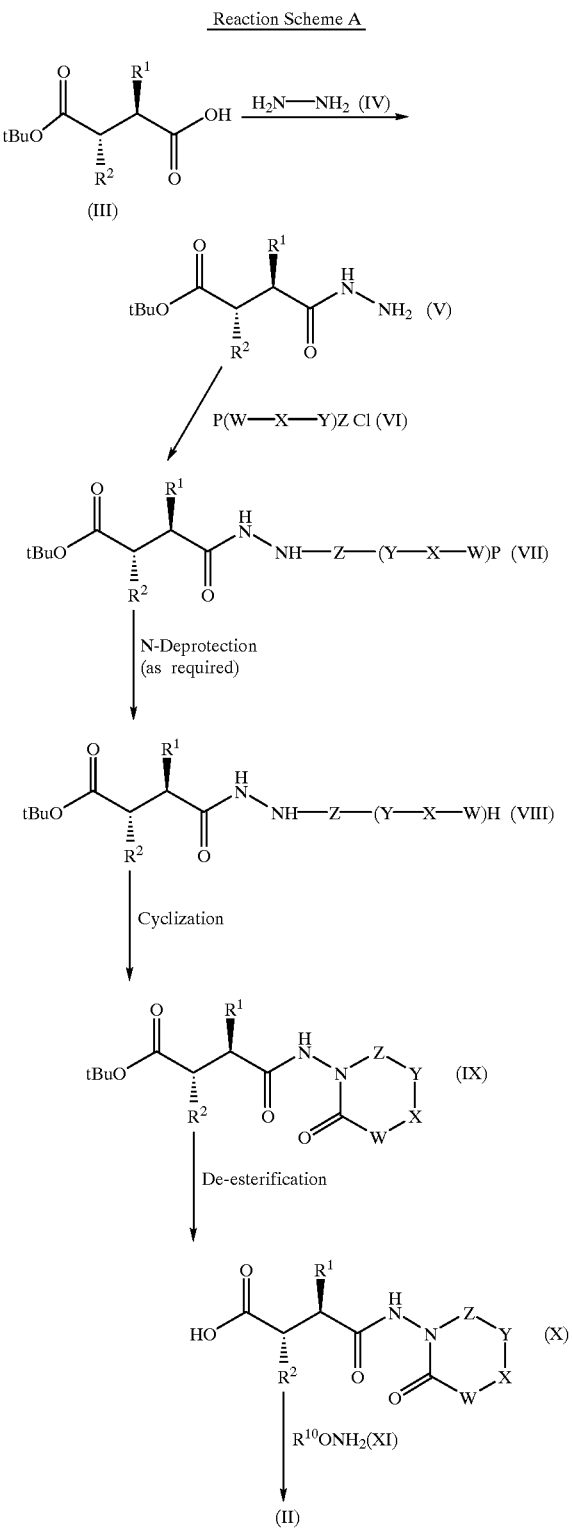

Reaction Scheme A

Having regard to Reaction Scheme A, the first step comprises the condensation of a compound of formula (III) with hydrazine of formula (IV) or an acid addition salt thereof, e.g. the hydrochloride, to give a hydrazide of formula (V). This condensation is carried out under the known conditions of a peptide coupling reaction. For example, it can be carried out according to the activated ester procedure or using the coupling reagents known per se for peptide couplings, e.g. 1-hydroxybenzotriazole in the presence of 1-ethyl-3-(3-dimethylaminopropyl) carbodiimide hydrochloride.

In the next step a compound of formula (V) is reacted with a compound of formula (VI) to give a compound of formula (VII). The reaction of a compound of formula (V) with a compound of formula (VI) is carried out in a conventional manner, suitably in an organic solvent which is inert under the reaction conditions and in the presence of an organic base at about 0° C. to about room temperature. Suitable solvents include halogenated hydrocarbons, e.g. dichloromethane. Pyridine and tri(lower alkyl)amines, e.g. triethylamine, can be mentioned as an example of suitable organic bases which can be used.

A N-deprotection of a compound of formula (VII) which may be required in the next step is also carried out in a manner known per se. For example, the benzyloxycarbonyl group can be removed by hydrogenolysis, the fluorenylmethyloxycarbonyl group can be removed by treatment with piperidine and the phthalimido group can be converted into amino by treatment with hydrazine hydrate.

A thus-obtained compound of formula (VIII) is subsequently cyclized to a compound of formula (IX). This cyclization is carried out by reaction with phosgene in the presence of a base, e.g. N-ethylmorpholine, at about 0° C. to about room temperature. Suitably, this reaction is carried out in an organic solvent which is inert under the reaction conditions, e.g. an aromatic hydrocarbon such as benzene, toluene or a xylene.

The de-esterification of a compound of formula (IX) to give a compound of formula (X) is also carried out in a known manner, conveniently by treatment with trifluoroacetic acid in an organic solvent which is inert under the reaction conditions, e.g. a halogenated hydrocarbon such as dichloromethane, at about room temperature.

In the final step of Reaction Scheme A compound of formula (X) is converted into a compound of formula (II) by condensation with an O-protected hydroxylamine of formula (XI). The condensation is carried out in a manner known per se for peptide coupling reactions and using conventional coupling reagents, e.g. 1-hydroxybenzotriazole in the presence of 1-ethyl-3-(3-dimethylaminopropyl)carbodiimide hydrochloride.

The compounds of formula (II) in which Z represents $CH_2$ can be prepared, for example, as illustrated in Reaction Scheme A, but using a compound of the formula

P(W—X—Y)CHO                            (XII)

wherein W, X, Y and P have the significance given earlier, in place of a compound of formula (VI), and subsequently reducing the reaction product with an alkali metal cyanoborohydride. The reaction of a compound of formula (V) with a compound of formula (XII) is conveniently effected in the presence of p-toluenesulphonic acid and molecular sieves. The reduction of the reaction product is advantageously carried out in a lower alkanol, e.g. methanol. Sodium cyanoborohydride is the preferred alkali metal cyanoborohydride.

The compounds of formula (II) in which Z represents CO can be prepared, for example, as illustrated in Reaction Scheme A, but using a compound of formula

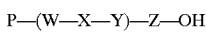     (XXX)

wherein W, X, Y and P have the significance given earlier, in place of a compound of formula (VI), performed under the known conditions of a peptide coupling reaction, as described earlier.

The compounds of formula (IX) hereinbefore in which W represents $(CR^3R^4)_m$, m stands for 1, X represents $NR^6$, Y represents $—(CH_2)_p—$ and Z represents CO can also be prepared by reacting a compound of formula (V) hereinbefore with a compound of the formula

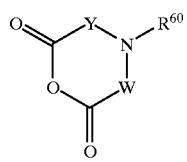     (XIII)

wherein W represents $(CR^3R^4)_m$, m stands for 1, Y represents $—(CH_2)_p—$ and $R^{60}$ has any of the values except hydrogen accorded to $R^6$ hereinbefore or represents a protecting group, conveniently in the presence of a base, e.g. pyridine or a tri(lower alkyl)amine such as triethylamine, and cyclizing the reaction product to give a compound of the formula

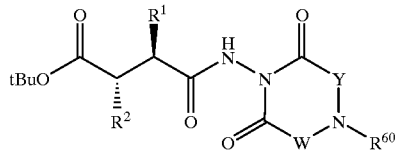     (IXa)

wherein $R^1$, $R^2$, $R^{60}$, W, Y and tBu have the significance given earlier, and cleaving off any protecting group denoted by $R^{60}$.

Furthermore, compounds of the formula

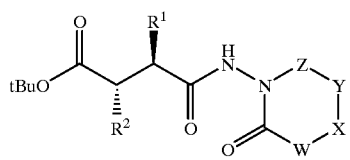     (IXb)

wherein $R^1$, $R^2$, $R^{60}$, W, X, Y, Z and tBu have the significance given earlier, can be prepared by reacting a compound of the formula

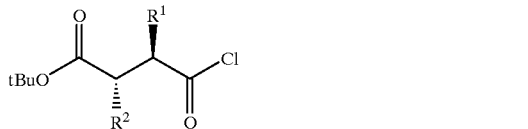     (XIV)

wherein $R^1$, $R^2$ and tBu have the significance given earlier, with a compound of the formula

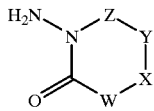     (XV)

wherein W, X, Y and Z have the significance given earlier, conveniently in the presence of a silylating agent such as trimethylsilyl chloride, a base and cupric chloride or in the presence of silver cyanide and a base in toluene at about 70° C.

The compounds of formula (IX) hereinbefore in which W represents $(CR^3R^4)_m$, m stands for 1, X represents $—(CH_2)_n—$, Y represents $NR^7$ and Z represents $SO_2$ can also be prepared by reacting a compound of formula (V) hereinbefore with a compound of the formula

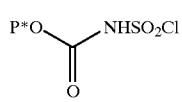     (XVI)

wherein P* represents a hydroxy protecting group, such as a group removable by hydrogenolysis, e.g. benzyl, a group removable by hydrolysis, e.g. methyl or ethyl, or a group removable by treatment with a source of fluoride, e.g. 2-(trimethylsilyl)ethyl, conveniently in the presence of a base, e.g. pyridine or a tri(lower alkyl)amine such as triethylamine, condensing the reaction product of the formula

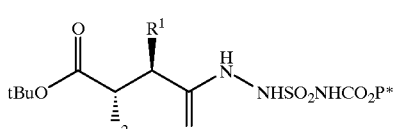     (XVII)

wherein $R^1$, $R^2$, tBuO and P* have the significance given earlier, with a compound of the formula

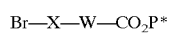     (XVIII)

wherein W and P* have the significance given earlier and X represents $—(CH_2)_n$, suitably in the presence of a base, deprotecting the resulting compound of the formula

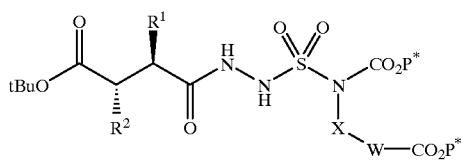

(XIX)

wherein $R^1$, $R^2$, W, X, P* and tBu have the significance given earlier, e.g. by hydrogenolysis, and cyclizing the resulting compound of the formula

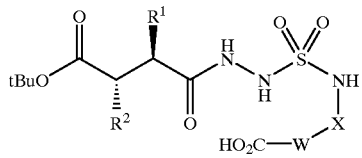

(XX)

wherein $R^1$, $R^2$, W, X and tBu have the significance given earlier, especially via activation of the carboxy group, e.g. as the acid chloride or a mixed anhydride or activated ester, to give a compound of the formula

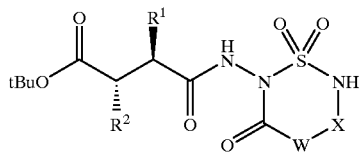

(IXc)

wherein $R^1$, $R^2$, W, X and tBu have the significance given earlier, which, if desired, can be reacted with a compound of the formula

  (XXI)

wherein $R^{71}$ has any of the values except hydrogen accorded to $R^7$ hereinbefore,
conveniently in the presence of a base such as an alkali metal carbonate, e.g. potassium carbonate, to give a compound of the formula

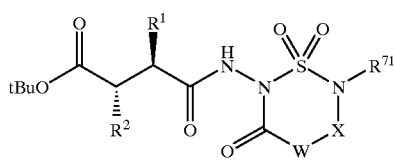

(IXd)

wherein $R^1$, $R^2$, W, X, $R^{71}$ and tBu have the significances given earlier.

The compounds of formula (IX) hereinbefore in which W represents NH, X represents —$(CH_2)_n$—, Y represents $NR^7$ and Z represents $SO_2$ can also be prepared by reacting a compound of formula (XVII) hereinbefore with a compound of the formula

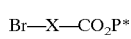  (XXII)

wherein X and P* have the significance given earlier, conveniently in the presence of a base, and deprotecting the resulting compound, e.g. by hydrogenolysis, converting the resulting compound of the formula

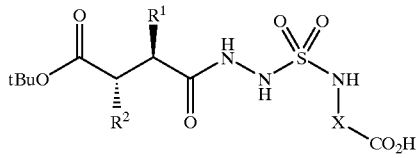

(XXIII)

wherein $R^1$, $R^2$, X and tBu have the significance given earlier, into a compound of the formula

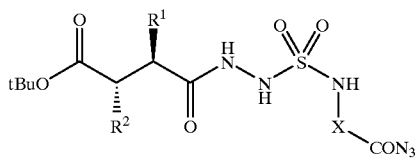

(XXIV)

wherein $R^1$, $R^2$, X and tBu have the significance given earlier, conveniently by activation of the carboxy group, e.g. as the acid chloride, an acid anhydride or an activated ester, and reaction with sodium azide or diphenylphosphoryl azide, and heating the compound of formula (XXIV) to give a compound of the formula

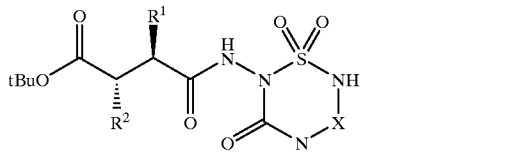

(IXe)

wherein $R^1$, $R^2$, X and tBu have the significance given earlier, which, if desired, can be N-substituted by reaction with a compound of formula (XXI) as described hereinbefore.

A further method for the preparation of compounds of formula (IX) in which W represents $(CR^3R^4)_m$, m stands for 1, X represents —$(CH_2)_n$—, Y represents $NR^7$ and Z represents $SO_2$ comprises reacting a compound of formula (V) hereinbefore with a compound of the formula

  (XXV)

wherein W, X, Y and P* have the significance given earlier, conveniently in the presence of a base such as pyridine or a tri(lower alkyl)amine, e.g. triethylamine, deprotecting the resulting compound of the formula

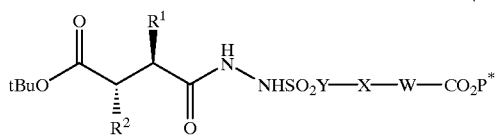
(XXVI)

wherein $R^1$, $R^2$, W, X, Y, P* and tBu have the significance given earlier, e.g. by hydrogenolysis, and cyclizing the resulting compound of the formula

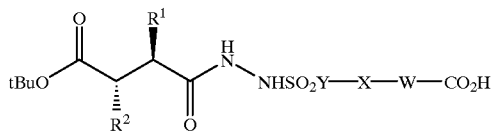
(XXVII)

wherein $R^1$, $R^2$, W, X, Y and tBu have the significance given earlier, conveniently via activation of the carboxy group, e.g. as the acid chloride, a mixed anhydride or an active ester, to give a compound of the formula

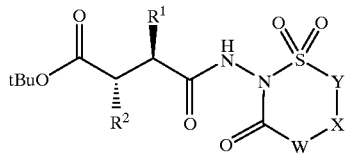
(IXf)

wherein $R^1$, $R^2$, W, X, Y and tBu have the significance given earlier.

A compound of formula (IX) in which W represents NH, X represents —$(CH_2)_n$—, Y represents —$(CH_2)_p$— and Z represents $SO_2$ can also be prepared by converting a compound of the formula

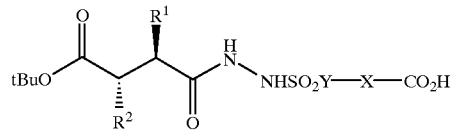
(XXVIII)

wherein $R^1$, $R^2$, X, Y and tBu have the significance given earlier, into a compound of the formula

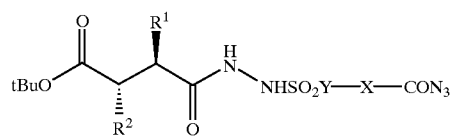
(XXIX)

wherein $R^1$, $R^2$, X, Y and tBu have the significance given earlier, conveniently by activation of the carboxy group, e.g. as the acid chloride, an acid anhydride or an activated ester, and reaction with sodium azide or diphenylphosphoryl azide, and heating the compound of formula (XXIX) to give a compound of the formula

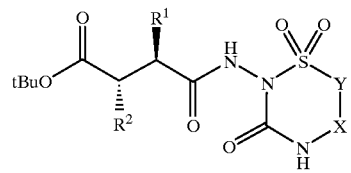
(IXg)

wherein $R^1$, $R^2$, X, Y and tBu have the significance given earlier.

Reaction Scheme B

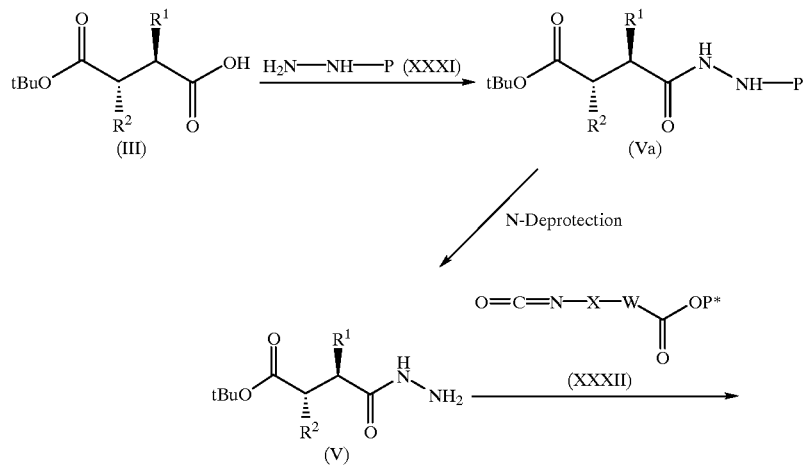

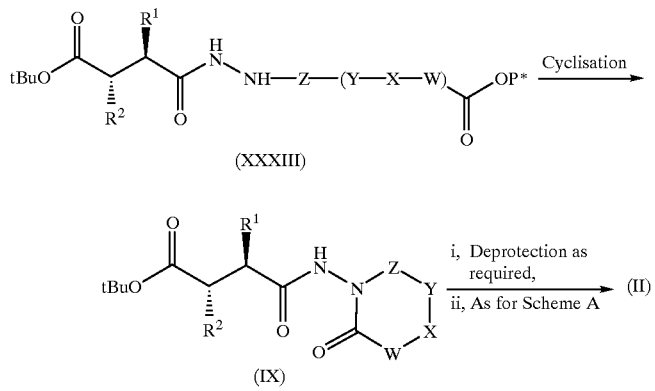

(XXXIII)

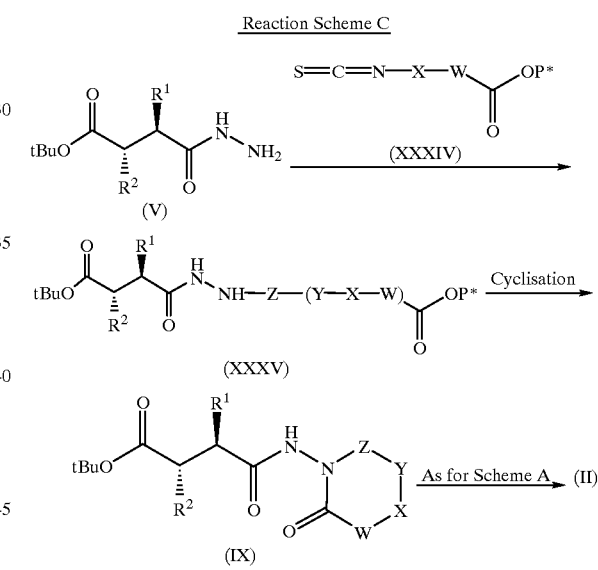

Referring to Reaction Scheme B, a number of compounds of formula (II) may be prepared in which Z represents CO; Y represents $NR^7$, where $R^7$ is H; $R^1$, tBu and P* have the significance given earlier; $R^2$ has the significance given earlier and may contain a group susceptible to attack by hydrazine, e.g. an amide; and either W represents $CR^{11}$ and X represents $CR^{12}$, where $R^{11}$ and $R^{12}$ together with the $sp^2$ carbon atoms to which they are attached form a fused lower cycloalkenyl, aryl or heteroaryl ring; or W represents $(CR^3R^4)_m$, where m stands for 1, $R^3$ and $R^4$ have the significance given earlier; and X represents $(CH_2)_n$, where n stands for 0.

A compound of formula (V) may be prepared in a manner similar to that shown earlier in Reaction Scheme A, or, alternatively, may be obtained by reacting a compound of formula (III) with a substituted hydrazine of formula (XXXI). This condensation is carried out under the known conditions of a peptide coupling reaction, as mentioned above. If required, N-deprotection of a compound of formula (Va) to give a compound of formula (V) may then be carried out in a known manner as described earlier, e.g. the benzyloxycarbonyl group can be removed by hydrogenolysis.

A compound of formula (V) is reacted with an isocyanate compound of formula (XXXII) to give a compound of formula (XXXIII). This reaction is carried out in a conventional manner, suitably in an organic solvent which is inert under the reaction conditions, and in the presence of an organic base, at about room temperature. Suitable solvents include dimethylformamide, or an aromatic hydrocarbon, e.g. toluene, or a halogenated hydrocarbon, e.g. dichloromethane; or mixtures thereof. Examples of suitable bases include triethylamine, pyridine, 2,6-lutidine, and N-ethyl morpholine. Pyridine may also be used as solvent.

Cyclisation of a compound of formula (XXXIII) to give a compound of formula (IX) may then be performed. This cyclisation may occur spontaneously on work-up of the compound of formula (XXXIII), or may be effected by heating a solution of a compound of formula (XXXIII) in an organic solvent, in the presence of an organic base, at an elevated temperature. Suitably, this reaction is carried out in an organic solvent which is inert under the reaction conditions, e.g. an aromatic hydrocarbon such as benzene, toluene or xylene. Examples of suitable organic bases are triethylamine and tetramethylguanidine.

Protecting groups which may be present in $R^1$ or $R^2$ may then be removed in a conventional manner, as described earlier, followed by the conversion of a compound of formula (IX) to a compound of formula (II), which may be performed in a manner analogous to that described earlier in Reaction Scheme A.

Reaction Scheme C

Referring to Reaction Scheme C, a number of compounds of formula (II) may be prepared where Z represents CS; W represents $(CR^3R^4)_m$, where m stands for 1; X represents $(CH_2)_n$, where n stands for 0; Y represents $NR^7$, where $R^7$ represents H; and $R^1$, $R^2$, tBu and P* have the significance given earlier.

In the first step, a compound of formula (V), prepared in a manner similar to that shown earlier in Reaction Scheme A, is reacted with an isothiocyanate compound of formula (XXXIV), to give a compound of formula (XXXV). This reaction is carried out in a conventional manner in an organic solvent which is inert under the reaction conditions, e.g. an aromatic hydrocarbon such as benzene, toluene or xylene, in the presence of an organic base such as triethylamine or tetramethylguanidine.

The resulting compound of formula (XXXV) is cyclised to give a compound of formula (IX) by treatment with a base, e.g. triethylamine, in an organic solvent, e.g. toluene, at an elevated temperature.

The cyclised compound of formula (IX) may then be converted to a compound of formula (II) in an analogous manner to that described earlier in Reaction Scheme A.

Reaction Scheme D

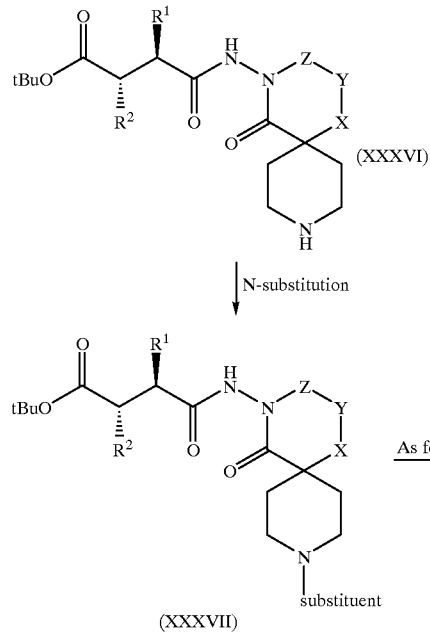

Referring to Reaction Scheme D, a compound of formula (XXXVII) may be prepared from a compound of formula (XXXVI). In this case, Z represents CO; W represents $(CR^3R^4)_m$, where m stands for 1, $R^3$ and $R^4$ together represent lower alkylene in which one or more $CH_2$ groups is optionally replaced by a nitrogen atom, where the nitrogen atom may itself be substituted; X represents $(CH_2)_n$, where n stands for 0; Y represents $NR^7$, where $R^7$ represents H; and $R^1$, $R^2$ and tBu have the significance given earlier.

The starting compound of formula (XXXVI) may be prepared in an analogous manner to that of a compound of formula (IX) as described in Reaction Scheme B earlier.

As illustrated, the heteroatom present within W is a nitrogen atom, which is unsubstituted in the compound of formula (XXXVI), and substituted in the compound of formula (XXXVII).

The functionalisation of the nitrogen atom may be performed by the reaction of a compound of formula (XXXVI) with, for example, a carboxylic acid chloride or a sulphonic acid chloride, in the presence of a suitable organic base, e.g. pyridine; or by a condensation reaction carried out under the known conditions of a peptide coupling reaction, as mentioned above; or by a reductive amination reaction, for example, reaction with an aldehyde followed by catalytic reduction or treatment with a hydride reducing agent, such as sodium cyanoborohydride.

The conversion of a compound of formula (XXXVII) to a compound of formula (II) may be performed in a manner analogous to that described earlier in Reaction Scheme A.

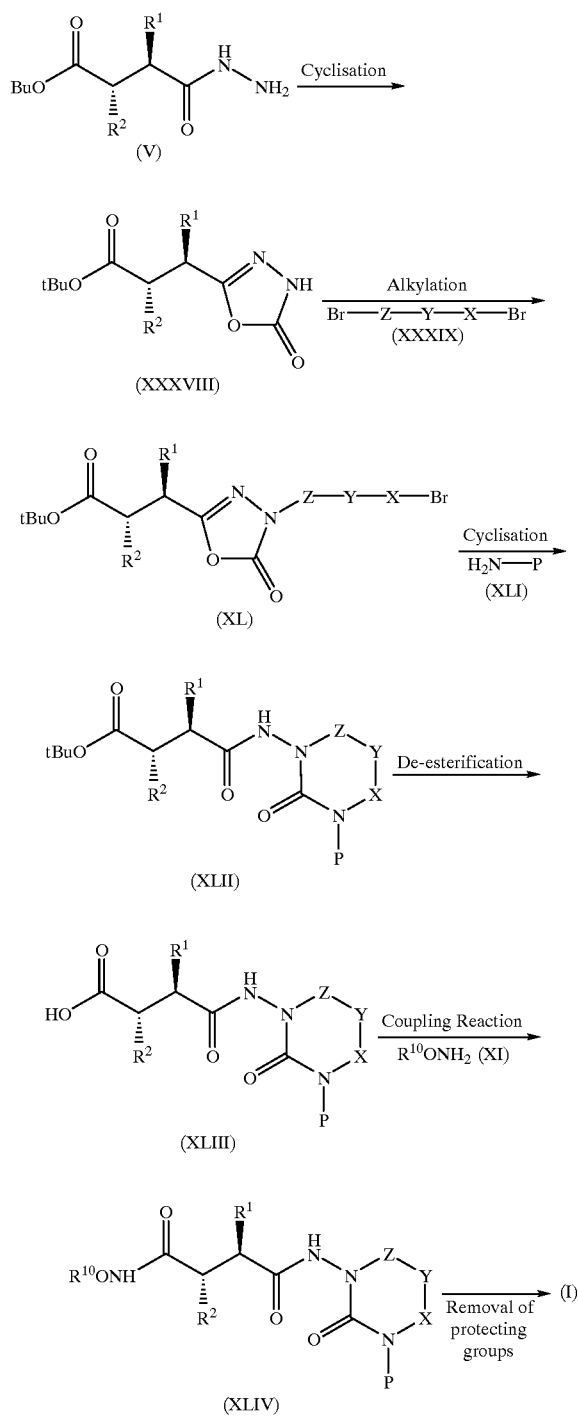

Compounds of formula (I) or (Ia) where Z represents $CH_2$; W represents $NR^5$, where $R^5$ represents H; X represents $—(CH_2)_n—$, where n stands for 0; Y represents $—(CH_2)_p—$, where p stands for 1; and $R^1$, $R^2$, tBu and P have the significance given earlier, may be synthesised as illustrated in Reaction Scheme E Firstly, a compound of formula (V) is cyclised to give a compound of formula (XXXVIII). This cyclisation is effected by treatment of a solution of a compound of formula (V) in an organic solvent with phosgene, in the presence of a base, at about 0° C. to about room temperature. Suitably, this reaction is carried out in an organic solvent which is inert under the reaction conditions, e.g. tetrahydrofuran. An example of a suitable base is sodium carbonate.

A thus obtained compound of formula (XXXVIII) may then be alkylated to give a compound of formula (XL). This alkylation may be performed by firstly treating a solution of a compound of formula (XXXVIII) in an organic solvent with a suitable base, followed by the addition of a di-bromo compound of formula (XXXIX). An example of a suitable solvent is dimethylformamide, and an example of a suitable base is sodium hydride.

Treatment of a solution of the resulting bromo-compound of formula (XL) in an organic solvent with a N-protected amino compound of formula (XLI), with heating, gives a compound of formula (XLII).

The de-esterification, and subsequent coupling reaction of a compound of formula (XLII), through a compound of formula (XLIII), to give a compound of formula (XLIV) may then be performed in a similar manner to that described in Reaction Scheme A. The step of removing the $R^{10}$ group may also remove the protecting group P.

Reaction Scheme F

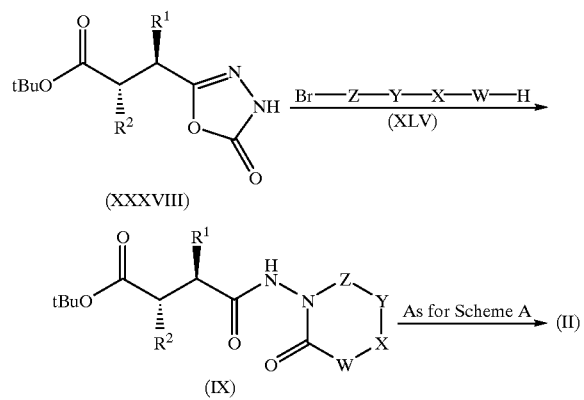

Reaction scheme F illustrates the synthesis of compounds of formula (II) where Z represents $CH_2$; W represents $NR^5$, where $R^5$ represents H; X represents $—(CH_2)_n—$, where n stands for 0; Y represents CO; and $R^1$, $R^2$ and tBu have the significance given earlier.

The starting compound of formula (XXXVIII) may be prepared in an analogous manner to that described earlier in Reaction Scheme E.

A thus obtained compound of formula (XXXVIII) may then be alkylated to give a compound of formula (IX). This alkylation may be performed by firstly treating a solution of a compound of formula (XXVIII) in an organic solvent with a suitable base, followed by the addition of a bromo-compound of formula (XLV). An example of a suitable solvent is dimethylformamide, and an example of a suitable base is sodium hydride.

The conversion of a compound of formula (IX) to a compound of formula (II) may be performed in a manner analogous to that described earlier in Reaction Scheme A.

Reaction Scheme G

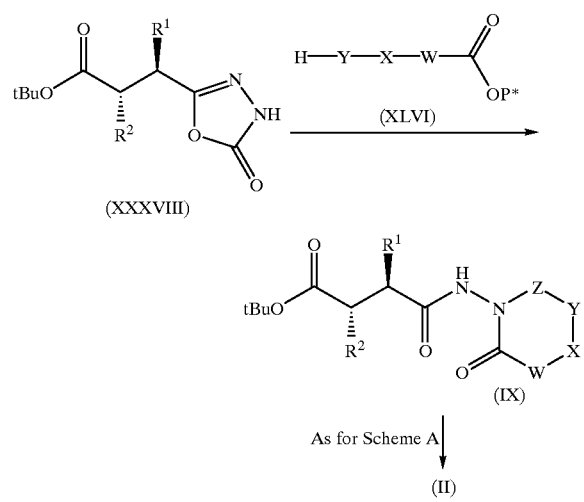

Reaction Scheme G illustrates the synthesis of compounds for formula (II) where Z represents CO; Y represents $NR^7$; X represents $—(CH_2)_n—$, where n stands for 0; W represents $(CR^3R^4)_m$, where m stands for 1; and $R^1$, $R^2$, $R^3$, $R^4$, tBu and P* have the significance given earlier.

The starting compound of formula (XXXVIII) may be prepared in an analogous manner to that described earlier in Reaction Scheme E.

Subsequently, a compound of formula (IX) may be obtained by the reaction of a solution of a compound of formula (XXXVIII) in an organic solvent, with a compound of formula (XLVI), in the presence of an organic base. A suitable solvent would be an aromatic hydrocarbon, e.g. toluene, and an example of a suitable organic base would be triethylamine.

The conversion of a compound of formula (IX) to a compound of formula (II) may be performed in a manner analogous to that described earlier in Reaction Scheme A.

Reaction Scheme H

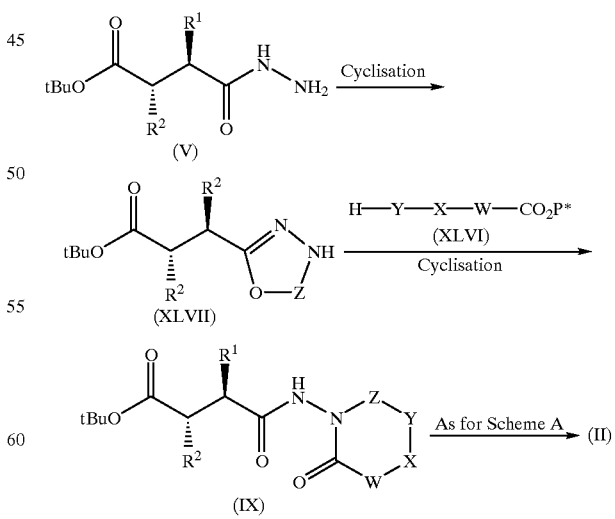

Turning to Reaction Scheme H, the preparation of compounds of formula (II) is shown, where Z represents CS; Y represents $NR^7$, where $R^7$ represents Me; X represents —(CH$_2$)$_n$—, where n stands for 1; W represents —(CR$^3$R$^4$)$_m$—, where m stands for 0; and R$^1$, R$^2$, R$^3$, R$^4$, tBu and P* have the significance given earlier.

The first step comprises the cyclisation of a compound of formula (V) to give a compound of formula (XLVII). This cyclisation is performed by reaction with thiophosgene in the presence of a base, e.g. sodium carbonate, at about 0° C. to about room temperature. Suitably, this reaction is carried out in an organic solvent which is inert under the reaction conditions, e.g. tetrahydrofuran.

The reaction of the resulting compound of formula (XLVII) with a compound of formula (XLVI) gives a compound of formula (IX). The step is performed in a suitably inert organic solvent e.g. toluene, in the presence of a base, e.g. triethylamine, at an elevated temperature.

The conversion of a compound of formula (IX) to a compound of formula (II) may be performed in a manner analogous to that described earlier in Reaction Scheme A.

Reaction Scheme I

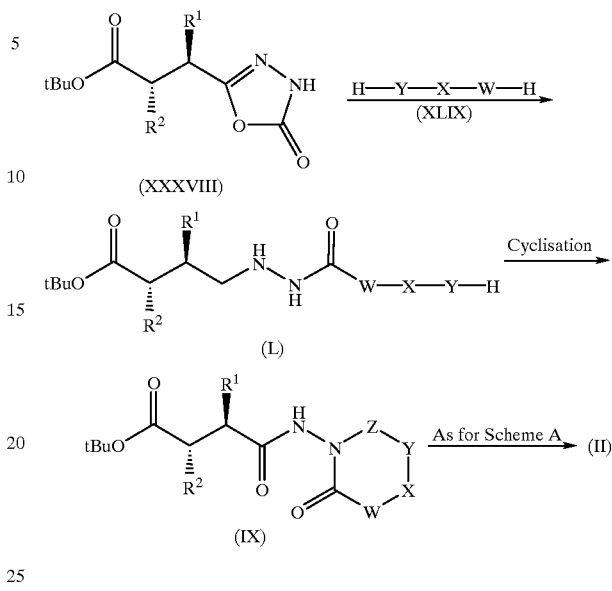

Referring to Reaction Scheme I, compounds where Z represents CO; Y represents NR$^7$; X represents CO; W represents NR$^5$; R* has the significance given earlier to R$^5$ and R$^7$, and where R$^5$ has the same significance as R$^7$; and R$^1$, R$^2$ and tBu have the significance given earlier, may be synthesised as shown.

The starting compound of formula (XXXVIII) may be prepared in an analogous manner to that described earlier in Reaction Scheme E.

Treatment of a solution of the compound of formula (XXXVIII) with the isocyanate compound of formula (XLVIII) gives the compound of formula (IX). The reaction is performed in a solvent inert under the reaction conditions, e.g. dimethylformamide, with treatment with a suitable base, e.g. sodium hydride, followed by addition of the compound of formula (XLVIII).

A N-deprotection of a compound of formula (IX) may be required, and is carried out in a manner known per se. For example, the benzyl group may be removed by hydrogenolysis.

Subsequently, conversion of a compound of formula (IX) to a compound of formula (II) may be performed in a manner analogous to that described earlier in Reaction Scheme A.

Reaction Scheme J

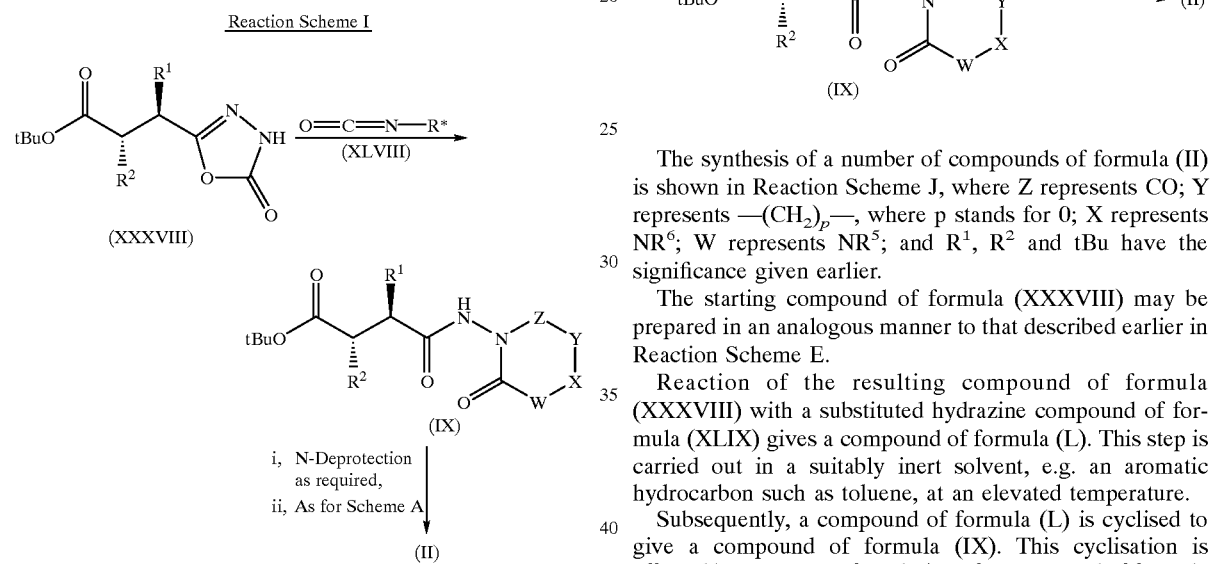

The synthesis of a number of compounds of formula (II) is shown in Reaction Scheme J, where Z represents CO; Y represents —(CH$_2$)$_p$—, where p stands for 0; X represents NR$^6$; W represents NR$^5$; and R$^1$, R$^2$ and tBu have the significance given earlier.

The starting compound of formula (XXXVIII) may be prepared in an analogous manner to that described earlier in Reaction Scheme E.

Reaction of the resulting compound of formula (XXXVIII) with a substituted hydrazine compound of formula (XLIX) gives a compound of formula (L). This step is carried out in a suitably inert solvent, e.g. an aromatic hydrocarbon such as toluene, at an elevated temperature.

Subsequently, a compound of formula (L) is cyclised to give a compound of formula (IX). This cyclisation is effected by treatment of a solution of a compound of formula (L) in an organic solvent with phosgene, in the presence of a base, at about 0° C. to about room temperature. Suitably, this reaction is carried out in an organic solvent which is inert under the reaction conditions, e.g. tetrahydrofuran. An example of a suitable base is sodium carbonate.

The conversion of a compound of formula (IX) to a compound of formula (II) may be performed in a manner analogous to that described earlier in Reaction Scheme A.

Reaction Scheme K

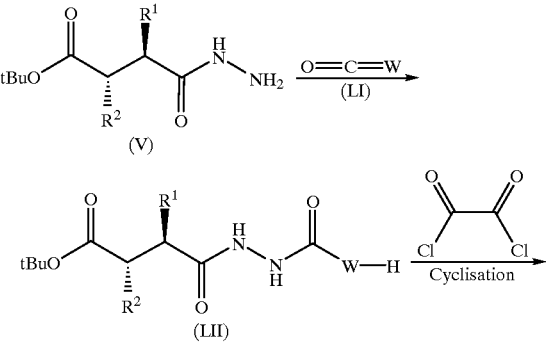

-continued

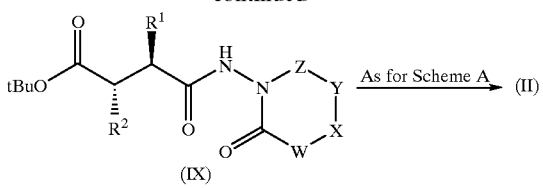

Compounds of formula (II) where Z represents CO; Y represents CO; X represents —(CH$_2$)$_n$—, where n stands for 0; W represents NR$^5$, where R$^5$ has the significance given earlier; and R$^1$, R$^2$ and tBu have the significance given earlier, may be synthesised as shown in Reaction Scheme K.

Condensation of a compound of formula (V) with a substituted isocyanate of formula (LI) gives a compound of formula (LII). The reaction is carried out in the presence of a suitable base, e.g. pyridine, which may also be used as solvent.

Subsequently, reaction of a solution of a compound of formula (LII) with oxalyl chloride gives a compound of formula (IX). The reaction may be performed in a suitably inert solvent, such as a halogenated hydrocarbon, e.g. dichloromethane, in the presence of a base, e.g. pyridine, at about 0° C. to about room temperature.

The conversion of a compound of formula (IX) to a compound of formula (II) may be performed in a manner analogous to that described earlier in Reaction Scheme A.

Reaction Scheme L

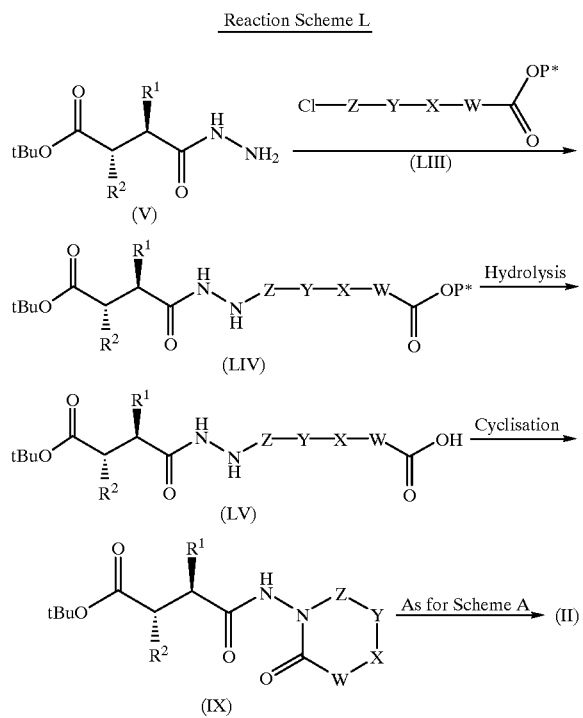

Reaction Scheme L shows the synthesis of compounds of formula (II), where Z represents SO$_2$; Y represents NR$^7$, where R$^7$ represents H; X represents —(CH$_2$)$_n$, where n stands for 0; W represents (CR$^3$R$^4$)$_m$, where m stands for 1, R$^3$ and R$^4$ represent H; and R$^1$, R$^2$, tBu and P* have the significance given earlier.

Reaction of a hydrazide compound of formula (V) with a chloro-compound of formula (LIII) gives a compound of formula (LIV). The reaction is performed in a suitably inert solvent, e.g. dichloromethane, in the presence of a base, e.g. pyridine.

Removal of the protecting group P* may then be performed in a conventional manner as described earlier to give a compound of formula (LV). In the case of a methyl group, de-protection may be effected by hydrolysis with lithium hydroxide, in a solvent inert to the reaction conditions, e.g. a mixture of methanol and tetrahydrofuran.

Subsequent cyclisation of a compound of formula (LV) to give a compound of formula (IX) may be effected under the known conditions of a peptide coupling reaction, for example, using 1-ethyl-3-(3-dimethylaminopropyl) carbodiimide hydrochloride in e.g. dimethyformamide.

The conversion of a compound of formula (IX) to a compound of formula (II) may be performed in a manner analogous to that described earlier in Reaction Scheme A.

Although not illustrated in the reaction schemes and in the formulae of the intermediates, the bond between W and X can be a single or a double bond or a bond which is part of an aromatic system. In particular in case when W is CR$^{11}$ and X is CR$^{12}$ and R$^{11}$ and R$^{12}$ together with the sp2 carbon atoms to which they are attached form a lower cycloalkenyl, aryl or heteroaryl ring, the bond between W and X becomes a double bond or a bond which is part of an aromatic system.

Compounds with such double and aromatic bonds between W and X can be prepared as described in Schemes B and C, in particular wherein Z is CO or CS and Y is NH. Preparation of compounds wherein Z is SO$_2$ and Y is NR$^7$ can be prepared by reaction of V with reagent XXV where X—W are in the ring formed by CR$^{12}$ and CR$^{11}$ and Y is NR$^7$ to give XXVI and then XXVII followed by cyclisation.

Corresponding compounds with other combinations in Y and Z can be prepared in analogy to the chemistry described in the reaction schemes before. For example, compounds wherein Z is CO and Y is NR$^7$ can be prepared by reaction of a compound V shown in Scheme A with a reagent of formula HOOCWXY(P) (XXXa), wherein in the reagent Y is NR$^7$ and X—W are in the ring formed by CR$^{12}$ and CR$^{11}$, followed by removal of the protecting group on Y to give a compound of formula L as shown in scheme J. A compound of formula L is then cyclised as described in scheme J during which the CO group is included to give a compound of formula IX.

The compounds of formula (II) in which Z represents CH$_2$, Y represents CO and X and W together form a double bond that is via CR$^{12}$ and CR$^{11}$ part of a fused lower cycloalkenyl, aryl or heteroaryl ring can be prepared, for example, as illustrated in Reaction Scheme L, by reaction of a chloro or bromo ketone of formula Cl(or Br)ZYXWCOOP* (compare formula LIII) wherein Z is CH$_2$, Y is CO and X and W together form a double bond that is part of a fused lower cycloalkenyl, aryl or heteroaryl ring with a hydrazide of formula (V) to give a compound of formula (LIV). The reaction is performed in a suitably inert solvent, such as dichloro-methane, in the presence of a base, such as triethylamine or by use of an inorganic base, such as sodium bicarbonate, in a polar inert solvent, such as dimethylformamide. The remaining reactions would be carried out as described previously.

The compounds of formula (II) in which Z represents CH$_2$, Y represents NR7 and X and W together form a double bond that is via CR$^{12}$ and CR$^{11}$ part of a fused lower cycloalkenyl, aryl or heteroaryl ring can be prepared, for example, as illustrated in Reaction Scheme L, by reaction of a bromide of formula BrZYXWCOOP* (compare formula LIII) wherein Z is CH$_2$, Y is NR$^7$ and X and W together form a double bond that is part of a fused lower cycloalkenyl, aryl or heteroaryl ring with a hydrazide of formula (V) to give a compound of formula (LIV). The reaction is performed in a suitably inert solvent, such as dichloromethane, in the presence of a base, such as triethylamine or by use of an inorganic base, such as sodium bicarbonate, in a polar inert solvent, such as dimethylformamide The remaining reactions would be carried out as described previously.

With regard to the starting materials that are known compounds some of these may be purchased from commercial suppliers. Other starting materials that are known and their analogues can be prepared by methods well known in the art. Examples of compounds available from commercial suppliers, and citations to the synthesis of other compounds and their analogues are provided in the following:

The compounds of formula (III) can be prepared by methods disclosed in published patent applications: EP-A-0497192 and EP-A-0574758 and also using the methods of Beckett et al, Synlett 1993, 137 and Pratt et al, Synlett 1998, 531.

The compounds of formula (VI) where Z represents $SO_2$ can be obtained from commercial suppliers (e.g. 2-phthalimidoethanesulphonyl chloride, Asta Tech, Inc. cat. no. N88865), or from commercially available sulphonic acids (e.g. 2-(2-pyridyl)ethanesulfonic acid, Aldrich cat. no. 30,392-5) by methods well known in the art such as treatment with $PCl_5$, or by adaptation of the methods provided in Atwell G. J., Cain B. F. and Denny W. A., J. Med. Chem. 1977,20, 128–134; and Kricheldorf H. R. and Schultz J., Synthesis 1976, 11, 739–741.

The compounds of formula (VI) where Z represents CO can be obtained from commercial suppliers (e.g. Fmoc-Leu-Cl, Advanced ChemTech Product cat. no. FL2353; Fmoc-Phe-Cl, Advanced ChemTech Product cat. no. FF2427), or prepared by adaptation of the methods provided in Gopi et al, Tetrahedron Letters 1998, 39(52), 9769–9772 and Schmidt et al, Synthesis 1988, 6, 475–477.

The compounds of formula (XXX) and (XXXa) where Z represents CO can be obtained from commercial suppliers (e.g. Fmoc-Gly-OH, Aldrich cat. no. 33,528-2; 3-phthalimidopropionic acid, Lancaster Synthesis cat. no. 13,535).

The compounds of formula (XII) can be obtained from commercial suppliers (e.g. Tyger Scientific Inc. cat. no. 342), or prepared by methods disclosed in WO-9309136, or by adaptation of the methods provided by Wen J. J. and Crews M. C., Tetrahedron Asymmetry 1998, 9(11), 1855–1858; and Prabhakaran et al, J. Am. Chem. Soc. 1988, 110(17), 5779–5784.

The compounds of formula (XIII) can be prepared from iminoacetic acid (Aldrich cat. no. 22,000-0) by adaptation of the methods disclosed in EP-A-0 774464 or by adaptation of the methods provided in Bernard et al, Tetrahedron 1996, 52(29), 9793–9804; Cheng S. Bioorg.Med. Chem. 1996, 4(5), 727–737; WO-940621; Kirth et al, Tetrahedron 1992, 48(8), 1407–1416; Barton et al, J. Med. Chem. 1990, 33(6) 1600–1606; and Epton et al, Polymer 1982, 23(5), 771–773.

The compounds of formula (XV) can be prepared by adaptation of the methods provided in Yoon et al, Chem. Commun. 1998, 24, 2703–2704; Altural B. Org. Prep. Proceed. Int. 1991, 23(2), 147–151; Lalezari I. J., Heterocyclic Chem. 1985, 23(3), 741–743; Wright et al J. Med. Chem. 1969, 12(3), 379–381; Jacobsen et al, Aust. J. Chem. 1979, 32(1), 153–160 and 161–165.

The compounds of formula (XVI) can be prepared by adaptation of the methods provided in Takimoto et al Chemical Abstracts 98:178868; Ratier M. Synth. Commun. 1989, 19(1–2), 285–291; Burgess et al, Org. Syn. 1973, 53 1857.

The compounds of formula (XXII) can be prepared by the method in Konecny et al Chemical Abstracts 121:82730.

The compounds of formula (XXV) and (LIII) can be prepared by adaptation of the methods provided in Unterhalt B. and Hanewaker G. A., Arch. Pharm. (Weinheim Ger.), 1989, 322(6), 389–390.

The compounds of formula (XXXII) can be prepared by adaptation of the methods of Nowick et al, J.Org. Chem. 1992, 57(26), 7364; and Eckert and Forster, Angew. Chem. Int. Ed.Engl., 1987, 26(9), 894; or can be obtained from commercial suppliers (e.g. (s)-(-)-2-isocyanato-4-methylvaleric acid methyl ester, TCI-US cat. no. 10467; (S)-(-)-2-isocyanato-3-methylbutyric acid methyl ester, Aldrich cat. no. 42,980-5). Other compounds of formula XXXII can be prepared by methods provided in the examples, starting from commercially available cyclic amino acid esters (e.g. methyl 2-aminothiophene-3-carboxylate, Maybridge cat. no. GK02784; methyl 2-amino-1-cyclohexene-1-carboxylate, Acros cat. no 29276-0010).

The compounds of formula (XXXIV) can be obtained from commercial suppliers (e.g. methyl L-2-isothiocyanato-3-methylbutyrate, Transwld cat. no. M3 056; methyl L-2-isothiocyanato 4-methylvalerate, Transwld cat. no. M3058); or can be prepared by adaptation of the methods of Floch and Sticzay, Chem. Zvesti., 1980, 34(3),389 and Floch and Kovac, Chem. Commun., 1975, 40(9), 2845.

The compounds of formula (XXXIX) can be obtained from commercial suppliers (e.g. 1,2-dibromoethane, Aldrich cat. no. D4,075-2).

The compounds of formula (XLI) can be obtained from commercial suppliers (e.g. benzylamine, Adrich cat. no. 18,570-1).

The compounds of formula (XLV) can be obtained from commercial suppliers (e.g. 2-bromoacetamide, Aldrich cat. no. 30,127-2).

The compounds of formula (XLVI) can be obtained from commercial suppliers (e.g. sarcosine ethyl ester, Aldrich cat. no. 25,508-4; N-benzylglycine ethyl ester, Aldrich cat. no. B22,270-4).

The compounds of formula (XLIX) can be obtained from commercial suppliers (e.g. N-methylhydrazine, Aldrich cat. no. M5,000-1; N-benzylhydrazine dihydrochloride, Aldrich cat. no. B2,285-2).

The compounds of formula (XLVIII) and (LI) can be obtained from commercial suppliers (e.g. benzyl isocyanate, Aldrich cat. no. 22,726-9).

As mentioned earlier, the hydrazine derivatives provided by the present invention inhibit the release of TNF-α from mammalian cells. This can be demonstrated using the in vitro test procedure described hereinafter:

THP1 cells were cultivated in RPMI 1640 medium supplemented with antibiotics and 10% foetal calf serum, harvested by centrifugation and diluted to $5 \times 10^5$ cells/ml in the above medium supplemented with 20 mM HEPES buffer. Aliquots (200 μl) of the cell suspension were plated out on 96 well culture plates and incubated for 0.5 hour at 37° C. prior to the addition of the test compounds. The latter were dissolved in dimethyl sulphoxide (DMSO) to a stock concentration of 1.2 mM which was diluted with phosphate buffered saline/10% DMSO solution to provide test compounds in final concentrations of $10^{-9}$ to $10^{-5}$ M, with each concentration being tested in duplicate. The cells were incubated with the test compounds for 0.5 hour at 37° C., LPS (bacterial lipopolysaccharide) was then added to a concentration of 2 mg/ml and incubation was continued for 3 hours at 37° C. in an atmosphere containing 5% $CO_2$ and at 95% relative humidity. After centrifugation at 260 g for 10 minutes an aliquot of each supernatant was removed and the amount of TNF-α was estimated by ELISA (R & D Systems Europe Ltd., Abingdon, England). The concentration of test compound which brings about 50% inhibition of LPS-induced TNF-α release ($IC_{50}$) was computed from the dose-response curve.

Compounds A–S listed hereinafter have an $IC_{50}$ of 147–1450 nMol in the foregoing test procedure:

Compound A: (E)-2(R)-[1(S)-(Hydroxycarbamoyl)-4-phenyl-3-butenyl]-4-methyl-(2,5-dioxo-1-imidazolidinyl)valeramide Compound B: (E)-N-(Hexahydro-2,6-dioxo-1-pyrimidinyl)-2(R)-[1(S)-(hydroxycarbamoyl)-4-phenyl-3-butenyl]-4-methylvaleramide Compound C: 2(R)-[4-Cyclohexyl-1(S)-(hydroxycarbamoyl)butyl]-4-methyl-N-(2,5-dioxo-1-imidazolidinyl)valeramide Compound D: (E)-N-(Tetrahydro-3-oxo-2H-1,2,4-thiadiazin-2-yl)-2(R)-[1(S)-(hydroxycarbamoyl)-4-phenyl-3-butenyl]-4-methylvaleramide S,S-dioxide;

Compound E: 2(R)-[1(S)-(Hydroxycarbamoyl)-4-phenylbutyl]-4-methyl-N-(2,6-dioxo-1-piperazinyl)valeramide p-toluenesulphonate Compound F: 2(R)-[1(S)-(Hydroxycarbamoyl)-4-phenylbutyl]-N-(4(S)-isopropyl-2,5-dioxo-1-imidazolidinyl)-4-methylvaleramide Compound G: 2(R)-[1(S)-(Hydroxycarbamoyl)-4-phenylbutyl]-4-methyl-N-[4(S)-(1(S)-methylpropyl)-2,5-dioxo-1-imidazolidinylvaleramide Compound H: 2(R)-[1(S)-(Hydroxycarbamoyl)-4-phenylbutyl]-4-methyl-N-[4(S)-[2-(methylthio)ethyl]-2,5-dioxo-1-imidazolidinyl]valeramide Compound I: 2(R)-[1(S)-(Hydroxycarbamoyl)-4-phenylbutyl]-N-[4(S)-(hydroxymethyl)-2,5-dioxo-1-imidazolidinyl]-4-methylvaleramide Compound J: 2(R)-[1(S)-(Hydroxycarbamoyl)-4-phenylbutyl]-N-(4(S)-isopropyl-5-oxo-2-thioxo-1-imidazolidinyl)-4-methylvaleramide Compound K: (E)-2(R)-[1(S)-(Hydroxycarbamoyl)-4-phenyl-3-butenyl]-N-[4(S)-(1(S)-methylpropyl)-2,5-dioxo-1-imidazolidinyl]-4-methylvaleramide Compound L: (E)-2(R)-[1(S)-(Hydroxycarbamoyl)-4-phenyl-3-butenyl]-N-[4(S)-(hydroxymethyl)-2,5-dioxo-1-imidazolidinyl]-4-methylvaleramide Compound M: Benzyl 3-[2(R)-[1(S)-(hydroxycarbamoyl)-4-phenylbutyl]-4-methylvaleramido]-2,4-dioxo-1,3,8-triazaspiro[4,5]decane-8-carboxylate Compound N: N-(1,2,3,4-Tetrahydro-2,4-dioxothieno[3,2-d]pyrimidin-3-yl)-2(R)-[1(S)-(hydroxycarbamoyl)-4-phenylbutyl]-4-methylvaleramide Compound O: N-(1,2,3,4-Tetrahydro-2,4-dioxothieno[3,4-d]pyrimidin-3-yl)-2(R)-[1(S)-(hydroxycarbamoyl)-4-phenylbutyl]-4-methylvaleramide Compound P: 2(R)-[1(S)-(Hydroxycarbamoyl)-4-phenylbutyl]-N-[4(S)-methoxymethyl)-2,5-dioxo-1-imidazolidinyl]-4-methylvaleramide Compound Q: 2(R)-[1(S)-(Hydroxycarbamoyl)-4-phenylbutyl]-4-methyl-N-(2,5-dioxo-1-imidazolidinyl)valeramide Compound R: 1-(8-Acetyl-2,4-dioxo-1,3,8-triazaspiro[4.5]decan-3-yl)-2(R)-[1(S)-(hydroxycarbamoyl)-4-phenylbutyl]-4-methylvaleramide Compound S: 2(R)-[2-(4-Biphenylyl)-1(S)-(hydroxycarbamoyl)ethyl]-N-(2,5-dioxo-1-imidazolidinyl)-4-methylvaleramide

| Compound | $IC_{50}$ (nMol) |
|---|---|
| A | 280 |
| B | 382 |
| C | 242 |
| D | 389 |
| E | 1450 |
| F | 156 |
| G | 147 |
| H | 234 |
| I | 387 |
| J | 597 |
| K | 162 |
| L | 302 |
| M | 620 |
| N | 172 |
| O | 177 |
| P | 346 |
| Q | 234 |
| R | 481 |
| S | 308 |

The hydrazine derivatives provided by the present invention (i.e. the compounds of formula (I)and (Ia) and their pharmaceutically acceptable salts), can be used as medicaments, for example in the form of pharmaceutical preparations. The pharmaceutical preparations can be administered orally, e.g. in the form of tablets, coated tablets, dragées, hard and soft gelatine capsules, solutions, emulsions or suspensions. However, they can also be administered rectally, e.g. in the form of suppositories, or parenterally, e.g. in the form of injection solutions.

For the manufacture of pharmaceutical preparations the hydrazine derivatives can be formulated with therapeutically inert, inorganic or organic carriers. Lactose, corn starch or derivatives thereof, talc, stearic acid or its salts can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active ingredient no carriers are, however, generally required in the case of soft gelatine capsules. Suitable carriers for the manufacture of solutions and syrups are, for example, water, polyols, saccharose, invert sugar, glucose and the like. Suitable carriers for the manufacture of injection solutions are, for example, water, alcohols, polyols, glycerine, vegetable oils and the like. Natural and hardened oils, waxes, fats, semi-liquid polyols and the like are suitable carriers for the manufacture of suppositories.

The pharmaceutical preparations can also contain preservatives, stabilizers, wetting agents, emulsifiers, sweeteners, colorants, flavorants, salts for adjustment of the osmotic pressure, buffers, masking agents or antioxidants. They may also contain other therapeutically active substances.

Medicaments containing an aforementioned hydrazine derivative and a therapeutically acceptable carrier as well as a process for the manufacture of such medicaments are also objects of the present invention. This process comprises bringing a compound of formula (I) or (Ia) or a pharmaceutically acceptable salt thereof into a galenical administration form together with a therapeutically inert carrier material and, if desired, one or more additional therapeutically active substances.

A further object of the invention comprises the use of the hydrazine derivatives provided by the invention in the treatment of inflammatory and autoimmune diseases (e.g.

rheumatoid arthritis, inflammatory bowel disease, multiple sclerosis and psoriasis), osteoarthritis, respiratory diseases (e.g. asthma and chronic obstructive pulmonary disease), tumours, cachexia, cardiovascular diseases (e.g. congestive heart failure), fever, haemorrhage and sepsis. The dosage can vary within wide limits and will, of course, be adjusted to the individual requirements in each particular case. In general, in the case of administration to adults, a daily dosage of about 1–20 mg/kg, preferably about 3–5 mg/kg, should be appropriate, although the upper limit may be exceeded when this is found to be expedient. The daily dosage can be administered as a single dosage or in divided dosages.

The contents of GB Patent Application No. 9827408.7, filed Dec. 11, 1998 and GB Patent Application No. 9925211.6, filed Oct. 25, 1999, are incorporated herein by reference.

The invention will be better understood by reference to the following Examples which illustrate but do not limit the invention described herein.

EXAMPLE 1

(E)-2(R)-[1(S)-(Hydroxycarbamoyl)-4-phenyl-3-butenyl]-4-methyl-N-(2,5-dioxo-1-imidazolidinyl) valeramide A solution of 0.234 g of (E)-2(R)-[1(S)-[(tetrahydro-2 (RS)-pyranyloxy)carbamoyl-4-phenyl-3-butenyl]-4-methyl-N-(2,5-dioxo-1-imidazolidinyl)valeramide in 3 ml of methanol was treated with 0.010 g of p-toluenesulphonic acid monohydrate. The mixture was stirred for 2 hours at room temperature and evaporated. The residue was triturated with diethyl ether, filtered off and dried to give 0.122 g of (E)-2(R)-[1(S)-(hydroxycarbamoyl)-4-phenyl-3-butenyl]-4-methyl-N-(2,5-dioxo-1-imidazolidinyl)valeramide in the form of a white solid.

MS: 403 (M+H)$^+$.

HPLC: Gradient elution using solvent A containing 20% solvent B for 5 minutes increasing to 90% solvent B over 10 minutes; flow rate 1 ml/minute. Retention time: 8.87 minutes. Solvent A: $H_2O$/0.1% TFA; solvent B: $CH_3CN$/0.085% TFA. Column type: LUNA3uC8.

The (E)-2(R)-[1(S)-[(tetrahydro-2(RS)-pyranyloxy) carbamoyl-4-phenyl-3-butenyl]-4-methyl-N-(2,5-dioxo-1-imidazolidinyl)valeramide used as the starting material was prepared as follows:

(i) A solution of 253.3 g of 4-tert-butyl hydrogen 2(R)-isobutylsuccinate in 2 l of dry tetrahydrofuran was cooled to −70° C. while stirring under nitrogen. 1.2 l of a 2M solution of lithium diisopropylamide in tetrahydrofuran were added dropwise and the mixture was stirred at −70° C. for 30 minutes. A solution of 282 g of cinnamyl bromide in 2 l of dry tetrahydrofuran was then added dropwise and the mixture was left to come to room temperature gradually. After stirring overnight the tetrahydrofuran was evaporated and the residue was partitioned between ethyl acetate and 2M hydrochloric acid solution. The ethyl acetate phase was washed with a further portion of 2M hydrochloric acid solution, water and saturated sodium chloride solution and then dried over anhydrous magnesium sulphate. The solvent was evaporated to give a gummy solid. This was suspended in 2 l of hexane and the solid was removed by filtration (crop 1:77.3 g). The hexane solution was treated with 109 g of cyclohexylamine, the mixture was left to stand for 1 hour at room temperature and for 16 hours at 4° C. The solid which formed was collected by filtration and dissolved in 2.5 l of methyl tert.butyl ether and 1.5 l of 2M hydrochloric to give a clear solution. The organic phase was washed twice with water and with saturated sodium chloride solution and subsequently dried over anhydrous magnesium sulphate. After evaporation of the solvent there were obtained 189.8 g of a solid (crop 2).The two crops were united and dried to give 267.1 g of (E)-2(R)-[1(R)-(tert-butoxycarbonyl)-4-phenyl-3-butenyl]-4-methylvaleric acid in the form of a pale cream coloured solid.

(ii) The compound obtained in part (i) was dissolved in 2.5 l of dry tetrahydrofuran, cooled to −78° C. with stirring and 860 ml of a 2M solution of lithium diisopropylamide in tetrahydrofuran were added dropwise over 2 hours. After stirring for 0.5 hour at −78° C., 330 ml of methanol were added dropwise. The mixture was left to come to room temperature gradually and was then stirred overnight. The tetrahydrofuran was evaporated and the residue was partitioned between ethyl acetate and 2M hydrochloric acid solution. The ethyl acetate phase was washed in succession with two portions of hydrochloric acid solution, two portions of water and saturated sodium chloride solution and then dried over magnesium sulphate. After evaporation there was obtained an orange oil which contained a mixture of the 1(S),2(R) and 1(R),2(R) isomers of E-2-[1-(tert-butoxycarbonyl)-4-phenyl-3-butenyl]-4-methylvaleric acid. The foregoing epimerization procedure was repeated three times to give a mixture substantially enriched in the 1(S),2(R) isomer. The crude product was dissolved in 2500 ml of hexane and the solution was treated with 89 ml of tert.butylamine. After leaving to stand at 4° C., the precipitated salt was filtered off and dried. There were obtained 210.3 g of a pale cream solid which was converted into the free acid by the procedure described above to give of (E)-2(R)-[1(S)-(tert-butoxycarbonyl)-4-phenyl-3-butenyl]-4-methylvaleric acid in the form of a yellow solid.

(iii) A solution of 20 g of (E)-2(R)-[1(S)-(tert-butoxycarbonyl)-4-phenyl-3-butenyl]-4-methylvaleric acid in 200 ml of dimethylformamide was cooled to 0° C. under nitrogen and treated with 11.8 g of pentafluorophenol and 12.3 g of 1-ethyl-3-(3-dimethylaminopropyl)carbodiimide hydrochloride. The mixture was stirred for 2.5 hours at 0° C. and then treated with 19.8 g of hydrazine hydrochloride and 33 ml of triethylamine. The mixture was left to warm to room temperature and was then stirred overnight. Evaporation gave a residue which was dissolved in ethyl acetate and washed with 2M aqueous hydrogen chloride, 5% aqueous sodium hydrogen carbonate and saturated aqueous sodium chloride. Evaporation gave a solid which was washed with ether/hexane (1:1) and dried to give 12.1 g of of (E)-2(R)-[1(S)-(tert-butoxycarbonyl)-4-phenyl-3-butenyl]-4-methylvalerohydrazide in the form of a white solid.

MS: 361 (M+H)$^+$.

(iv) A solution of 1.0 g of (E)-2(R)-[1(S)-(tert-butoxycarbonyl)-4-phenyl-3-butenyl]-4-methylvalerohydrazide in 10 ml of dimethylformamide was treated with 1.24 g of N-(9-fluorenylmethyloxycarbonyl)-glycine and 0.80 g of 1-ethyl-3-(3-dimethylaminopropyl) carbodiimide hydrochloride. The mixture was stirred overnight at room temperature and evaporated. The residue was dissolved in ethyl acetate and washed with 2M aqueous hydrogen chloride, 5% aqueous sodium hydrogen carbonate and saturated aqueous sodium chloride. Drying over anhydrous magnesium sulphate followed by evaporation and trituration with diethyl ether gave 1.54 g of (E)-2(R)-[1(S)-(tert-butoxycarbonyl)-4-phenyl-3-butenyl]-2'-[N-(9- fluorenylmethyloxycarbonyl)-glycinyl]-4-methylvalerohydrazide in the form of a white solid.

MS: 640 (M+H)⁺.

(v) A solution of 1.54 g of (E)-2(R)-[1(S)-(tert-butoxycarbonyl)-4-phenyl-3-butenyl]-2'-[N-(9-fluorenylmethyloxycarbonyl)-glycinyl]-4-methylvalerohydrazide in 20 ml of dichloromethane was treated with 1.0 ml of piperidine. The mixture was stirred for 1.5 hours at room temperature and evaporated. The residue was purified by flash column chromatography on silica gel using methanol/dichloromethane (1:9) for the elution to give 0.83 g of (E)-2(R)-[1(S)-(tert-butoxycarbonyl)-4-phenyl-3-butenyl]-2'-glycinyl-4-methylvalerohydrazide in the form of a white solid.

MS: 418 (M+H)⁺.

(vi) A solution of 0.83 g of (E)-2(R)-[1(S)-(tert-butoxycarbonyl)-4-phenyl-3-butenyl]-2'-glycinyl-4-methylvalerohydrazide in 50 ml of dichloromethane was cooled to 0° C. under nitrogen and treated with 0.76 ml of N-ethylmorpholine and 1.34 ml of a 1.93M solution of phosgene in toluene. The mixture was left to warm to room temperature and was stirred for 3 hours. The mixture was diluted with ethyl acetate and washed with 2M aqueous hydrogen chloride and saturated aqueous sodium chloride. The organic phase was dried over anhydrous magnesium sulphate and evaporated. Trituration of the residue with diethyl ether gave 0.783 g of (E)-2(R)-[1(S)-(tert-butoxycarbonyl)-4-phenyl-3-butenyl]-4-methyl-N-(2,5-dioxo 1-imidazolidinyl)valeramide in the form of a white solid.

MS: 444(M+H)⁺.

(vii) A solution of 0.783 g of (E)-2(R)-[1(S)-(tert-butoxycarbonyl)-4-phenyl-3-butenyl]-4-methyl-N-(2,5-dioxo-1-imidazolidinyl)valeramide in 20 ml of dichloromethane was treated with 10 ml of trifluoroacetic acid. The mixture was stirred at room temperature for 4 hours and evaporated. Traces of trifluoroacetic acid were removed by the three-fold addition and evaporation of toluene to give 0.805 g of (E)-2(R)-[1(S)-(carboxy)-4-phenyl-3-butenyl]-4-methyl-N-(2,5-dioxo-1-imidazolidinyl)valeramide in the form of a white solid.

MS: 388(M+H)⁺.

(viii) A solution of 0.805 g of(E)-2(R)-[1(S)-(carboxy)-4-phenyl-3-butenyl]-4-methyl-N-(2,5-dioxo-1-imidazolidinyl)valeramide in 3 ml of dimethylformamide was treated with 0.487 g of O-(tetrahydro-2H-pyran-2(RS)-yl)hydroxylamine. The mixture was cooled to 0° C. under nitrogen and treated with 0.439 g of 1-ethyl-3-(3-dimethylaminopropyl)carbodiimide hydrochloride. The mixture was left to warm to room temperature and was stirred overnight. Evaporation gave a residue which was dissolved in ethyl acetate and washed in sequence with 5% aqueous citric acid, 5% aqueous sodium hydrogen carbonate and saturated aqueous sodium chloride. Drying over anhydrous magnesium sulphate and evaporation gave a residue which was purified by flash column chromatography on silica gel using ethyl acetate for the elution to give 0.234 g of (E)-2(R)-[1(S)-[(tetrahydro-2(RS)-pyranyloxy)carbamoyl-4-phenyl-3-butenyl]-4-methyl-N-(2,5-dioxo-1-imidazolidinyl)valeramide in the form of a white foam.

MS: 487 (M+H)⁺.

EXAMPLE 2

(E)-N-(Hexahydro-(2,6-dioxo-1-pyrimidinyl)-2(R)-[1(S)-(hydroxycarbamoyl)-4-phenyl-3-butenyl]-4-methylvaleramide A solution of 0.098 g of (E)-N-(hexahydro-2,6-dioxo-1-pyrimidinyl)-2(R)-[1(S)-[(tetrahydro-2(RS)-pyranyloxy) carbamoyl-4-phenyl-3-butenyl]-4-methylvaleramide in 5 ml of methanol was treated with 0.010 g of p-toluenesulphonic acid monohydrate. The mixture was stirred for 3 hours at room temperature and evaporated. The residue was dissolved in ethyl acetate, washed with 5% aqueous sodium hydrogen carbonate, dried over anhydrous magnesium sulphate and evaporated. The residue was triturated with diethyl ether, filtered off and dried to give 0.025 g of (E)-N-(hexahydro-2,6-dioxo-1-pyrimidinyl)-2(R)-[1(S)-(hydroxycarbamoyl)-4-phenyl-3-butenyl]-4-methylvaleramide in the form of a white solid.

MS: 417 (M+H)⁺.

HPLC: Gradient elution using solvent A containing 5% solvent B increasing to 90% solvent B over 15 minutes; flow rate 1 ml/minute. Retention time: 9.14 minutes. Solvent A: H₂O/0.1% TFA; solvent B: CH₃CN/0.085% TFA. Column type: HYPERPEP 300A.

The (E)-N-(hexahydro-2,6-dioxo-1-pyrimidinyl)-2(R)-[1(S)-[(tetrahydro-2(RS)-pyranyloxy)carbamoyl-4-phenyl-3-butenyl]-4-methylvaleramide used as the starting material was prepared as follows:

(i) In an analogous manner to that described in Example 1, parts (i)–(iv), but using 3-N-phthalimidopropionic acid in place of N-(9-fluorenylmethyloxycarbonyl)-glycine, there was obtained (E)-2(R)-[1(S)-(tert-butoxycarbonyl)-4-phenyl-3-butenyl]-4-methyl-2'-[3-(N-phthalimidopropionyl)]valerohydrazide in the form of a white solid.

MS: 562 (M+H)⁺.

(ii) A solution of 3.74 g of (E)-2(R)-[1(S)-(tert-butoxycarbonyl)-4-phenyl-3-butenyl]-4-methyl-2'-[3-(N-phthalimidopropionyl)]valerohydrazide in 30 ml of ethanol was treated with 0.6 ml of hydrazine hydrate and the mixture was stirred overnight at room temperature. The solvent was evaporated and the residue was diluted with ethyl acetate. The white precipitate which formed was removed by filtration and the organic layer was washed with twice with 2M aqueous hydrogen chloride and once with saturated aqueous sodium chloride. Drying over anhydrous magnesium sulphate and evaporation gave 1.36 g of (E)-2'-(3-aminopropionyl)-2(R)-[1(S)-(tert-butoxycarbonyl)-4-phenyl-3-butenyl]-4-methylvalerohydrazide in the form of a solid.

MS: 432 (M+H)⁺.

(iii) In a manner analogous to that described in Example 1, parts (vi)–(viii), but using (E)-2'-[3-aminopropionyl]-2(R)-[1(S)-(tert-butoxycarbonyl)-4-phenyl-3-butenyl]-4-methylvalerohydrazide in place of (E)-2(R)-[1(S)-(tert-butoxycarbonyl)-4-phenyl-3-butenyl]-2'-glycinyl-4-methylvalerohydrazide, there was obtained (E)-N-(hexahydro-2,6-dioxo-1-pyrimidinyl)-2(R)-[1(S)-[(tetrahydro-2(RS)-pyranyloxy)carbamoyl- 4-phenyl-3-butenyl]-4-methylvaleramide in the form of a white solid.

MS: 501 (M+H)⁺.

EXAMPLE 3

2(R)-[4-Cyclohexyl-1(S)-(hydroxycarbamoyl)butyl]-4-methyl-N-(2,5-dioxo-1-imidazolidinyl)valeramide A solution of 0.280 g of 2(R)-[4-cyclohexyl-1(S)-[(tetrahydro-2(RS)-pyranyloxy)carbamoyl]butyl]-4-methyl-N-(2,5-dioxo-1-imidazolidinyl)valeramide in 10 ml of methanol was treated with 0.028 g of p-toluenesulphonic acid monohydrate. The mixture was stirred for 2 hours at room temperature and evaporated. The residue was dissolved in ethyl acetate, washed with 5% aqueous sodium hydrogen carbonate, dried over anhydrous magnesium sulphate and evaporated. The residue was purified by flash column chromatography on silica gel using methanol/dichloromethane (1:9) for the elution to give 0.069 g of 2(R)-[4-cyclohexyl-1(S)-(hydroxycarbamoyl)butyl]-4-methyl-N-(2,5-dioxo-1-imidazolidinyl)valeramide in the form of a white solid.

MS: 411 (M+H)+.

HPLC: Gradient elution using solvent A containing 5% solvent B increasing to 95% solvent B over 15 minutes; flow rate 1 ml/minute. Retention time: 11.44 minutes. Solvent A: $H_2O$/0.1% TFA; solvent B: $CH_3CN$/0.085% TFA. Column type: HYPBDSC18.

The 2(R)-[4-cyclohexyl-1(S)-[(tetrahydro-2(RS)-pyranyloxy)carbamoyl]butyl]-4-methyl-N-(2,5-dioxo-1-imidazolidinyl)valeramide used as the starting material was prepared as follows:

A solution of 0.240 g of (E)-2(R)-[1(S)-[(tetrahydro-2(RS)-pyranyloxy)carbamoyl-4-phenyl-3-butenyl]-4-methyl-N-(2,5-dioxo-1-imidazolidinyl)valeramide (prepared as described in Example 1) in 10 ml of acetic acid was hydrogenated for 2 hours in the presence of 0.075 g of platinum(IV) oxide. The catalyst was removed by filtration and the solvent was evaporated to give 0.280 g of crude 2(R)-[4-cyclohexyl-1(S)-[(tetrahydro-2(RS)-pyranyloxy)carbamoyl]butyl]-4-methyl-N-(2,5-dioxo-1-imidazolidinyl)valeramide in the form of a white solid.

MS: 495 (M+H)+.

EXAMPLE 4

(E)-N-(Tetrahydro-3-oxo-2H-1,2,4-thiadiazin-2-yl)-2(R)-[1(S)-(hydroxycarbamoyl)-4-phenyl-3-butenyl]-4-methylvaleramide S,S-dioxide In a manner analogous to that described in Example 2, but using 2-phthalimidoethanesulphonyl chloride in the place of 3-N-phthalimidopropionic acid, there was obtained 0.080 g of (E)-N-(tetrahydro-3-oxo-2H-1,2,4-thiadiazin-2-yl)-2(R)-[1(S)-(hydroxycarbamoyl)-4-phenyl-3-butenyl]-4-methylvaleramide S,S-dioxide in the form of a white solid.

MS: 453 (M+H)+.

HPLC: Gradient elution using solvent A containing 5% solvent B increasing to 95% solvent B over 15 minutes; flow rate 1 ml/minute. Retention time: 10.34 minutes. Solvent A: $H_2O$/0.1% TFA; solvent B: $CH_3CN$/0.085% TFA. Column type: HYPERSIL 5U BDS.

EXAMPLE 5

2(R)-[1(S)-(Hydroxycarbamoyl)-4-phenylbutyl]-4-methyl-N-(2,6-dioxo-1-piperazinyl)valeramide p-toluenesulphonate A solution of 0.072 g of 2(R)-[1(S)-[(tetrahydro-2(RS)-pyranyloxy)carbamoyl]-4-phenylbutyl]-4-methyl-N-(2,6-dioxo-1-piperazinyl)valeramide in a mixture of 5 ml of isopropyl alcohol and 1 ml of methanol was treated with 0.030 g of p-toluenesulphonic acid monohydrate at 0° C. The mixture was left to warm to room temperature and was stirred overnight. Evaporation and trituration of the residue with diethyl ether gave 0.059 g of 2(R)-[1(S)-(hydroxycarbamoyl)-4-phenylbutyl]-4-methyl-N-(2,6-dioxo-1-piperazinyl)valeramide p-toluenesulphonate in the form of an off-white solid.

MS: 419 (M+H)+.

HPLC: Gradient elution using solvent A containing 5% solvent B increasing to 95% solvent B over 15 minutes; flow rate 1 ml/minute. Retention time: 9.17 minutes. Solvent A: $H_2O$/0.1% TFA; solvent B: $CH_3CN$/0.085% TFA. Column type: HYPERPEP 300A.

The 2(R)-[1(S)-[(tetrahydro-2(RS)-pyranyloxy)carbamoyl]-4-phenylbutyl]-4-methyl-N-(2,6-dioxo-1-piperazinyl)valeramide used as the starting material was prepared as follows:

(i) A solution of 0.7 g of 2,6-dioxo-4-morpholine carboxylic acid benzyl ester in 20 ml of dichloromethane was treated with 1.0 g of (E)-2(R)-[1(S)-(tert-butoxycarbonyl)-4-phenyl-3-butenyl]-4-methylvalerohydrazide (prepared as described in Example 1). The mixture was stirred for 1 hour at room temperature and then treated with 0.53 g of 1-ethyl-3-(3-dimethylaminopropyl)carbodiimide hydrochloride. The mixture was stirred for a further 3 hours at room temperature and then washed in sequence with 2M aqueous hydrogen chloride, 5% aqueous sodium hydrogen carbonate and saturated aqueous sodium chloride. Drying of the organic phase over anhydrous magnesium sulphate and evaporation gave a residue which was purified by column chromatography on silica gel using ethyl acetate/ hexane (3:7) for the elution to give 1.16 g of 2(R)-[1(S)-(tert-butoxycarbonyl)-4-phenyl-3-butenyl]-4-methyl-N-(4-benzyloxycarbonyl-2,6-dioxo-1-piperazinyl)valeramide in the form of a white solid.

MS: 592 (M+H)+.

(ii) In a manner analogous to that described in Example 1, parts (vii)–(viii), but using 2(R)-[1(S)-(tert-butoxycarbonyl)-4-phenyl-3-butenyl]-4-methyl-N-(4-benzyloxycarbonyl-2,6-dioxo-1-piperazinyl)valeramide in the place of (E)-2(R)-[1(S)-(tert-butoxycarbonyl)-4-phenyl-3-butenyl]-4-methyl-N-(2,5-dioxo-1-imidazolidinyl) valeramide, there was obtained 2(R)-[1(S)-[(tetrahydro-2(RS)-pyranyloxy)carbamoyl]-4-phenyl-3-butenyl]-4-methyl-N-(4-benzyloxycarbonyl-2,6-dioxo-1-piperazinyl) valeramide in the form of a white solid.

MS: 635 (M+H)+.

(iii) A solution of 0.178 g of 2(R)-[1(S)-[(tetrahydro-2(RS)-pyranyloxy)carbamoyl]-4-phenyl-3-butenyl]-4-methyl-N-(4-benzyloxycarbonyl-2,6-dioxo-1-piperazinyl) valeramide in 5 ml of isopropyl alcohol was hydrogenated for 4 hours in the presence of 0.020 g of 10% palladium-on-carbon. The catalyst was removed by filtration and the solvent was evaporated to give 0.072 g of 2(R)-[1(S)-[(tetrahydro-2(RS)-pyranyloxy)carbamoyl]-4-phenylbutyl]-4-methyl-N-(2,6-dioxo-1-piperazinyl)valeramide in the form of a white solid.

MS: 503 (M+H)+.

EXAMPLE 6

2(R)-[1(S)-(Hydroxycarbamoyl)-4-phenylbutyl]-4-methyl-N-(2,4-dioxo-1,3-diazaspiro[4.5]decan-3-yl) valeramide In a manner analogous to that described in Example 3 from 0.25 g of 2(R)-[1(S)-[(tetrahydro-2(RS)-pyranyloxy)carbamoyl]-4-phenylbutyl]-4-methyl-N-(2,4-dioxo-1,3-diazaspiro[4.5]decan-3-yl)valeramide there was obtained 0.071 g of 2(R)-[1(S)-(hydroxycarbamoyl)-4-phenylbutyl]-4-methyl-N-(2,4-dioxo-1,3-diazaspiro[4.5]decan-3-yl) valeramide in the form of a white solid.

MS: 473 (M+H)+.

HPLC: Gradient elution using solvent A containing 5% solvent B increasing to 95% solvent B over 15 minutes; flow rate 1 ml/minute. Retention time: 10.05 minutes. Solvent A: H₂O/0.1% TFA; solvent B: CH₃CN/0.085% TFA. Column type: HYPERPEP 300 A.

The 2(R)-[1(S)-[(tetrahydro-2(RS)-pyranyloxy) carbamoyl-4-phenylbutyl]-4-methyl-N-(2,4-dioxo-1,3-diazaspiro[4.5]decan-3-yl)valeramide used as the starting material was prepared as follows:

(i) In an analogous manner to that described in Example 1 parts (vii) and (viii) starting from (E)-2(R)-[1(S)-tert.-butyoxycarbonyl)-4-phenyl-3-butenyl]-4-methylvalerohydrazide there was obtained (E)-2(R)-[1(S)-[(tetrahydro-2(RS)-pyranyloxy)carbamoyl]-4-phenyl-3-butenyl]-4-methylvalerohydrazide in the form of a white solid.

(ii) A solution of 0.269 g of 2-(trimethylsilyl)ethyl-1-isocyanato-1-cyclohexane carboxylate and 0.403 g of (E)-2(R)-[1(S)-[(tetrahydro-2(RS)-pyranyloxy)carbamoyl]-4-phenyl-3-butenyl]-4-methylvalerohydrazide in 6 ml of a 5:1 mixture of dichloromethane and dimethylformamide was treated with 0.15 ml of N-methylmorpholine and was stirred for 2 hours at room temperature. The solution was then washed with 5% citric acid solution and then saturated sodium chloride solution, dried over anhydrous magnesium sulphate and evaporated. The residue was purified by flash chromatography on silica gel using hexane/ethyl acetate (2:1) followed by hexane/ethyl acetate (1:1) for the elution. The product obtained was dissolved in 5 ml of tetrahydrofuran and 1.6 ml of a 1.0M solution of tetrabutylammonium fluoride in tetrahydrofuran added. The mixture was stirred for 1.5 hours at room temperature, then diluted with ethyl acetate and washed successively with 5% citric acid and brine, dried and evaporated. The residue was triturated with ether and there was obtained 0.25 g of (E)-2(R)-[1(S)-[(tetrahydro-2(RS)-pyranyloxy)carbamoyl]-4-phenyl-3-butenyl]-4-methyl-N-(2,4-dioxo-1,3-diazaspiro[4.5]decan-3-yl)valeramide in the form of a white solid.

MS: 555 (M+H)⁺.

(iii) A solution of 0.25 g of (E)-2(R(-[1(S)-[(tetrahydro-2(RS)pyranyloxy)carbamoyl]4-phenyl-3-butenyl]-4-methyl-N-(2,4-dioxo-1,3-diazaspiro[4.5]decan-3-yl) valeramide in 5 ml of methanol containing 0.025 g of 10% palladium-on-carbon catalyst was shaken in a hydrogen atmosphere for 2 hours. The catalyst was filtered off to give a solution of 0.25 g of 2(R)-[1(S)-[(tetrahydro-2(RS)-pyranyloxy)carbamoyl]-4-phenylbutyl]-4-methyl-N-(2,4-dioxo-1,3-diazaspiro[4.5]decan-3-yl)valeramide in methanol that was used directly in the process step.

MS: 557 (M+H)⁺.

EXAMPLE 7

2(R)-[1(S)-(Hydroxycarbamoyl)-4-phenylbutyl]-N-(4(S)-isopropyl-2,5-dioxo-1-imidazolidinyl)-4-methylvaleramide A mixture of 0.219 g of 2(R)-[1(S)-(benzyloxycarbamoyl)-4-phenylbutyl]-N-(4(S)-isopropyl-2,5-dioxo-1-imidazolidinyl)-4-methylvaleramide and 0.085 g of 10% palladium-on-charcoal catalyst in 5 ml of methanol was shaken in a hydrogen atmosphere for 2 hours. The catalyst was removed by filtration and the solvent evaporated. The residue was purified by flash chromatography using 3% methanol in dichloromethane for the elution. There was obtained 0.064 g of 2(R)-[1(S)-(hydroxycarbamoyl)-4-phenylbutyl]-N-(4(S)-isopropyl-2,5-dioxo-1-imidazolidinyl)-4-methylvaleramide in the form of a white solid.

MS: 447 (M+H)⁺.

HPLC: Gradient elution using solvent A containing 5% solvent B increasing to 95% solvent B over 15 minutes; flow rate 1 ml/minute. Retention time: 9.31 minutes. Solvent A: H₂O/0/1% TFA; solvent B: CH₃CN/0.085% TFA. Column type: HYPERPEP 300A.

The 2(R)-[1(S)-(benzyloxycarbamoyl)-4-phenylbutyl]-N-(4(S)-isopropyl-2,5-dioxo-1-imidazolidinyl)-4-methylvaleramide used as the starting material was prepared as follows:

(i) A solution of 19 g of (E)-2(R)-[1(S)-(tert-butoxycarbonyl)-4-phenyl-3-butenyl]-4-methylvaleric acid in 220 ml of dimethylformamide was cooled to 0° C. and was treated in succession with 9.22 g of benzyl carbamate, 8.43 g of 1-hydroxybenzotriazole, 7.05 ml of N-methylmorpholine and 11.7 g of 1-ethyl-3-(3-dimethylaminopropyl)carbodiimide. The mixture was allowed to warm to room temperature and was then stirred overnight. The solvent was evaporated and the residue was partitioned between ethyl acetate and 5% aqueous citric acid solution. The ethyl acetate layer was washed with 5% sodium hydrogen carbonate and saturated sodium chloride solution. After drying over anhydrous magnesium sulphate the ethyl acetate was evaporated and the residue dissolved 200 ml of methanol and 2.5 g of 10% palladium-on-charcoal added. The mixture was shaken in a hydrogen atmosphere for 4 hours and then the catalyst was removed by filtration. The methanol was evaporated and the residue stirred with hexane and filtered. There was obtained 17.41 g of 2(R)-[1(S)-(tert-butoxycarbonyl)-4-phenylbutyl]-4-methylvalerohydrazide in the form of a white solid.

MS: 362 (M+H)⁺.

(ii) A solution of 0.517 g of 2(R)-[1(S)-(tert-butoxycarbonyl)-4-phenylbutyl]-4-methylvalerohydrazide in 5 ml of dichloromethane was treated with 0.302 g of methyl (S)-(+)-2-isocyanato-3-methylbutyrate and 0.3 ml of N-ethylmorpholine. The mixture was stirred at room temperature for 4 hours and then the solution was washed with 5% aqueous citric acid solution, saturated sodium chloride solution, dried over anhydrous magnesium sulphate and evaporated. The residue was dissolved in 5 ml of toluene containing 0.2 ml of triethylamine. The mixture was heated at reflux for 24 hours. The solution was cooled, diluted with ethyl acetate and washed with 5% aqueous citric acid solution, saturated sodium chloride solution, dried over anhydrous magnesium sulphate, and evaporated. The residue was triturated with ether and there was obtained 0.468 g of 2(R)-[1(S)-(tert-butoxycarbonyl)-4-phenylbutyl]-N-(4(S)-isopropyl-2,5-dioxo-1-imidazolidinyl)-4-methylvaleramide in the form of a white solid.

MS: 510 (M+H)⁺.

(iii) In a manner analogous to that described in Example 1, parts (vii) and (viii), but using O-benzylhydroxylamine in place of O-(tetrahydro-2H-pyran-2(RS)-yl)hydroxylamine there was obtained, from 0.468 g of 2(R)-[1(S)-(tert-butoxycarbonyl)-4-phenylbutyl]-N-(4(S)-isopropyl-2,5-dioxo-1-imidazolidinyl)-4-methylvaleramide there was obtained 0.219 g of 2(R)-[1(S)-(benzyloxycarbamoyl)-4-phenylbutyl]-N-(4(S)-isopropyl-2,5-dioxo-1-imidazolidinyl)-4-methylvaleramide in the form of a white solid.

MS: 537 (M+H)⁺.

EXAMPLE 8

2(R)-[1(S)-(Hydroxycarbamoyl)-4-phenylbutyl]-4-methyl-N-(6,8-dioxo-5,7-diazaspiro[3,4]oct-7-yl) valeramide In a manner analogous to that described in Example 7 from 0.143 g of 2(R)-[1(S)-benzyloxycarbamoyl)-4- phenylbutyl]-4-methyl-N-(6,8-dioxo-5,7-diazaspiro[3.4] oct-7-yl)valeramide there was obtained, after purification of the product by trituration with ether, 0.088 g of 2(R)-[1(S)-(hydroxycarbamoyl)-4-phenylbutyl]-4-methyl-N-(6,8-dioxo-5,7-diazaspiro[3.4]oct-7-yl)valeramide in the form of a white solid.

MS: 445 (M+H)$^+$.

HPLC: Gradient elution using solvent A containing 5% solvent B increasing to 95% solvent B over 15 minutes; flow rate 1 ml/minute. Retention time: 8.90 minutes. Solvent A: H$_2$O/0.1% TFA; solvent B: CH$_3$CN/0.085% TFA. Column type: HYPERPEP 300A.

The 2(R)-[1(S)-(benzyloxycarbamoyl)-4-phenylbutyl]-4-methyl-N-(6,8-dioxo-5,7-diazaspiro[3.4]oct-7-yl) valeramide used as the starting material was prepared in a manner analogous to that described in Example 7, parts (ii) and (iii) starting from 2(R)-[1(S)-(tert-butoxycarbonyl)-4-phenylbutyl]-4-methylvalerohydrazide and ethyl 1-isocyanato-1-cyclobutane carboxylate.

MS: 535 (M+H)$^+$.

EXAMPLE 9

2(R)-[1(S)-(Hydroxycarbamoyl)-4-phenylbutyl]-4-methyl-N-(5-oxo-2-thioxo-1-imidazolidinyl) valeramide In a manner analogous to that described in Example 3 from 0.09 g of 2(R)-[1(S)-[(tetrahydro-2(RS)-pyranyloxy) carbamoyl]-4-phenylbutyl]-4-methyl-N-(5-oxo-2-thioxo-1-imidazolidinyl)valeramide there was obtained 0.03 g of 2(R)-[1(S)-(hydroxycarbamoyl)-4-phenylbutyl]-4-methyl-N-(5-oxo-2-thioxo-1-imidazolidinyl)valeramide in the form of a yellow solid.

MS: 421 (M+H)$^+$.

HPLC: Gradient elution using solvent A containing 5% solvent B increasing to 95% solvent B over 15 minutes; flow rate 1 ml/minute. Retention time: 8.44 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl-4-methyl-N-oxo-2-thioxo-1-imidazolidinyl)valeramide used as the starting material was prepared in a manner analogous to that described in Example 7, part (ii) and Example 1, parts (vii) and (viii), starting from 2(R)-[1(S)-tert-butoxycarbonyl)-4-phenylbutyl]-4-methylvalerohydrazide and methyl 2-isothiocyanatoacetate.

MS: 505 (M+H)$^+$.

EXAMPLE 10

N-(4(S)-Benzyl -2,5-dioxo-1-imidazolidinyl)-2R-[1 (S)-(hydroxycarbamoyl)-4-phenylbutyl]-4-methylvaleramide In a manner analogous to that described in Example 3 from 0.491 g of N-(4(S)-benzyl-2,5-dioxo-1-imidazolidinyl)-2R-[1(S)-[(tetrahydro-2(RS)-pyranyloxy) carbamoyl]-4-phenylbutyl]-4-methylvaleramide there was obtained 0.208 g of 4-(4(S)-benzyl-2,5-dioxo-1-imidazolidinyl)-2R-[1(S)-(hydroxycarbamoyl)-4-phenylbutyl]-4-methylvalermide in the form of an off-white solid.

MS: 495 M+H)$^+$.

HPLC: Gradient elution using solvent A containing 5% solvent B increasing to 95% solvent B over 15 minutes; flow rate 1 ml/minute. Retention time: 10.14 minutes. Solvent A: H$_2$O/0.1% TFA; solvent B: CH$_3$CN/0.085% TFA. Column type: HYPERPEP 300A.

The N-(4(S)-benzyl-2,5-dioxo-1-imidazolidinyl)-2R-[1 (S)-[(tetrahydro-2(RS)-pyranyloxy)carbamoyl]-4-phenylbutyl]-4-methylvaleramide used as the starting material was prepared in a manner analogous to that described in Example 7, part (ii) and Example 1, parts (vii) and viii), starting from 2(R)-[1(S)-(tert-butoxycarbonyl)-4-phenylbutyl]-4-methylvalerohydrazide and methyl (S)-2-isocyanato-3-phenylpropionate.

MS: 579 (M+H)$^+$.

EXAMPLE 11

2(R)-[1(S)-(Hydroxycarbamoyl)-4-phenylbutyl]-4-methyl-N-[4(S)-(1(S)-methylpropyl)-2,5-dioxo-1-imidazolidinylvaleramide In a manner analogous to that described in Example 3 from 0.306 g of 2(R)-[1(S)-[(tetrahydro-2(RS)-pyranyloxy) carbamoyl]-4-phenylbutyl]-4-methyl-N-[4(S)-(1(S)-methylpropyl)-2,5-dioxo-1-imidazolidinylvaleramide there was obtained 0.073 g of 2(R)-[1(S)-(hydroxycarbamoyl)-4-phenylbutyl]-4-methyl-N-[4(S)-(1(S)-methylpropyl)-2,5-dioxo-1-imidazolidinylvaleramide in the form of a white solid.

MS: 461 (M+H)$^+$.

HPLC: Gradient elution using solvent A containing 5% solvent B increasing to 95% solvent B over 15 minutes; flow rate 1 ml/minute. Retention time: 9.90 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl]-4-methyl-N-[4(S)-(1(S)-methylpropyl)-2,5-dioxo-1-imdiazolidinylvaleramide used as the starting material was prepared in a manner analogous to that described in Example 7, part (ii) and Example 1, parts (vii) and (viii), starting from 2(R)-[1(S)-(tert-butoxycarbonyl)-4-phenylbutyl]-4-methylvalerohydrazide and methyl(2S,3S)-2-isocyanato-3-methylvalerate.

MS: 545 (M+H)$^+$.

EXAMPLE 12

2(R)-[1(S)-(Hydroxycarbamoyl)-4-phenylbutyl]-4-methyl-N-[4(S)-[2-(methylthio)ethyl]-2,5-dioxo-1-imidazolidinyl]valeramide In a manner analogous to that described in Example 3 from 0.461 g of 2(R)-[1(S)-[(tetrahydro-2(RS)-pyranyloxy) carbamoyl]-4-phenylbutyl]-4-methyl-N-[4(S)-[2-(methylthio)ethyl]-2,5-dioxo-1-imidazolidinyl]valeramide there was obtained 0.084 g of 2(R)-[1(S)-(hydroxycarbamoyl)-4-phenylbutyl]-4-methyl-N-[4(S)-[2-(methylthio)ethyl]-2,5-dioxo-1-imidazolidinyl]valeramide in the form of a pale orange solid.

MS: 479 (M+H)$^+$.

HPLC: Gradient elution using solvent A containing 5% solvent B increasing to 95% solvent B over 15 minutes; flow rate 1 ml/minute. Retention time: 9.38 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl]-4-methyl-N-[4(S)-[2-(methylthio)ethyl]-2,5-dioxo-1-imidazolidinyl]valeramide used as the starting material was prepared in a manner analogous to that described in Example 7, part (ii) and Example 1, parts (vii) and (viii), starting from 2(R)-[1(S)-(tert-butoxycarbonyl)-4-phenylbutyl]-4-methylvalerohydrazide and methyl(S)-(−)-2-isocyanato-4-(methylthio)butyrate.

MS: 563 (M+H)$^+$.

EXAMPLE 13

2(R)-[1(S)-(Hydroxycarbamoyl)-4-phenylbutyl]-4-methyl-N-(4,4-dimethyl-2,5-dioxo-1-imidazolidinyl) valeramide In a manner analogous to that described in Example 3 from 0.285 g of 2(R)-[1(S)-[(tetrahydro-2(RS)-pyranyloxy) carbamoyl]-4-phenylbutyl]-4-methyl-N-(4,4-dimethyl-2,5-dioxo-1-imidazolidinyl)valeramide there was obtained 0.091 g of 2(R)-[(S)-(hydroxycarbamoyl)-4-phenylbutyl]-4-methyl-N-(4,4-dimethyl-2,5-dioxo-1-imidazolidinyl) valeramide in the form of an off-white solid

MS: 433 (M+H)$^+$.

HPLC: Gradient elution using solvent A containing 5% solvent B increasing to 95% solvent B over 15 minutes; flow rate 1 ml/minute. Retention time: 8.67 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl]-4-methyl-N-(4,4-dimethyl-2,5-dioxo-1-imidazolidinyl)valeramide used as the starting material was prepared in a manner analogous to that described in Example 7, part (ii) and Example 1, parts (vii) and (viii), starting from 2(R)-[1(S)-(tert-butoxycarbonyl)-4-phenylbutyl]-4-methylvalerohydrazide and ethyl 2-isocyanato-2-methylpropionate.

MS: 517.

EXAMPLE 14

2(R)-[1(S)-Hydroxycarbamoyl)-4-phenylbutyl]-N-(4 (R)-isopropyl-2,5-dioxo-1-imidazolidinyl)-4-methylvaleramide In a manner analogous to that described in Example 3 from 0.316 mg of 2(R)-[1(S)-[(tetrahydro-2(RS)-pyranyloxy)carbamoyl]-4-phenylbutyl]-N-(4(R)-isopropyl-2,5-dioxo-1-imidazolidinyl)-4-methylvaleramide there was obtained 0.059 g of 2(R)-[1(S)-(hydroxycarbamoyl)-4-phenylbutyl]-N-(4(R)-isopropyl-2,5-dioxo-1-imidazolidinyl)-4-methylvaleramide in the form of an off-white solid.

MS: 447 (M+H)$^+$.

HPLC: Gradient elution using solvent A containing 5% solvent B increasing to 95% solvent B over 15 minutes; flow rate 1 ml/minute. Retention time: 9.27 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl]-N-(4(R)-isopropyl-2,5-dioxo-1-imidazolidinyl)-4-methylvaleramide used as the starting material was prepared in a manner analogous to that described in Example 7, part (ii) and Example 1, parts (vii) and (viii), starting from 2(R)-[1(S)-(tert-butoxycarbonyl)-4-phenylbutyl]-4-methylvalerohydrazide and methyl (R)-(−)-2-isocyanato-3-methylbutyrate.

MS: 531 (M+H)$^+$.

EXAMPLE 15

2(R)-[1(S)-(Hydroxycarbamoyl)-4-phenylbutyl]-N-[4(S)-(hydroxymethyl)-2,5-dioxo-1-imidazolidinyl]-4-methylvaleramide In a manner analogous to that described in Example 3 from 0.435 g of 2(R)-[1(S)-[(tetrahydro-2(RS)-pyranyloxy) carbamoyl]-4-phenylbutyl]-N-[4(S)-(hydroxymethyl)-2,5-dioxo-1-imidazolidinyl]-4-methylvaleramide there was obtained 0.20 g of 2(R)-[1(S)-(hydroxycarbamoyl)-4-phenylbutyl]-N-[4(S)-(hydroxymethyl)-2,5-dioxo-1-imidazolidinyl]-4-methylvaleramide in the form of a white solid.

MS: 435 (M+H)$^+$.

HPLC: Gradient elution using solvent A containing 5% solvent B increasing to 95% solvent B over 15 minutes; flow rate 1 ml/minute. Retention time: 7.53 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl]-N-[4(S)-(hydroxymethyl)-2,5-dioxo-1-imidazolidinyl]-4-methylvaleramide used as the starting material was prepared in a manner analogous to that described in Example 7, part (ii) and Example 1, parts (vii) and (viii), starting from 2(R)-[1(S)-(tert-butoxycarbonyl)-4-phenylbutyl]-4-methylvalerohydrazide and methyl(S)-(+)-2-isocyanato-3-tert.-butoxypropionate.

MS: 519 (M+H)$^+$.

EXAMPLE 16

2(R)-[1(S)-(Hydroxycarbamoyl)-4-phenylbutyl]-N-(4(S)-isopropyl-5-oxo-2-thioxo-1-imidazolidinyl)-4-methylvaleramide In a manner analogous to that described in Example 3 from 0.484 g of 2(R)-[1(S)-[(tetrahydro-2(RS)-pyranyloxy) carbamoyl]-4-phenylbutyl]-N-(4(S)-isopropyl-5-oxo-2-thioxo-1-imidazolidinyl)-4-methylvaleramide there was obtained 0.254 g of 2(R)-[1(S)-(hydroxycarbamoyl)-4-phenylbutyl]-N-(4(S)-isopropyl-5-oxo-2-thioxo-1-imidazolidinyl)-4-methylvaleramide in the form of a white solid.

MS: 463 (M+H)$^+$.

HPLC: Gradient elution using solvent A containing 5% solvent B increasing to 95% solvent B over 15 minutes; flow rate 1 ml/minute. Retention time: 9.83 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl]-N-(4(S)-isopropyl-5-oxo-2-thioxo-1-imidazolidinyl)-4-methylvaleramide used as the starting material was prepared in a manner analogous to that described in Example 7, part (ii) and Example 1, parts (vii) and (viii), starting from 2(R)-[1(S)-(tert-butoxycarbonyl)-4-phenylbutyl]-4-methylvalerohydrazide and methyl L-2-isothiocyanato-3-methylbutyrate.

MS: 547 (M+H)$^+$.

EXAMPLE 17

2(R)-[1(S)-(Hydroxycarbamoyl)-4-phenylbutyl]-N-(4(S)-isobutyl-2,5-dioxo-1-imidazolidinyl)-4-metylvaleramide In a manner analogous to that described in Example 3 from 0.303 g pf 2(R)-[1(S)-[(tetrahydro-2(RS)-pyranyloxy) carbamoyl]-4-phenylbutyl]-N-(4(S)-isobutyl-2,5-dioxo-1-imidazolidinyl)-4-methylvaleramide there was obtained 0.112 g of 2(R)[1(S)-(hydroxycarbamoyl)-4-phenylbutyl]-N-(4(S)-isobutyl-2,5-dioxo-1-imidazolidinyl)-4-methylvaleramide in the form of a white solid.

MS: 461 (M+H)$^+$.

HPLC: Gradient elution using solvent A containing 5% solvent B increasing to 95% solvent B over 15 minutes; flow rate I ml/minute. Retention time: 10.07 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl]-N-(4(S)-isobutyl-2,5-dioxo-1-imidazolidinyl)-4-methylvaleramide used as the starting material was prepared in a manner analogous to that described in Example 7, part (ii) and Example 1, parts (vii) and (viii), starting from 2(R)-[1(S)-(tert.butoxycarbonyl)-4-phenylbutyl]-4-methylvalerohydrazide and methyl (S)-(−)-2-isocyanato-4-methylvalerate.

MS: 545 (M+H)$^+$.

EXAMPLE 18

2(R)-[1(S)-(Hydroxycarbamoyl)-4-phenylbutyl]-N-(4(S)-isobutyl-5-oxo-2-thioxo-1-imidazolidinyl)-4-methylvaleramide In a manner analogous to that described in Example 3 from 0.415 g of 2(R)-[1(S)-[(tetrahydro-2(RS)-pyranyloxy) carbamoyl]-4-phenylbutyl]-N-(4(S)-isobutyl-5-oxo-2-thioxo-1-imidazolidinyl)-4-methylvaleramide there was obtained 0.192 g of 2(R)-[1(S)-(hydroxycarbamoyl)-4-phenylbutyl]-N-(4(S)-isobutyl-5-oxo-2-thioxo-1-imidazolidinyl)-4-methylvaleramide in the form of a white solid.

MS: 477 (M+H)$^+$.

HPLC: Gradient elution using solvent A containing 5% solvent B increasing to 95% solvent B over 15 minutes; flow rate 1 ml/minute. Retention time: 10.67 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl]-N-(4(S)-isobutyl-5-oxo-2-thioxo-1-imidazolidinyl)-4-methylvaleramide used as the starting material was prepared in a manner analogous to that described in Example 7, part (ii) and Example 1, parts (vii) and (viii), starting from 2(R)-[1(S)-tert-butoxycarbonyl)-4-phenylbutyl]-4-methylvalerohydrazide and methyl L-2-isothiocyanato-4-methylvalerate.

MS: 561 (M+H)$^+$.

EXAMPLE 19

1-[2(R)-[1(S)-(Hydroxycarbamoyl)-4-phenylbutyl]-4-methylvaleramide]-2,5-dioxo-4(S)-imidazolidinepropionate In a manner analogous to that described in Example 3 from 0.563 g of 1-[2(R)-[1(S)-[(tetrahydro-2(RS)-pyranyloxy)carbamoyl]-4-phenylbutyl]-4-methylvaleramide-2,5-dioxo-4(S)-imidazolidinepropionate there was obtained 0.190 g of 1-[2(R)-[1(S)-(hydroxycarbamoyl)-4-phenylbutyl]-4-methylvaleramide-2,5-dioxo-4(S)-imidazolidinepropionate in the form of an off-white foam.

MS: 505 (M+H)$^+$.

HPLC: Gradient elution using solvent A containing 5% solvent B increasing to 95% solvent B over 15 minutes; flow rate 1 ml/minute. Retention time: 9.40 minutes. Solvent A: H$_2$O/0.1% TFA; solvent B: CH$_3$CN/0.085% TFA. Column type: HYPERPEP 300A.

The 1-[2(R)-[1(S)-[(tetrahydro-2(RS)-pyranyloxy) carbamoyl]-4-phenylbutyl]-4-methylvaleramide used as the starting material was prepared in a manner analogous to that described in Example 7, part (ii) and Example 1, parts (vii) and (viii), starting from 2(R)-[1(S)-(tert-butoxycarbonyl)-4-phenylbutyl]-4-methylvalerohydrazide and diethyl (S)-(−)-(2)-isocyanatoglutarate.

MS: 589 (M+H)$^+$.

EXAMPLE 20

(E)-2(R)-[1(S)-(Hydroxycarbamoyl)-4-phenyl-3-butenyl]-N-[4(S)-(1(S)-methylpropyl)-2,5-dioxo-1-imidazolidinyl]-4-methylvaleramide In a manner analogous to that described in Example 3 from 0.649 g of (E)-2(R)-[1(S)-[(tetrahydro-2(RS)-pyranyloxy)carbamoyl]-4-phenyl-3-butenyl]-N-[4(S)-(1(S)-methylpropyl)-2,5-dioxo-1-imidazolidinyl]-4-methylvaleramide there was obtained 0.171 g of (E)-2(R)-[1(S)-(hydroxycarbamoyl)-4-phenyl-3-butenyl]-N-[4(S)-(1(S)-methylpropyl)-2,5-dioxo-1-imidazolidinyl]-4-methylvaleramide in the form of a white solid.

MS: 459 (M+H)$^+$.

HPLC: Gradient elution using solvent A containing 5% solvent B increasing to 95% solvent B over 15 minutes; flow rate 1 ml/minute. Retention time: 9.96 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl-N-[4(S)-(1(S)-methylpropyl)-2,5-dioxo-1-imidazolidinyl]-4-methylvaleramide used as the starting material was prepared in a manner analogous to that described in Example 7, part (ii) and Example 1, parts (vii) and (viii), starting from (E)-2(R)-[1(S)-(tert-butoxycarbonyl)-4-phenyl-3-butenyl]-4-methylvalerohydrazide and methyl (2S,3S)-2-isocyanato-3-methylvalerate.

MS: 543 (M+H)$^+$.

EXAMPLE 21

(E)-2(R)-[1(S)-(Hydroxycarbamoyl)-4-phenyl-3-butenyl]-N-[4(S)-(hydroxymethyl)-2,5-dioxo-1-imidazolidinyl]-4-methylvaleramide In a manner analogous to that described in Example 3 from 0.2 g of (E)-2(R)-[1(S)-[(tetrahydro-2(RS)-pyranyloxy)carbamoyl]-4-phenyl-3-butenyl]-N-[4(S)-(hydroxymethyl)-2,5-dioxo-1-imidazolidinyl]-4-methylvaleramide there was obtained 0.083 g of (E)-2(R)-[1(S)-(hydroxycarbamoyl)-4-phenyl-3-butenyl]-N-[4(S)-(hydroxymethyl)-2,5-dioxo-1-imidazolidinyl]-4-methylvaleramide in the form of a white solid.

MS: 433 (M+H)$^+$.

HPLC: Gradient elution using solvent A containing 5% solvent B increasing to 95% solvent B over 15 minutes; flow rate 1 ml/minute. Retention time: 9.41 minutes. Solvent A: H$_2$O/0.1% TFA; solvent B: CH$_3$CN/0.085% TFA. Column type: HYPERPEP 300A.

The (E)-2(R)-[1(S)-[(tetrahydro-2(RS)-pyranyloxy) carbamoyl]-4-phenyl-3-butenyl]-N-[4(S)-(hydroxymethyl)-2,5-dioxo-1-imidazolidinyl]-4-methylvaleramide used as the starting material was prepared in a manner analogous to that described in Example 7, part (ii) and Example 1, parts (vii) and (viii), starting from (E)-2(R)-[1(S)-(tert-butoxycarbonyl)-4-phenyl-3-butenyl]-4-methylvalerohydrazide and methyl (S)-(+)-2-isocyanato-3-tert.-butoxypropionate.

MS: 517 (M+H)$^+$.

EXAMPLE 22

Ethyl 3-[2(R)-[1(S)-(hydroxycarbamoyl)-4-phenylbutyl]-4-methylvaleramido]-2,4-dioxo-1,3,8-triazaspiro[4.5]decane-8-carboxylate In a manner analogous to that described in Example 7 for 0.348 g of ethyl 3-[2(R)-[1(S)-(benzyloxycarbamoyl)-4- phenylbutyl]-4-methylvaleramido]-2,4-dioxo-1,3,8-triazaspiro[4.5]decane-8-carboxylate there was obtained 0.248 g of ethyl 3-[2(R)-[1(S)-(hydroxycarbamoyl)-4-phenylbutyl]-4-methylvaleramide]-2,4-dioxo-1,3,8-triazaspiro[4.5]decane-8-carboxylate in the form of an off-white solid.

MS: 546 $(M+H)^+$.

HPLC: Gradient elution using solvent A containing 5% solvent B increasing to 95% solvent B over 15 minutes; flow rate 1 ml/minute. Retention time: 9.56 minutes. Solvent A: $H_2O$/0.1% TFA; solvent B: $CH_3CN$/0.085% TFA. Column type: HYPERPEP 300A.

The ethyl 3-[2(R)-[1(S)-(benzyloxycarbamoyl)-4-phenylbutyl]-4-methylvaleramide]-2,4-dioxo-1,3,8-triazaspiro[4,5]decane-8-carboxylate used as the starting material was prepared as follows:

(i) A solution of 3.68 g of 1,4,4-tricarbethoxypiperidine (prepared by the method of S. Huybrechts and G. J. Hoornaert, Synthetic Communications, 11(1), 17–23 (1981)) in 5 ml of ethanol was treated with a solution of 0.499 g of sodium hydroxide in 2.5 ml of water. The mixture was stirred overnight at room temperature and the ethanol evaporated. The aqueous residue was extracted with two portions of diethyl ether and was then acidified by dropwise addition of concentrated hydrochloric acid. The acidified aqueous residue was extracted with four portions of diethyl ether and the combined extracts washed with three portions of saturated sodium chloride solution and dried over anhydrous magnesium sulphate. After evaporation of the diethyl ether there was obtained 2.50 g of 1,4-dicarbethoxypiperidine-1-carboxylic acid in the form of an oil.

MS: 274 $(M+H)^+$.

(ii) A solution of 1.25 g of 1,4-dicarbethoxypiperidine-4-carboxylic acid in 10 ml of dry tetrahydrofuran was cooled to ice temperature and was treated with 0.7 ml of N-ethylmorpholine then 0.7 ml of isobutyl chloroformate. The mixture was stirred at ice temperature for 20 minutes and then a solution of 0.59 g of sodium azide in 7 ml of water added. The mixture was stirred at ice temperature for 15 minutes and then at room temperature for a further 30 minutes. The mixture was then shaken with 20 ml of toluene and the toluene extract washed with a further portion of water and then with saturated sodium chloride solution. After drying over anhydrous magnesium sulphate the toluene solution was reduced to approximately half its volume and then heated at 100° C. for 1 hour. The toluene was evaporated and there was obtained 1.148 g of 1,4-dicarbethoxy-4-isocyanatopiperidine in the form of an oil.

MS: 271 $(M+H)^+$.

(iii) In a manner analogous to that described in Example 7, parts (ii) and (iii) starting from 2(R)-[1(S)-tert-butoxycarbonyl)-4-phenylbutyl]-4-methylvalerohydrazide and 1,4-dicarbethoxy-4-isocyanatopiperidine there was obtained ethyl 3-[2-(R)-[1(S)-(benzyloxycarbamoyl)-4-phenylbutyl]-4-methylvaleramide]-2,4-dioxo-1,3,8-triazaspiro[4.5]decane-8-carboxylate in the form of a white solid.

MS: 636 $(M+H)^+$.

EXAMPLE 23

Benzyl 3-[2(R)-[1(S)-(hydroxycarbamoyl)-4-phenylbutyl]-4-methylvaleramido]-2,4-dioxo-1,3,8-triazaspiro[4,5]decane-8-carboxylate In a manner analogous to that described in Example 3 from 0.103 g of benzyl 3-[2(R)-[1(S)-[(tetrahydro-2(RS)-pyranyloxy)carbamoyl]-4-phenylbutyl]-4-methylvaleramido]-2,4-dioxo-1,3,8-triazaspiro[4.5]decane-8-carboxylate there was obtained 0.078 g of benzyl 3-[2(R)-[1(S)-(hydroxycarbamoyl)-4-phenylbutyl]-4-methylvaleramido]-2,4-dioxo-1,3,8-triazaspiro[4.5]decane-8-carboxylate in the form of a white solid.

MS: 608 $(M+H)^+$.

HPLC: Gradient elution using solvent A containing 5% solvent B increasing to 95% solvent B over 15 minutes; flow rate 1 ml/minute. Retention time: 10.95 minutes. Solvent A: $H_2O$/0.1% TFA; solvent B: $CH_3CN$/0.085% TFA. Column type: HYPERPEP 300A.

The benzyl 3-[2(R)-[1(S)-[(tetrahydro-2(RS)-pyranyloxy)carbamoyl]-4-phenylbutyl]-4-methylvaleramido]-2,4-dioxo-1,3,8-triazaspiro[4.5]decane-8-carboxylate used as the starting material was prepared as follows:

(i) In a manner analogous to that described by S. Huybrechts and G. J. Hoornaert, Synthetic Communications, 11 (1), 17–23 (1981) for the preparation of 1,4,4-tricarbethoxypiperidine but using benzyl chloroformate in place of ethyl chloroformate there was obtained benzyl 4,4-dicarbethoxypiperidine-1-carboxylate in the form of an oil.

MS: 364 $(M+H)^+$.

(ii) In a manner analogous to that described in Example 22, parts (i) and (ii) from benzyl 4,4-dicarbethoxypiperidine-1-carboxylate there was obtained benzyl 4-carbethoxy-4-isocyanatopiperidine-1-carboxylate in the form of an oil.

MS: 332 $(M)^+$; IR: 2256 (isocyanate).

(iii) In a manner analogous to that described in Example 6, part (ii) starting from 2(R)-[1(S)-[(tert-butoxycarbonyl)-4-phenylbutyl]-4-methylvalerohydrazide and benzyl 4-carbethoxy-4-isocyanatopiperidine-1-carboxylate there was obtained benzyl 3-[2(R)-[1(S)-(tert-butoxycarbonyl)-4-phenylbutyl]-4-methylvaleramido]-2,4-dioxo-1,3,8-triazaspiro[4.5]decane-8-carboxylate in the form of a white solid.

MS: 649 $(M+H)^+$.

(iv) In a manner analogous to that described in Example 1, parts (vii) and (viii) starting from benzyl 3-[2(R)-[1(S)-(tert-butoxycarbonyl)-4-phenylbutyl]-4-methylvaleramido]-2,4-dioxo-1,3,8-triazaspiro[4.5]decane-8-carboxylate there was obtained benzyl 3-[2(R)-[1(S)-[(tetrahydro-2(RS)-pyranyloxy)carbamoyl]-4-phenylbutyl]-4-methylvaleramido]-2,4-dioxo-1,3,8-triazaspiro[4.5]decane-8-carboxylate in the form of a white solid.

MS: 692 $(M+H)^+$.

EXAMPLE 24

N-[8-(Aminoacetyl)-2,4-dioxo-1,3,8-triazaspiro[4.5]decan-3-yl)-2(R)-[1(S)-(hydroxycarbamoyl)-4-phenylbutyl]-3-methylvaleramide In a manner analogous to that described in Example 7 from 0.101 g of N-[8-[N-(benzyloxycarbonyl)aminoacetyl]-2,4-dioxo-1,3,8-triazaspiro[4.5]decan-3-yl)-2(R)-[1(S)-(benzyloxycarbamoyl)-4-phenylbutyl]-3-methylvaleramide there was obtained 0.048 g of N-[8-(aminoacetyl)-2,4-dioxo-1,3,8-triazaspiro[4.5]decan-3-yl)-2(R)-[1(S)-(hydroxycarbamoyl)-4-phenylbutyl]-3-methylvaleramide in the form of a white solid.

MS: 531 $(M+H)^+$.

HPLC: Gradient elution using solvent A containing 5% solvent B increasing to 95% solvent B over 15 minutes; flow rate 1 ml/minute. Retention time: 7.34 minutes. Solvent A: H$_2$O/0.1% TFA; solvent B: CH$_3$CN/0.085% TFA. Column type: HYPERPEP 300A.

The N-[8-[(N-benzyloxycarbonyl)aminoacetyl]-2,4-dioxo-1,3,8-triazaspiro[4.5]decan-3-yl)-2(R)-[(S)-(benzyloxycarbamoyl)-4-phenylbutyl]-3-methylvaleramide used as the starting material was prepared as follows:

(i) A solution of 1.01 g of benzyl 3-[2(R)-[1(S)-(tert-butoxycarbonyl)-4-phenylbutyl]-4-methylvaleramido]-2,4-dioxo-1,3,8-triazaspiro[4.5]decane-8-carboxylate in 15 ml of methanol was treated with 0.432 g of 10% palladium-on-charcoal catalyst. The mixture was shaken in a hydrogen atmosphere for 18 hours. The catalyst was filtered off and the methanol evaporated. The residue was triturated with ether and there was obtained 0.81 g of 2(R)-[1(S)-(tert-butoxycarbonyl)-4-phenylbutyl]-4-methyl-N-[2,4-dioxo-1,3,8-triazaspiro[4.5]decan-3-yl]valeramide in the form of a white solid.

MS: 515 (M+H)$^+$.

(ii) A mixture of 0.257 g of 2(R)-[1(S)-(tert-butoxycarbonyl)-4-phenylbutyl]-4-methyl-N-[2,4-dioxo-1,3,8-triazaspiro[4.5]decan-3-yl]valeramide and 0.209 g of N-(benzyloxycarbonyl)glycine in 5 ml of dry dimethylformamide was stirred and cooled to ice temperature. The mixture was treated with 0.225 g of 1-ethyl-3-(3-dimethylaminopropyl)carbodiimide hydrochloride and was then stirred at room temperature for 2 days. The solvent was evaporated and the residue partitioned between water and ethyl acetate. The ethyl acetate layer was washed successively with water, 5% aqueous sodium bicarbonate solution, saturated sodium chloride solution and dried over anhydrous magnesium sulphate. The solvent was evaporated and the residue triturated with ether and there was obtained 0.261 g of N-[8-{N-(benzyloxycarbonyl)aminoacetyl]-2(R)-[1(S)-(tert-butoxycarbonyl)-4-phenylbutyl]-4-methyl-N-[2,4-dioxo-1,3,8-triazaspiro[4.5]decan-3-yl]valeramide in the form of a white solid.

MS: 706 (M+H)$^+$.

(iii) In a manner analogous to that described in Example 1, parts (vii) and (viii) but using O-benzylhydroxylamine in place of O-(tetrahydro-2H-pyran-2(RS)-yl)hydroxylamine there was obtained N-[8-[N-(benzyloxycarbonyl) aminoacetyl]-2,4-dioxo-1,3,8-triazaspiro[4.5]decan-3-yl)-2(R)-[1(S)-(benzyloxycarbamoyl)-4-phenylbutyl]-3-methylvaleramide in the form of a white solid.

MS: 755 (M+H)$^+$.

EXAMPLE 25

2(R)-[1(S)-(Hydroxycarbamoyl)-4-phenylbutyl]-4-methyl-N-(2,4-dioxo-1,3,8-triazaspriro[4.5]decan-3-yl)valeramide p-toluenesulphonate In a manner analogous to that described in Example 3 from 0.099 g of 2(R)-[1(S)-[(tetrahydro-2(RS)-pyranyloxy)carbamoyl]-4-phenylbutyl]-4-methyl-N-(2,4-dioxo-1,3,8-triazaspiro[4.5]decan-3-yl)valeramide there was obtained 0.05 g of 2(R)-[1(S)-(hydroxycarbamoyl)-4-phenylbutyl]-4-methyl-N-(2,4-dioxo-1,3,8-triazaspiro[4.5]decan-3-yl) valeramide p-toluenesulphonate in the form of an off-white solid.

MS: 474 (M+H)$^+$.

HPLC: Gradient elution using solvent A containing 5% solvent B increasing to 95% solvent B over 15 minutes; flow rate 1 ml/minute. Retention time: 7.39 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbamoyl]-4-phenylbutyl]-4-methyl-N-(2,4-dioxo-1,3,8-triazaspiro[4.5]decan-3-yl)valeramide used as the starting material was prepared as follows:

(i) In a manner analogous to that described in Example 1, parts (vii) and (viii) starting from benzyl 3-[2(R)-[1(S)-(tert-butoxycarbonyl)-4-phenylbutyl]-4-methylvaleramido]-2,4-dioxo-1,3,8-triazaspiro[4.5]decane-8-carboxylate there was obtained benzyl 3-[2(R)-[1(S)-[(tetrahydro-2(RS)-pyranyloxy)carbamoyl]-4-phenylbutyl]-4-methylvaleramido]-2,4-dioxo-1,3,8-triazaspiro[4.5]decane-8-carboxylate in the form of a white solid.

MS: 692 (M+H)$^+$.

(ii) A solution of 0.13 g of benzyl 3-[2(R)-[1(S)-[(tetrahydro-2(RS)-pyranyloxy)carbamoyl]-4-phenylbutyl]-4-methylvaleramido]-2,4-dioxo-1,3,8-triazaspiro[4.5]decane-8-carboxylate in 10 ml methanol was shaken in a hydrogen atmosphere for 3 hours. The catalyst was filtered off and the methanol evaporated. There was obtained 0.099 g of 2(R)-[1(S)-[(tetrahydro-2(RS)-pyranyloxy)carbamoyl]-4-phenylbutyl]-4-methyl-N-(2,4-dioxo-1,3,8-triazaspiro [4.5]decan-3-yl-valeramide in the form of a white solid.

MS: 558 (M+H)$^+$.

EXAMPLE 26

2(R)-[1(S)-(Hydroxycarbamoyl)-4-phenylbutyl]-N-[8-(methanesulphonyl)-2,4-dioxo-1,3,8-triazaspiro[4.5]decan-3-yl]-4-methylvaleramide In a manner analogous to that described in Example 7 from 0.105 g of 2(R)-[1(S)-(benzyloxycarbamoyl)-4-phenylbutyl]-N-[8-(methanesulphonyl)-2,4-dioxo-1,3,8-triazaspiro[4.5]decan-3-yl]-4-methylvaleramide there was obtained 0.076 g of 2(R)-[1(S)-(hydroxycarbamoyl)-4-phenylbutyl]-N-[8-(methanesulphonyl)-2,4-dioxo-1,3,8-triazaspiro[4.5]decan-3-yl]-4-methylvaleramide in the form of a white solid.

MS: 552 (M+H)$^+$.

HPLC: Gradient elution using solvent A containing 5% solvent B increasing to 95% solvent B over 15 minutes; flow rate 1 ml/minute. Retention time: 8.85 minutes. Solvent A: H$_2$O/0.1% TFA; solvent B: CH$_3$CN/0.085% TFA. Column type: HYPERPEP 300A.

The 2(R)-[1(S)-(benzyloxycarbamoyl)-4-phenylbutyl]-N-[8-(methanesulphonyl)-2,4-dioxo-1,3,8-triazaspiro[4.5] decan-3-yl]-4-methylvaleramide used as the starting material was prepared as follows:

(i) A solution of 0.514 g of 2(R)-[1(S)-tert-butoxycarbonyl)-4-phenylbutyl]-4-methyl-N-[2,4-dioxo-1,3,8-triazaspiro[4.5]decan-3-yl]valeramide in 10 ml of dry pyridine was cooled to 0° C. with stirring and 0.13 ml of methanesulphonyl chloride added. The mixture was allowed to return to room temperature and was stirred for 2 days. The solvent was evaporated and the residue partitioned between ethyl acetate and dilute hydrochloric acid. The ethyl acetate layer was washed successively with water and saturated sodium chloride solution, dried over anhydrous magnesium sulphate and the solvent evaporated. The residue was purified by flash chromatography using 5% methanol in dichloromethane for the elution. There was obtained 0.322 g of 2(R)-[1(S)-tert-butoxycarbonyl)-4-phenylbutyl]-N-[8-(methanesulphonyl)-2,4-dioxo-1,3,8-triazaspiro[4.5]decan-3-yl]-4-methylvaleramide in the form of a white solid.

MS: 593 (M+H)$^+$.

(ii) In a manner analogous to that described in Example 7, part (iii) from 2(R)-[1(S)-tert-butoxycarbonyl)-4- phenylbutyl]-N-[8-(methanesulphonyl)-2,4-dioxo-1,3,8-triazaspiro[4.5]decan-3-yl]-4-methylamide there was obtained 2(R)-[1(S)-(benzyloxycarbamoyl)-4-phenylbutyl]-N-[8-(methanesulphonyl)-2,4-dioxo-1,3,8-triazaspiro-[4.5]decan-3-yl]-4-methylvaleramide as a white solid.

MS: 593 (M+H)+.

EXAMPLE 27

N-[8-(Benzenesulphonyl)-2,4-dioxo-1,3,8-triazaspiro[4.5]decan-3-yl]-2(R)-[1(S)-(hydroxycarbamoyl)-4-phenylbutyl]-4-methylvaleramide In a manner analogous to that described in Example 3 from 0.255 g of N-[8-(benzenesulphonyl)-2,4-dioxo-1,3,8-triazespiro [4.5]decan-3-yl]-2(R)-[1(S)-[(tetrahydro-2(RS)-pyranyloxy)carbamoyl]-4-phenylbutyl]-4-methylvaleramide there was obtained 0.198 g of N-[8-(benzenesulphonyl)-2,4-dioxo-1,3,8-triazaspiro[4.5]decan-3-yl]-2(R)-[1(S)-(hydroxycarbamoyl)-4-phenylbutyl]-4-methylamide in the form of a white solid.

MS: 614 (M+H)+.

HPLC: Gradient elution using solvent A containing 5% solvent B increasing to 95% solvent B over 15 minutes; flow rate 1 ml/minute. Retention time: 10.48 minutes. Solvent A: H$_2$O/0.1% TFA; solvent B: CH$_3$CN/0.085% TFA. Column type: HYPERPEP 300A.

The N-[8-(benzenesulphonyl)-2,4-dioxo-1,3,8-triazaspiro [4.5]decan-3-yl]-2(R)-[1(S)-[(tetrahydro-2(RS)-pyranyloxy)carbamoyl]-4-phenylbutyl]-4-methylvaleramide used as the starting material was prepared as follows:

(i) In a manner analogous to that described in Example 26, part (i) but using benzenesulphonyl chloride in place of methanesulphonyl chloride from 0.83 g of 2(R)-[1(S)-(tert-butoxycarbonyl)-4-phenylbutyl]-4-methyl-N-[2,4-dioxo-1,3,8-triazaspiro[4.5]decan-3-yl]valeramide there was obtained 0.889 g of N-[8-(benzenesulphonyl)-2,4-dioxo-1,3,8-triazaspiro[4.5]decan-3-yl]-2(R)-[1(S)-(tert-butoxycarbonyl)-4-phenylbutyl]-4-methylvaleramide in the form of a white solid.

MS: 655 (M+H)+.

(ii) In a manner analogous to that described in Example 1, parts (vii) and (viii) from N-[8-(benzenesulphonyl)-2,4-dioxo-1,3,8-triazaspiro[4.5]decan-3-yl]-2(R)-[1(S)-(tert-butoxycarbonyl)-4-phenylbutyl]-4-methylvaleramide there was obtained N-[8-(benzenesulphonyl)-2,4-dioxo-1,3,8-triazaspiro [4.5]decan-3-yl]-2(R)-[(tetrahydro-2(RS)-pyranyloxy)carbamoyl]-4-phenylbutyl]-4-methylvaleramide in the form of a white solid.

MS: 698 (M+H)+.

EXAMPLE 28

N-(1,2,3,4-Tetrahydro-2,4-dioxo-3-quinazolinyl)-2(R)-[1(S)-(hydroxycarbamoyl)-4-phenylbutyl]-4-methylvaleramide In a manner analogous to that described in Example 7 from 0.095 g of 2(R)-[1(S)-(benzyloxycarbamoyl)-4-phenylbutyl]-N-(1,2,3,4-tetrahydro-2,4-dioxo-3-quinazolinyl)-4-methylvaleramide there was obtained 0.059 g of N-(1,2,3,4-tetrahydro- 2,4-dioxo-3-quinazolinyl)-2(R)-[1(S)-(hydroxycarbamoyl)-4-phenylbutyl]-4-methylvaleramide in the form of a white solid.

MS: 467 (M+H)+.

HPLC: Gradient elution using solvent A containing 5% solvent B increasing to 95% solvent B over 15 minutes; flow rate 1 ml/minute. Retention time: 9.38 minutes. Solvent A: H$_2$O/0.1% TFA; solvent B: CH$_3$CN/0.085% TFA. Column type: HYPERPEP 300A.

The 2(R)-[1(S)-(benzyloxycarbamoyl)-4-phenylbutyl]-N-(1,2,3,4-tetrahydro-2,4-dioxo-3-quinazolinyl)-4-methylvaleramide used as the starting material was prepared as follows:

(i) In a manner analogous to that described in Example 7, part (ii) starting from 2(R)-[1(S)-(tert-butoxycarbonyl)-4-phenylbutyl]-4-methylvalerohydrazide and 2-methoxycarbonylphenyl isocyanate there was obtained 2(R)-[1(S)-(tert-butoxycarbonyl)-4-phenylbutyl]-N-(1,2,3,4-tetrahydro-2,4-dioxo-3-quinazolinyl)-4-methylvaleramide in the form of a colourless gum.

MS: 508 (M+H)+.

(ii) In a manner analogous to that described in Example 7, part (iii) starting from 2(R)-[1(S)-(tert-butoxycarbonyl)-4-phenylbutyl]-N-(1,2,3,4-tetrahydro-2,4-dioxo-3-quinazolinyl)-4-methylvaleramide there was obtained 2(R)-[1(S)-(benzyloxycarbamoyl)-4-phenylbutyl]-N-(1,2,3,4-tetrahydro-2,4-dioxo-3-quinazolinyl)-4-methylvaleramide in the form of a white solid.

MS: 557 (M+H)+.

EXAMPLE 29

N-(1,2,3,4-Tetrahydro-2,4-dioxothieno[3,2-d]pyrimidin-3-yl)-2(R)-[1(S)-(hydroxycarbamoyl)-4-phenylbutyl]-4-methylvaleramide In a manner analogous to that described in Example 1 from 0.3 g of N-(1,2,3,4-tetrahydro-2,4-dioxothieno[3,2-d]pyrimidin-3-yl)-2(R)-[1(S)-[(tetrahydro-2(RS)-pyranyloxy)carbamoyl]-4-phenylbutyl]-4-methylvaleramide there was obtained 0.211 g of N-(1,2,3,4-tetrahydro-2,4-dioxothieno[3,2-d]pyrimidin-3-yl)-2(R)-[1(S)-[(hydroxycarbamoyl)-4-phenylbutyl]-4-methylvaleramide in the form of a white solid.

MS: 473 (M+H)+.

HPLC: Gradient elution using solvent A containing 5% solvent B increasing to 95% solvent B over 15 minutes; flow rate 1 ml/minute. Retention time: 8.86 minutes. Solvent A: H$_2$O/0.1% TFA; solvent B: CH$_3$CN/0.085% TFA. Column type: HYPERPEP 300A.

The N-(1,2,3,4-tetrahydro-2,4-dioxothieno[3,2-d]pyrimidin-3-yl)-2(R)-[1(S)-[(tetrahydro-2(RS)-pyranyloxy)carbamoyl]-4-phenylbutyl]-4-methylvaleramide used as the starting material was prepared as follows:

(i) A solution of 0.471 g of methyl 3-aminothiophene-2-carboxylate in 15 ml of dry toluene was cooled to 0° C. with stirring and 0.975 g of 2,6-lutidine added followed by the addition of 0.3 g of triphosgene. The mixture was stirred at 0° C. for 1.75 hours and then 1.066 g of 2(R)-[1(S)-(tert-butoxycarbonyl)-4-phenylbutyl]-4-methylvalerohydrazide added. The mixture was stirred and allowed to warm to room temperature over 4 hours and was then diluted with ethyl acetate and then washed successively with two portions of aqueous 5% citric acid solution, water, and saturated sodium chloride solution. After evaporation of the solvent the yellow residue was purified by flash chromatography using hexane/ethyl acetate (2: 1) for the elution.

After removal of the solvent 1.3 g of a colourless residue was obtained.

MS: 546 (M+H)+.

The residue was dissolved in 40 ml of toluene and heated to 90° C. at which time 0.275 g of 1,1,3,3-tetramethylguanidine was added. After 55 minutes the mixture was cooled and the solution diluted with ethyl acetate and washed successively with 5% aqueous citric acid solution, water and saturated sodium chloride solution. After drying over anhydrous magnesium sulphate the solvent was evaporated and the residue triturated with diethyl ether. There was obtained 1.022 g of 2(R)-[1(S)-(tert.butoxycarbonyl)-4-phenylbutyl]-N-(1,2,3,4-tetrahydro-2,4-dioxothieno[3,2-d]pyrimidin-3-yl)-4-methylvaleramide in the form of a white solid.

MS: 514 (M+H)$^+$.

(ii) In a manner analogous to that described in Example 1, parts (vii) and (viii) starting from 2(R)-[1(S)-(tert.-butoxycarbamoyl)-4-phenylbutyl-N-(1,2,3,4-tetrahydro-2,4-dioxothieno[3,2-d]pyrimidin-3-yl)-4-methylvaleramide there was obtained N-(1,2,3,4-tetrahydro-2,4-dioxothieno[3,2-d]pyrimidin-3-yl)-2(R)-[1(S)-[(tetrahydro-2(RS)-pyranyloxy)carbamoyl]-4-phenylbutyl]-4-methylvaleramide in the form of a white solid.

MS: 557 (M+H)$^+$.

EXAMPLE 30

N-(1,2,3,4-Tetrahydro-2,4-dioxothieno[3,4-d] pyrimidin-3-yl)-2(R)-[1(S)-(hydroxycarbamoyl)-4-phenylbutyl]-4-methylvaleramide In a manner analogous to that described in Example 3 from 0.22 g of N-(1,2,3,4-tetrahydro-2,4-dioxothieno[3,4-d] pyrimidin-3-yl)-2(R)-[1(S)-[(tetrahydro- 2(RS)-pyranyloxy)carbamoyl]-4-phenylbutyl]-4-methylvaleramide there was obtained 0.16 g of N-(1,2,3,4-tetrahydro-2,4-dioxothieno[3,4-d]pyrimidin-3-yl)-2(R)-[1(S)-(hydroxycarbamoyl)-4-phenylbutyl]-4-methylvaleramide in the form of a white solid.

MS: 473 (M+H)$^+$

HPLC: Gradient elution using solvent A containing 5% solvent B increasing to 95% solvent B over 15 minutes; flow rate 1 ml/minute. Retention time: 9.00 minutes. Solvent A: H$_2$O/0.1% TFA; solvent B: CH$_3$CN/0.085% TFA. Column type: HYPERPEP 300A.

The N-(1,2,3,4-tetrahydro-2,4-dioxothieno[3,4-d] pyrimidin-3-yl)-2(R)-[1(S)-[(tetrahydro-2(RS)-pyranyloxy) carbamoyl]-4-phenylbutyl]-4-methylvaleramide used as the starting material was prepared in a manner analogous to that described in Example 29, parts (i) and (ii) starting from methyl 3-aminothiophene-4-carboxylate and 2(R)-[1(S)-(tert-butoxycarbonyl)-4-phenylbutyl]-4-methylvalerohydrazide and was obtained in the form of a white solid.

MS: 557 (M+H)$^+$.

EXAMPLE 31

N-(1,2,3,4,5,6,7-Octahydro-2,4-dioxo-3-quinazolin-3-yl)-2(R)-[1(S)-(hydroxycarbamoyl)-4-phenylbutyl]-4-methylvaleramide In a manner analogous to that described in Example 3 from 0.18 g of N-(1,2,3,4,5,6,7-octahydro-2,4-dioxo-3-quinazolin-3-yl)-2(R)-[1(S)-[(tetrahydro-2(RS)-pyranyloxy)carbamoyl]-4-phenylbutyl]-4-methylvaleramide there was obtained 0.058 g of N-(1,2,3,4,5,6,7-octahydro-2,4-dioxo-3-quinazolin-3-yl)-2(R)-[1(S)-(hydroxycarbamoyl)-4-phenylbutyl]-4-methylvaleramide in the form of a white solid.

MS: 471 (M+H)$^+$.

HPLC: Gradient elution using solvent A containing 5% solvent B increasing to 95% solvent B over 15 minutes; flow rate 1 ml/minute. Retention time: 9.13 minutes. Solvent A: H$_2$O/0.1% TFA; solvent B: CH$_3$CN/0.085% TFA. Column type: HYPERPEP 300A.

The N-(1,2,3,4,5,6,7-octahydro-2,4-dioxo-3-quinazolin-3-yl)-2(R)-[1(S)-[(tetrahydro-2(RS)-pyranyloxy)carbamoyl [-4-phenylbutyl]-4-methylvaleramide used as the starting material was prepared in a manner analogous to that described in Example 29, parts (i) and (ii) starting from 2-amino-1-cyclohexene-1-carboxylate and 2(R)-[1(S)-(tert-butoxycarbonyl)-4-phenylbutyl]-4-methylvalerohydrazide and was obtained in the form of a white solid.

MS: 555 (M+H)$^+$.

EXAMPLE 32

N-(1,2,3,4-Tetrahydro-2,4-dioxopyrido [2,3-d] pyrimidin-3-yl)-2(R)-[1(S)-(hydroxycarbamoyl)-4-phenylbutyl]-4-methylvaleramide In a manner analogous to that described in Example 3 from 0.293 g of N-(1,2,3,4-tetrahydro-2,4-dioxopyrido[2,3-d]pyrimidin-3-yl)-2(R)-[1(S)-[(tetrahydro-2(RS)-pyranyloxy)carbamoyl]-4-phenylbutyl]-4-methylvaleramide there was obtained 0.11 g of N-(1,2,3,4-tetrahydro-2,4-dioxopyrido [2,3-d]pyrimidin-3-yl)-2(R)-[1 (S)-(hydroxycarbamoyl)-4-phenylbutyl]-4-methylvaleramide in the form of an off-white solid.

MS: 468 (M+H)$^+$.

HPLC: Gradient elution using solvent A containing 5% solvent B increasing to 95% solvent B over 15 minutes; flow rate 1 ml/minute. Retention time: 8.57 minutes. Solvent A: H$_2$O/0.1% TFA; solvent B: CH$_3$CN/0.085% TFA. Column type: HYPERPEP 300A.

The N-(1,2,3,4-tetrahydro-2,4-dioxopyrido [2,3-d] pyrimidin-3-yl)-2(R)-[1(S)-[(tetrahydro-2(RS)-pyranyloxy) carbamoyl]-4-phenylbutyl]-4-methylvaleramide used as the starting material was prepared in a manner analogous to that described in Example 29, parts (i) and (ii) starting from methyl 2-aminonicotinate and 2(R)-[1(S)-(tert-butoxycarbonyl)-4-phenylbutyl]-4-methylvaleramide and was obtained in the form of a white solid.

MS: 552 (M+H)$^+$.

EXAMPLE 33

2(R)-[1(S)-(Hydroxycarbamoyl)-4-phenylbutyl]- N-[4(S)-methoxymethyl)-2,5-dioxo-1-imidazolidinyl]-4-methylvaleramide In a manner analogous to that described in Example 3 from 0.561 g of 2(R)-[[1(S)-[(tetrahydro-2(RS)-pyranyloxy) carbamoyl]-4-phenylbutyl]-N-[4(S)-(methoxymethyl)-2,5-dioxo-1-imidazolidinyl]-4-methylvaleramide there was obtained 0.11 g of 2(R)-[1(S)-(hydroxycarbamoyl)-4-phenylbutyl]-N-[4(S)-(methoxymethyl)-2,5-dioxo-1-imidazolidinyl]-4-methylvaleramide in the form of an off-white solid.

MS: 449 (M+H)$^+$.

HPLC: Gradient elution using solvent A containing 5% solvent B increasing to 95% solvent B over 15 minutes; flow rate 1 ml/minute. Retention time: 8.33 minutes. Solvent A: H$_2$O/0.1% TFA; solvent B: CH$_3$CN/0.085% TFA. Column type: HYPERPEP 300A The 2(R)-[1(S)-[(tetrahydro-2(RS)-pyranyloxy) carbamoyl]-4-phenylbutyl]-N-[4(S)-(methoxymethyl)-2,5- dioxo-1-imidazolidinyl]-4-methylvaleramide used as the starting material was prepared in a manner analogous to that described in Example 7, part (ii) and Example 1, parts (vii) and (viii), starting from 2(R)-[1(S)-(tert-butoxycarbonyl)-4-phenylbutyl]-4-methylvalerohydrazide and methyl (S)-2-isocyanato-3-methoxypropionate.

MS: 533(M+H)+.

EXAMPLE 34

2(R)-[1(S)-(Hydroxycarbamoyl)-4-phenylbutyl]-N-(2-oxo-1-imidazolidinyl)-4-methylvaleramide A solution of 0.125 g of (E)-2(R)-[1(S)-(benzyloxycarbamoyl)-4-phenylbut-3-enyl]-N-(3-benzyl-2-oxo-1-imidazolinyl)-4-methylvaleramide in 10 ml of methanol was hydrogenated for 3 hours in the presence of 0.020 g of palladium(II)hydroxide. The catalyst was removed by filtration and evaporation of the solvent and trituration of the residue gave 0.049 g of 2(R)-[1(S)-(hydroxycarbamoyl)-4-phenylbutyl]-N-(2-oxo-1-imidazolidinyl)-4-methylvaleramide in the form of a white solid.

MS: 391 (M+H)+.

HPLC: Gradient elution using solvent A containing 5% solvent B increasing to 95% solvent B over 15 minutes; flow rate 1 ml/minute. Retention time: 10.70 minutes. Solvent A: $H_2O$/0.1% TFA; solvent B: $CH_3CN$/0.085% TFA. Column type: HYPBDSC18

The (E)-2(R)-[1(S)-(benzyloxycarbamoyl)-4-phenylbut-3-enyl]-N-(3-benzyl-2-oxo-1-imidazolinyl)-4-methylvaleramide used as the starting material was prepared as follows:

(i) A solution of 1.0 g of (E)-2(R)-[1(S)-(tert-butoxycarbonyl)-4-phenyl-3-butenyl]-4-methylvalerohydrazide in 10 ml of tetrahydrofuran was treated with 0.59 g of sodium carbonate. The mixture was cooled to 0° C. and 1.73 ml of a 1.93M solution of phosgene in toluene was added. The mixture was allowed to warm to room temperature and then stirred overnight. Filtration and evaporation of the filtrate gave 1.15 g of (E)-2(S)-(tert-butoxycarbonyl)-1(R)-isobutyl-5-phenylpent-4-enyl-1,3,4-oxadiazol-2(3H)-one in the form of a clear oil which crystallized on standing.

MS: 386

(ii) A solution of 0.5 g of (E)-2(S)-(tert-butoxycarbonyl)-1(R)-isobutyl-5-phenylpent-4-enyl-1,3,4-oxadiazol-2(3H)-one in 5 ml of dimethylformamide was added slowly to a cold (0° C.) suspension of sodium hydride (60% suspension in mineral oil) in 10 ml of dry dimethylformamide. The mixture was warmed to room temperature and then heated at 50–60° C. until hydrogen evolution ceased. The mixture was then cooled to 0° C. and treated with 0.293 ml of dibromoethane whilst stirring rapidly. The mixture was again warmed to room temperature and then heated at 70° C. for 1 hour. The solvent was evaporated and the residue dissolved in warm ethyl acetate. Filtration and evaporation of the filtrate gave 0.616 g of(E)-2(S)-{1(R)-[4-(2-bromoethyl)-5-oxo-4,5-dihydro-[1,3,4]oxadiazol-2-yl]-3-methyl-butyl}-5-phenyl-pent-4-enoic acid tert-butyl ester in the form of a clear oil.

MS: 436 (M-56(tBu))

(iii) A solution of 0.616 g of (E)-2(S)-{1(R)-[4-(2-bromoethyl)-5-oxo-4,5-dihydro-[1,3,4]oxadiazol-2-yl]-3-methyl-butyl}-5-phenyl-pent-4-enoic acid tert-butyl ester in 15 ml of acetonitrile was treated with 0.275 ml of benzylamine and refluxed at 80° C. for 3 hours. A further 0.275 ml of benzylamine was added to the mixture and refluxing was continued overnight. The mixture was cooled to room temperature, diluted with ethyl acetate, and washed sequentially with 5% aqueous citric acid, 5% aqueous sodium hydrogen carbonate and saturated aqueous sodium chloride. The organic layer was then dried over anhydrous magnesium sulphate and evaporated to give a residual oil which was purified by flash column chromatography on silica gel, using ethyl acetate/hexane (1:1) as the eluant, to give 0.255 g of (E)-2(R)-[1(S)-(tert-(butyloxy)carbonyl)- 4-phenylbut-3-enyl]-N-(3-benzyl-2-oxo-1-imidazolinyl)-4-methylvaleramide in the form of a colourless oil.

MS: 520 (M+H)+

(iv) A solution of 0.255 g of (E)-2(R)-[1(S)-(tert-(butyloxy)carbonyl)-4-phenylbut-3-enyl]-N-(3-benzyl-2-oxo-1-imidazolinyl)-4-methylvaleramide in 5 ml of dichloromethane was treated with 2.5 ml of trifluoroacetic acid. The mixture was stirred at room temperature for 2.5 hours and evaporated. Traces of trifluoroacetic acid were removed by the three-fold addition and evaporation of toluene to give 0.290 g of (E)-2(R)-[1(S)-(carboxy)-4-phenylbut-3-enyl]-N-(3-benzyl-2-oxo-1-imidazolinyl)-4-methylvaleramide in the form of a white foam.

MS: 464 (M+H)+

(v) A solution of 0.290 g of (E)-2(R)-[1(S)-(carboxy)-4-phenylbut-3-enyl]-N-(3-benzyl-2-oxo-1-imidazolinyl)-4-methylvaleramide in 3 ml of dimethylformamide was treated with 0.362 g of O-benzylhydroxylamine. The mixture was cooled to 0° C. under nitrogen and treated with 0.141 g of 1-ethyl-3-(3-dimethylaminopropyl)-carbodiimide hydrochloride. The mixture was left to warm to room temperature and was stirred overnight. Evaporation gave a residue which was dissolved in ethyl acetate and washed in sequence with 5% aqueous citric acid, 5% aqueous sodium hydrogen carbonate and saturated aqueous sodium chloride. Drying over anhydrous magnesium sulphate and evaporation gave a residue which was purified by flash column chromatography on silica gel using ethyl acetate/hexane (2:1) for the elution to give 0.251 g of (E)-2(R)-[1(S)-(benzyloxycarbamoyl)-4-phenylbut-3-enyl]-N-(3-benzyl-2-oxo-1-imidazolinyl)-4-methylvaleramide in the form of an oil.

MS: 569 (M+H)+

EXAMPLE 35

(E)-2(R)-[1(S)-(Hydroxycarbamoyl)-4-phenyl-3-butenyl]-4-methyl-N-(2,4-dioxo-1-imidazolidinyl) valeramide A solution of 0.298 g of (E)-2(R)-[1(S)-[(tetrahydro-2 (RS)-pyranyloxy)carbamoyl]-4-phenyl-3-butenyl]-4-methyl-N-(2,4-dioxo-1-imidazolidinyl)valeramide in 3 ml of methanol was treated with 0.030 g of p-toluenesulphonic acid monohydrate. The mixture was stirred for 3.5 hours at room temperature and then diluted with ethyl acetate and washed in sequence with 5% aqueous sodium hydrogen carbonate and saturated aqueous sodium chloride. The organic layer was dried over anhydrous magnesium sulphate and evaporated. The residue was triturated with diethyl ether to give 0.076 g of (E)-2(R)-[1(S)-(Hydroxycarbamoyl)-4-phenyl-3-butenyl]-4-methyl-N-(2,4-dioxo-1-imidazolidinyl)valeramide in the form of a white solid.

MS: 403 (M+H)+.

HPLC: Gradient elution using solvent A containing 5% solvent B increasing to 95% solvent B over 15 minutes; flow rate 1 ml/minute. Retention time: 7.91 minutes. Solvent A: $H_2O$/0.1% TFA; solvent B: $CH_3CN$/0.085% TFA. Column type: HYPERPEP 300A.

The (E)-2(R)-[1(S)-[(tetrahydro-2(RS)-pyranyloxy)carbamoyl]-4-phenyl-3-butenyl]-4-methyl-N-(2,4-dioxo-1-imidazolidinyl)valeramide used as the starting material was prepared as follows:

(i) A solution of 0.600 g of (E)-2(S)-(tert-butoxycarbonyl)-1(R)-isobutyl-5-phenylpent-4-enyl-1,3,4-oxadiazol-2(3H)-one (prepared as described in Example 34, part (i)) in 5 ml of dimethylformamide was added slowly to a cold (0° C.) suspension of sodium hydride (60% suspension in mineral oil) in 10 ml of dry dimethylformamide. The mixture was warmed to room temperature and then heated at 50–60° C. until hydrogen evolution ceased. The mixture was then cooled to 0° C. and treated with 0.535 g of bromoacetamide whilst stirring rapidly. The mixture was again warmed to room temperature and then heated at 70° C. for 1 hour and at 82° C. for a further 1 hour. The solvent was evaporated the residue was dissolved in ethanol and treated with 5 ml of a 32% aqueous ammonia solution. The mixture was stirred for 48 hours at room temperature and then evaporated. The residue was dissolved in ethyl acetate and washed with 5% aqueous citric acid, 5% aqueous sodium hydrogen carbonate, and saturated aqueous sodium chloride. Drying over anhydrous magnesium sulphate and evaporation gave 0.553 g of (E)-2(R)-[1(S)-(tert-butoxycarbonyl)-4-phenyl-3-butenyl]-4-methyl-N-(2,4-dioxo-1-imidazolidinyl)valeramide in the form of a white foam.

MS: 444 (M+H)$^+$.

(ii) In an analogous manner to that described in Example 1, parts (vii)–(viii), but using (E)-2(R)-[1(S)-(tert-butoxycarbonyl)-4-phenyl-3-butenyl]-4-methyl-N-(2,4-dioxo-1-imidazolidinyl)valeramide in place of (E)-2(R)-[1(S)-(tert-butoxycarbonyl)-4-phenyl-3-butenyl]-4-methyl-N-(2,5-dioxo-1-imidazolidinyl)valeramide there was obtained (E)-2(R)-[1(S)-[(tetrahydro-2(RS)-pyranyloxy)carbamoyl]-4-phenyl-3-butenyl]-4-methyl-N-(2,4-dioxo-1-imidazolidinyl)valeramide in the form of a white solid.

MS: 487 (M+H)$^+$.

EXAMPLE 36

2(R)-[4-Cyclohexyl-1(S)-(hydroxycarbamoyl)butyl]-4-methyl-N-(2,4-dioxo-1-imidazolidinyl)valeramide A solution of 0.134 g of (E)-2(R)-[1(S)-(hydroxycarbamoyl)-4-phenyl-3-butenyl]-4-methyl-N-(2,4-dioxo-1-imidazolidinyl)valeramide (prepared as described in Example 35) in 10 ml of acetic acid was hydrogenated for 1.66 hours in the presence of 0.015 g of platinum (IV) oxide. The catalyst was removed by filtration and evaporation gave a residue which was triturated with diethyl ether to give 0.078 g of 2(R)-[4-cyclohexyl-1(S)-(hydroxycarbamoyl)butyl]-4-methyl-N-(2,4-dioxo-1-imidazolidinyl)valeramide in the form of a white solid.

MS: 411 (M+H)$^+$.

HPLC: Gradient elution using solvent A containing 5% solvent B increasing to 95% solvent B over 15 minutes; flow rate 1 ml/minute. Retention time: 9.22 minutes. Solvent A: H$_2$O/0.1% TFA; solvent B: CH$_3$CN/0.085% TFA. Column type: HYPERPEP 300A.

EXAMPLE 37

2(R)-[1(S)-(Hydroxycarbamoyl)-4-phenylbutyl]-N-[tetrahydro-3-oxo-2H-1,2,4-thiadiazin-2-yl]-4-methylvaleramide-S,S-dioxide A solution of 0.126 g of (E)-2(R)-[1(S)-(benzyloxycarbamoyl)-4-phenylbut-3-enyl]-N-[tetrahydro-3-oxo-2H-1,2,4-thiadiazin-2-yl]-4-methylvaleramide-S,S-dioxide in 10 ml of ethanol was hydrogenated for 3 hours in the presence of 0.040 g of 5% palladium-on-carbon. The catalyst was removed by filtration and evaporation of the solvent gave 0.091 g of 2(R)-[1(S)-(hydroxycarbamoyl)-4-phenylbutyl]-N-[tetrahydro- 3-oxo-2H-1,2,4-thiadiazin-2-yl]-4-methylvaleramide-S,S-dioxide in the form of a white solid.

MS: 455 (M+H)$^+$.

HPLC: Gradient elution using solvent A containing 5% solvent B increasing to 95% solvent B over 15 minutes; flow rate 1 ml/minute. Retention time: 8.07 minutes. Solvent A: H$_2$O/0.1% TFA; solvent B: CH$_3$CN/0.085% TFA. Column type: HYPERPEP 300A.

The (E)-2(R)-[1(S)-(benzyloxycarbamoyl)-4-phenylbut-3-enyl]-N-[tetrahydro-3-oxo-2H-1,2,4-thiadiazin-2-yl]-4-methylvaleramide-S,S-dioxide used as the starting material was prepared as follows:

(i) A solution of 3.0 g of (E)-2(R)-[1(S)-(tert-butoxycarbonyl)-4-phenyl-3-butenyl]-4-methylvalerohydrazide in 50 ml of dichloromethane was treated with 0.88 ml of pyridine and 2.73 g of 2-phthalimidoethanesulphonyl chloride at room temperature under a nitrogen atmosphere. The mixture was stirred for 12 hours at room temperature and evaporated. The residue was dissolved in ethyl acetate and washed in sequence with 5% aqueous citric acid, 5% aqueous sodium hydrogen carbonate and saturated aqueous sodium chloride. Drying over anhydrous magnesium sulphate and evaporation gave 4.9 g of (E)-2(R)-[1(S)-(tert-butoxycarbonyl)-4-phenyl-3-butenyl]-2'-(1,3-dioxo-2-phthalimidoethanesulphonyl)-4-methylvalerohydrazide in the form of a pale yellow foam.

MS: 598 (M+H)$^+$.

(ii) A solution of 4.9 g of (E)-2(R)-[1(S)-(tert-butoxycarbonyl)-4-phenyl-3-butenyl]-2'-(1,3-dioxo-2-phthalimidoethanesulphonyl)-4-methylvalerohydrazide in 50 ml of ethanol was treated with 0.82 ml of hydrazine hydrate and stirred at room temperature overnight. The mixture was filtered and the filtrate was dried over anhydrous magnesium sulphate and evaporated. The residue was purified by flash column chromatography on silica gel using methanol/dichloromethane (1:9) for the elution to give 3.28 g of an off-white solid. This was further purified by trituration with diethyl ether to give 1.96 g of (E)-2'-(2-aminoethanesulphonyl)-2(R)-[1(S)-(tert-butoxycarbonyl)-4-phenyl-3-butenyl]-4-methylvalerohydrazide in the form of a white solid.

MS: 468 (M+H)$^+$.

(iii) A suspension of 1.96 g of (E)-2'-(2-aminoethanesulphonyl)-2(R)-[1(S)-(tert-butoxycarbonyl)-4-phenyl-3-butenyl]-4-methylvalerohydrazide in 100 ml of dichloromethane was cooled to 0° C. under a nitrogen atmosphere and treated with 1.6 ml of N-ethylmorpholine and 2.8 ml of a 1.93M solution of phosgene in toluene. The mixture was warmed to room temperature over 2 hours and evaporated. The residue was dissolved in ethyl acetate and washed in sequence with 2M aqueous hydrogen chloride and saturated aqueous sodium chloride. Drying over anhydrous magnesium sulphate and evaporation gave 1.99 g of (E)-2(R)-[1(S)-(tert-butoxycarbonyl)-4-phenylbut-3-enyl]-N-[tetrahydro-3-oxo-2H-1,2,4-thiadiazin-2-yl]-4-methylvaleramide-S,S-dioxide in the form of a light yellow solid.

MS: 468 (M+H)$^+$.

(iv) In an analogous manner to that described in Example 34, parts (iv)–(v), but using (E)-2(R)-[1(S)-(tert-butoxycarbonyl)-4-phenylbut-3-enyl]-N-[tetrahydro-3-oxo-2H-1,2,4-thiadiazin-2-yl]-4-methylvaleramide-S,S-dioxide in place of (E)-2(R)-[1(S)-(tert-(butyloxy)carbonyl)-4-phenylbut-3-enyl]-N-(3-benzyl-2-oxo-1-imidazolinyl)-4-methylvaleramide there was obtained (E)-2(R)-[1(S)-(benzyloxycarbamoyl)-4-phenylbut-3-enyl]-N-[tetrahydro-3-oxo-2H-1,2,4-thiadiazin-2-yl]-4-methylvaleramide-S,S-dioxide in the form of a white solid.

MS: 543 (M+H)$^+$.

EXAMPLE 38

2(R)-[1(S)-(Hydroxycarbamoyl)-4-phenylbutyl]-4-methyl-N-(2,5-dioxo-1-imidazolidinyl)valeramide A solution of 0.290 g of 2(R)-[1(S)-(benzyloxycarbamoyl)-4-phenylbutyl]-4-methyl-N-(2,5-dioxo-1-imidazolidinyl)valeramide in 10 ml of methanol was hydrogenated for 2 hours in the presence of 0.087 g of 5% palladium-on-carbon. The catalyst was removed by filtration and evaporation of the solvent gave a residue which was purified by flash column chromatography on silica gel using dichloromethane/methanol (95:5) for the elution to give 0.042 g of 2(R)-[1(S)-(hydroxycarbamoyl)-4-phenylbutyl]-4-methyl-N-(2,5-dioxo-1-imidazolidinyl) valeramide in the form of a white solid.

MS: 405 (M+H)$^+$.

HPLC: Gradient elution using solvent A containing 5% solvent B increasing to 95% solvent B over 15 minutes; flow rate 1 ml/minute. Retention time: 7.77 minutes. Solvent A: $H_2O$/0.1% TFA; solvent B: $CH_3CN$/0.085% TFA. Column type: HYPERPEP 300A The 2(R)-[1(S)-(benzyloxycarbamoyl)-4-phenylbutyl]-4-methyl-N-(2,5-dioxo-1-imidazolidinyl)valeramide used as the starting material was prepared as follows:

(i) A solution of 5.0 g of (E)-2(R)-[1(S)-(tert-butoxycarbonyl)-4-phenyl-3-butenyl]-4-methylvaleric acid in 150 ml of iso-propyl alcohol was hydrogenated in the presence of 0.500 g of 5% palladium-on-carbon for 1 hour. The mixture was filtered and evaporated to give 4.8 g of 2(R)-[1(S)-(tert-butoxycarbonyl)-4-phenylbutyl]-4-methylvaleric acid in the form of a yellow oil.

(ii) A solution of 4.8 g of 2(R)-[1(S)-(tert-butoxycarbonyl)-4-phenylbutyl]-4-methylvaleric acid in 50 ml of dimethylformamide was cooled to 0° C. and treated with 2.80 g of pentafluorophenol and 2.65 g of 1-ethyl-3-(3-dimethylaminopropyl)carbodiimide hydrochloride. The mixture was stirred at 0° C. for 2.5 hours and then treated with 4.73 g of hydrazine monohydrochloride and 6.97 g of 4-methyl morpholine. The mixture was stirred for a further 18 hours at room temperature and then evaporated. The residue was dissolved in ethyl acetate and washed sequentially with 2M aqueous hydrogen chloride, 5% aqueous sodium hydrogen carbonate, water, and saturated aqueous sodium chloride. The organic layer was dried over anhydrous magnesium sulphate and evaporated. The residue was purified by flash column chromatography on silica gel using ethyl acetate/hexane (1:1) as the eluant to give 2.18 g of 2(R)-[1(S)-(tert-butoxycarbonyl)-4-phenylbutyl]-4-methylvalerohydrazide in the form of a pale yellow solid.

MS: 363 (M+H)$^+$.

(iii) A solution of 2.15 g of 2(R)-[1(S)-(tert-butoxycarbonyl)-4-phenylbutyl]-4-methylvalerohydrazide and 1.86 g of N-(benzyloxycarbonyl)-glycine in 8 ml of dimethylformamide was cooled to 0° C. and treated with 2.0 g of 1-ethyl-3-(3-dimethylaminopropyl)carbodiimide hydrochloride. The mixture was stirred overnight at room temperature, diluted with diethyl ether and washed sequentially with 2M aqueous hydrogen chloride, 5% aqueous sodium hydrogen carbonate, water, and saturated aqueous sodium chloride. The organic phase was dried over anhydrous magnesium sulphate and evaporated to give 2.96 g of 2(R)-[1(S)-(tert-butoxycarbonyl)-4-phenylbutyl]-2'-[N-(benzyloxycarbonyl)-glycinyl]-4-methylvalerohydrazide in the form of a white foam.

MS: 554 (M+H)$^+$.

(iv) A solution of 2.95 g of 2(R)-[1(S)-(tert-butoxycarbonyl)-4-phenylbutyl]-2'-[N-(benzyloxycarbonyl)-glycinyl]-4-methylvalerohydrazide in 30 ml of methanol was hydrogenated in the presence of 0.300 g of 5% palladium-on-carbon for 0.5 hours. The mixture was filtered and evaporated to give 2.2 g of 2(R)-[1(S)-(tert-butoxycarbonyl)-4-phenylbutyl]-2'-glycinyl-4-methylvalerohydrazide in the form of a white foam.

MS: 420 (M+H)$^+$.

(v) In a manner analagous to that described in Example 1, parts (vi)–(viii), but using 2(R)-[1(S)-(tert-butoxycarbonyl)-4-phenylbutyl]-2'-glycinyl-4-methylvalerohydrazide and O-benzylhydroxylamine in place of (E)-2(R)-[1(S)-(tert-butoxycarbonyl)-4-phenyl-3-butenyl]-2'-glycinyl-4-methylvalerohydrazide and O-(tetrahydro-2H-pyran-2(RS)-yl)hydroxylamine respectively there was obtained 2(R)-[1 (S)-(benzyloxycarbamoyl)-4-phenylbutyl]-4-methyl-N-(2, 5-dioxo-1-imidazolidinyl)valeramide in the form of a white solid.

MS: 495 (M+H)$^+$.

EXAMPLE 39

2(R)-[1(RS)-(Hydroxycarbamoyl)butyl]-4-methyl-N-(2,5-dioxo-1-imidazolidinyl)valeramide In a manner analagous to that described in Example 38 but using 2(R)-[1(RS)-(tert-butoxycarbonyl)butyl]-4-methylvaleric acid in place of 2(R)-[1(S)-(tert-butoxycarbonyl)-4-phenylbutyl]-4-methylvaleric acid there was obtained 2(R)-[1(RS)-(hydroxycarbamoyl)butyl]-4-methyl-N-(2,5-dioxo-1-imidazolidinyl)valeramide in the form of an off-white solid.

MS: 329 (M+H)$^+$.

EXAMPLE 40

(E)-2(R)-[1(S)-(Hydroxycarbamoyl)-4-phenyl-3-butenyl]-4-methyl-N-(3-methyl-2,5-dioxo-1-imidazolidinyl)valeramide A solution of 0.133 g of (E)-2(R)-[1(S)-[(tetrahydro-2 (RS)-pyranyloxy)carbamoyl]-4-phenyl-3-butenyl]-4-methyl-N-(3-methyl-2,5-dioxo-1-imidazolidinyl) valeramide in 5 ml of methanol was treated with 0.014 g of p-toluenesulphonic acid monohydrate. The mixture was stirred for 2.5 hours at room temperature and then evaporated. The residue was dissolved in ethyl acetate and washed with 5% aqueous sodium hydrogen carbonate. The organic layer was dried over anhydrous magnesium sulphate and evaporated. The residue was triturated with diethyl ether and hexane to give 0.049 g of (E)-2(R)-[1(S)-(Hydroxycarbamoyl)-4-phenyl-3-butenyl]-4-methyl-N-(3-methyl-2,5-dioxo-1-imidazolidinyl)valeramide in the form of a white solid.

MS: 417 (M+H)$^+$.

HPLC: Gradient elution using solvent A containing 5% solvent B increasing to 95% solvent B over 15 minutes; flow rate 1 ml/minute. Retention time: 8.33 minutes. Solvent A: $H_2O$/0.1% TFA; solvent B: $CH_3CN$/0.085% TFA. Column type: HYPERPEP 300A.

The (E)-2(R)-[1(S)-[(tetrahydro-2(RS)-pyranyloxy) carbamoyl]-4-phenyl-3-butenyl]-4-methyl-N-(3-methyl-2, 5-dioxo-1-imidazolidinyl)valeramide used as the starting material was prepared as follows:

(i) A solution of 0.386 g of (E)-2(S)-(tert-butoxycarbonyl)-1(R)-isobutyl-5-phenylpent-4-enyl-1,3,4-oxadiazol-2(3H)-one (prepared as described in Example 34, part (i)) in 10 ml of toluene was treated with 0.185 g of sarcosine ethyl ester hydrochloride and 0.42 ml of triethylamine and heated overnight at reflux temperature. The mixture was cooled to room temperature and evaporated and then washed sequentially with 2M aqueous hydrogen chloride, 5% aqueous sodium hydrogen carbonate, and saturated aqueous sodium chloride. Drying over anhydrous magnesium sulphate and evaporation gave 0.384 g of(E)-2 (R)-[1(S)-(tert-butoxycarbonyl)-4-phenyl-3-butenyl]-4-methyl-N-(3-methyl-2,5-dioxo-1-imidazolidinyl) valeramide in the form of a white solid.

MS: 458 $(M+H)^+$.

(ii) In an analogous manner to that described in Example 1, parts (vii)–(viii), but using (E)-2(R)-[1(S)-(tert-butoxycarbonyl)-4-phenyl-3-butenyl]-4-methyl-N-(3-methyl-2,5-dioxo-1-imidazolidinyl)valeramide in place of (E)-2(R)-[1(S)-(tert-butoxycarbonyl)-4-phenyl-3-butenyl]-4-methyl-N-(2,5-dioxo-1-imidazolidinyl)valeramide there was obtained (E)-2(R)-[1(S)-[(tetrahydro-2(RS)-pyranyloxy)carbamoyl]-4-phenyl-3-butenyl]-4-methyl-N-(3-methyl-2,5-dioxo-1-imidazolidinyl)valeramide in the form of a white solid.

MS: 501 $(M+H)^+$.

EXAMPLE 41

(E)-2(R)-[1(S)-(Hydroxycarbamoyl)-4-phenyl-3-butenyl]-4-methyl-N-(3-methyl-5-oxo-2-thioxo-1-imidazolidinyl)valeramide A solution of 0.209 g of (E)-2(R)-[1(S)-[(tetrahydro-2 (RS)-pyranyloxy)carbamoyl]-4-phenyl-3-butenyl]-4-methyl-N-(3-methyl-5-oxo-2-thioxo-1-imidazolidinyl) valeramide in 5 ml of methanol was treated with 0.020 g of p-toluenesulphonic acid monohydrate. The mixture was stirred for 2.5 hours at room temperature and then evaporated. The residue was dissolved in ethyl acetate and washed with 5% aqueous sodium hydrogen carbonate. The organic layer was dried over anhydrous magnesium sulphate and evaporated. The residue was triturated with diethyl ether/hexane (2:1) to give 0.048 g of (E)-2(R)-[1(S)-(Hydroxycarbamoyl)-4-phenyl-3-butenyl]-4-methyl-N-(3-methyl-5-oxo-2-thioxo-1-imidazolidinyl)valeramide in the form of a yellow solid.

MS: 433 $(M+H)^+$.

HPLC: Gradient elution using solvent A containing 5% solvent B increasing to 95% solvent B over 15 minutes; flow rate 1 ml/minute. Retention time: 9.26 minutes. Solvent A: $H_2O$/0.1% TFA; solvent B: $CH_3CN$/0.085% TFA. Column type: HYPERPEP 300A.

The (E)-2(R)-[1(S)-[(tetrahydro-2(RS)-pyranyloxy) carbamoyl]-4-phenyl-3-butenyl]-4-methyl-N-(3-methyl-5-oxo-2-thioxo-1-imidazolidinyl)valeramide used as the starting material was prepared as follows:

(i) A solution of 1.0 g of (E)-2(R)-[1(S)-(tert-butoxycarbonyl)-4-phenyl-3-butenyl]-4-methylvalerohydrazide in 10 ml of tetrahydrofuran was treated with 0.59 g of sodium carbonate. The mixture was cooled to 0° C. and 0.252 ml of thiophosgene was added.

The mixture was allowed to warm to room temperature and then stirred overnight. Evaporation gave a residue which was dissolved in ethyl acetate and washed in sequence with 0.5% aqueous sodium hydroxide and saturated aqueous sodium chloride. Drying of the organic phase over anhydrous magnesium sulphate and evaporation gave 1.02 g of (E)-2(S)-(tert-butoxycarbonyl)-1(R)-isobutyl-5-phenylpent-4-enyl-1,3,4-oxadiazol-2(3H)-thione in the form of an oil.

(ii) In an analogous manner to that described in Example 40, parts (i)–(ii), but using (E)-2(S)-(tert-butoxycarbonyl)-1(R)-isobutyl-5-phenylpent-4-enyl-1,3,4-oxadiazol-2(3H)-thione in place of (E)-2(S)-(tert-butoxycarbonyl)-1(R)-isobutyl-5-phenylpent-4-enyl-1,3,4-oxadiazol-2(3H)-one there was obtained (E)-2(R)-[1(S)-[(tetrahydro- 2(RS)-pyranyloxy)carbamoyl]-4-phenyl-3-butenyl]-4-methyl-N-(3-methyl-5-oxo-2-thioxo-1-imidazolidinyl)valeramide in the form of a yellow solid.

MS: 517 $(M+H)^+$.

EXAMPLE 42

N-(3,5-Dibenzyl-hexahydro-2,4,6-trioxo-1,3,5-triazin-1-yl)-2(R)-[1(S)-(hydroxycarbamoyl)-4-phenylbutyl]-4-methylvaleramide A solution of 0.211 g of (E)-N-(3,5-dibenzyl-hexahydro-2,4,6-trioxo-1,3,5-triazin-1-yl)-2(R)-[1(S)-(benzyloxycarbamoyl)-4-phenyl-3-butenyl]-4-methylvaleramide in 10 ml of methanol was hydrogenated in the presence of 0.020 g of 10% palladium-on-carbon for 6 hours. Filtration and evaporation of the filtrate gave a residue which was triturated with diethyl ether to give 0.009 g of N-(3,5-dibenzylhexahydro-2,4,6-trioxo-1,3,5-triazin-1-yl)-2(R)-[1(S)-(hydroxycarbamoyl)-4-phenylbutyl]-4-methylvaleramide in the form of a white solid.

MS: 614 $(M+H)^+$.

HPLC: Gradient elution using solvent A containing 5% solvent B increasing to 95% solvent B over 15 minutes; flow rate 1 ml/minute. Retention time: 12.88 minutes. Solvent A: $H_2O$/0.1% TFA; solvent B: $CH_3CN$/0.085% TFA. Column type: HYPERPEP 300A.

The (E)-N-(3,5-dibenzyl-hexahydro-2,4,6-trioxo-1,3,5-triazin-1-yl)-2(R)-[1(S)-(benzyloxycarbamoyl)-4-phenyl-3-butenyl]-4-methylvaleramide used as the starting material was prepared as follows:

(i) A solution of 0.737 g of (E)-2(S)-(tert-butoxycarbonyl)-1(R)-isobutyl-5-phenylpent-4-enyl-1,3,4-oxadiazol-2(3H)-one (prepared as described in Example 34, part (i)) in 10 ml of dimethylformamide was treated with 0.084 g of sodium hydride (60% suspension in mineral oil) under a nitrogen atmosphere and then heated to 50° C. for 0.5 hours. The mixture was cooled to 0° C. and treated dropwise with 0.528 ml of benzyl isocyanate. The mixture was warmed to room temperature and then heated to 80° C. for 0.5 hours. The mixture was cooled to room temperature again and evaporated. The residue was dissolved in iso-propyl alcohol, cooled to 0° C., and treated with several drops of acetic acid. The mixture was stirred for 0.5 hours and then chilled and filtered to collect the white precipitate that had formed. The solid was washed with cold iso-propyl alcohol and then hexane to give 0.703 g of (E)-N-(3,5-dibenzyl-hexahydro-2,4,6-trioxo-1,3,5-triazin-1-yl)-2(R)-[1 (S)-(tert-butyloxycarbonyl)-4-phenyl-3-butenyl]-4-methylvaleramide in the form of a white solid.

MS: 653 $(M+H)^+$.

(ii) In a manner analogous to that described in Example 34, parts (iv)–(v), but using (E)-N-(3,5-dibenzyl-hexahydro- 2,4,6-trioxo-1,3,5-triazin-1-yl)-2(R)-[1(S)-(tert-butyloxycarbonyl)-4-phenyl-3-butenyl]-4-methylvaleramide in place of (E)-2(R)-[1(S)-(tert-(butyloxy)carbonyl)-4-phenylbut-3-enyl]-N-(3-benzyl-2-oxo-1-imidazolinyl)-4-methylvaleramide there was obtained (E)-N-(3,5-dibenzyl-hexahydro-2,4,6-trioxo-1,3,5-triazin-1-yl)-2(R)-[1(S)-(benzyloxycarbamoyl)-4-phenyl-3-butenyl]-4-methylvaleramide in the form of a colourless oil

MS: 702 (M+H)+.

EXAMPLE 43

2(R)-[1(S)-(Hydroxycarbamoyl)-4-phenylbutyl]-4-methyl-N-(1-methyl-3,5-dioxo-1,2,4-triazolidin-4-yl)valeramide A solution of 0.229 g of 2(R)-[1(S)-(benzyloxycarbamoyl)-4-phenylbutyl]-4-methyl-N-(1-methyl-3,5-dioxo-1,2,4-triazolidin-4-yl)valeramide in 20 ml of methanol was hydrogenated in the presence of 0.02 g of 10% palladium-on-carbon for 5 hours. Filtration and evaporation gave a residue which was triturated with diethyl ether to give 0.135 g of 2(R)-[1(S)-(hydroxycarbamoyl)-4-phenylbutyl]-4-methyl-N-(1-methyl-3,5-dioxo-1,2,4-triazolidin-4-yl)valeramide in the form of a white solid.

MS: 420 (M+H)+.

HPLC: Gradient elution using solvent A containing 5% solvent B increasing to 95% solvent B over 15 minutes; flow rate 1 ml/minute. Retention time: 7.79 minutes. Solvent A: $H_2O$/0.1% TFA; solvent B: $CH_3CN$/0.085% TFA. Column type: HYPERPEP 300A.

The 2(R)-[1(S)-(benzyloxycarbamoyl)-4-phenylbutyl]-4-methyl-N-(1-methyl-3,5-dioxo-1,2,4-triazolidin-4-yl) valeramide used as the starting material was prepared as follows:

(i) A solution of 0.772 g of (E)-2(S)-(tert-butoxycarbonyl)-1(R)-isobutyl-5-phenylpent-4-enyl-1,3,4-oxadiazol-2(3H)-one (prepared as described in Example 34, part (i)) in 10 ml of toluene was treated with 0.116 ml of methyl hydrazine and heated at 80° C. for 5 hours. The mixture was diluted with ethyl acetate and washed in sequence with water, 5% aqueous sodium hydrogen carbonate and saturated aqueous sodium chloride and then dried over anhydrous magnesium sulphate. Evaporation gave 0.744 g of (E)-2(R)-[1(S)-(tert-butoxycarbonyl)-4-phenyl-3-butenyl]-4-methyl-2'-[(1-methylhydrazinyl)carbamoyl] valerohydrazide in the form of a white foam.

MS: 433 (M+H)+.

(ii) In an analogous manner to that described in Example 1, parts (vi)–(viii), but using (E)-2(R)-[1(S)-(tert-butoxycarbonyl)-4-phenyl-3-butenyl]-4-methyl-2'-[(1-methylhydrazinyl)carbamoyl]valerohydrazide and O-benzylhydroxylamine in place of (E)-2(R)-[1(S)-(tert-butoxycarbonyl)-4-phenyl-3-butenyl]-2 '-glycinyl-4-methylvalerohydrazide and O-(tetrahydro-2H-pyran-2(RS)-yl)hydroxylamine respectively there was obtained 2(R)-[1(S)-(benzyloxycarbamoyl)-4-phenylbutyl]-4-methyl-N-(1-methyl-3,5-dioxo-1,2,4-triazolidin-4-yl)valeramide in the form of a white solid.

MS: 508 (M+H)+.

EXAMPLE 44

2(R)-[1(S)-(Hydroxycarbamoyl)-4-phenylbutyl]-4-methyl-N-(2,4,6-trioxo-1,3,5-triazin-1-yl)valeramide A solution of 0.544 g of 2(R)-[1(S)-(benzyloxycarbamoyl)-4-phenylbutyl]-4-methyl-N-(2,4,6-trioxo-1,3,5-triazin-1-yl)valeramide in 20 ml of methanol was hydrogenated in the presence of 0.05 g of 10% palladium-on-carbon for 5 hours. Filtration, evaporation, and trituration of the residue with diethyl ether gave 0.105 g of 2(R)-[1(S)-(Hydroxycarbamoyl)-4-phenylbutyl]-4-methyl-N-(2,4,6-trioxo-1,3,5-triazin-1-yl)valeramide in the form of a white solid.

MS: 434 (M+H)+.

HPLC: Gradient elution using solvent A containing 5% solvent B increasing to 95% solvent B over 15 minutes; flow rate 1 ml/minute. Retention time: 7.57 minutes. Solvent A: $H_2O$/0.1% TFA; solvent B: $CH_3CN$/0.085% TFA. Column type: HYPERPEP 300A.

The 2(R)-[1(S)-(benzyloxycarbamoyl)-4-phenylbutyl]-4-methyl-N-(2,4,6-trioxo-1,3,5-triazin-1-yl)valeramide used as the starting material was prepared as follows:

(i) A solution of 0.830 g of N-(3,5-dibenzyl-hexahydro-2,4,6-trioxo-1,3,5-triazin-1-yl)-2(R)-[1(S)-(tert-butyloxycarbonyl)-4-phenyl-3-butenyl]-4-methylvaleramide in 50 ml of methanol and a few drops of acetic acid was hydrogenated in the presence of 0.08 g of palladium (II) hydroxide for 8 hours. The mixture was filtered and evaporated to give 0.588 g of 2(R)-[1(S)-(tert-butoxycarbonyl)-4-phenylbutyl]-4-methyl-N-(2,4,6-trioxo-1,3,5-triazin-1-yl)valeramide in the form of white solid.

MS: 475 (M+H)+.

(ii) In an analogous manner to that described in Example 34, parts (iv)–(v), but using 2(R)-[1(S)-(tert-butoxycarbonyl)-4-phenylbutyl]-4-methyl-N-(2,4,6-trioxo-1,3,5-triazin-1-yl)valeramide in place of (E)-2(R)-[1(S)-(tert-(butyloxy)carbonyl)-4-phenylbut-3-enyl]-N-(3-benzyl-2-oxo-1-imidazolinyl)-4-methylvaleramide there was obtained 2(R)-[1(S)-(benzyloxycarbamoyl)-4-phenylbutyl]-4-methyl-N-(2,4,6-trioxo-1,3,5-triazin-1-yl)valeramide in the form of a white solid.

MS: 524 (M+H)+.

EXAMPLE 45

2(R)-[1(S)-(Hydroxycarbamoyl)-4-phenylbutyl]-N-(1-isobutyl-3,5-dioxo-1,2,4-triazolidin-4-yl)-4-methylvaleramide In an analogous manner to that described in Example 43 but using isobutylhydrazine bis(toluenesulphonic acid) in the place of methyl hydrazine there was obtained 2(R)-[1(S)-(hydroxycarbamoyl)-4-phenylbutyl]-N-(1-isobutyl-3,5-dioxo-1,2,4-triazolidin-4-yl)-4-methylvaleramide in the form of a white solid.

MS: 462 (M+H)+.

HPLC: Gradient elution using solvent A containing 5% solvent B increasing to 95% solvent B over 15 minutes; flow rate 1 ml/minute. Retention time: 9.65 minutes. Solvent A: $H_2O$/0.1% TFA; solvent B: $CH_3CN$/0.085% TFA. Column type: SYMMETRY13.

EXAMPLE 46

2(R)-[1(S)-(Hydroxycarbamoyl)-4-phenylbutyl]-4-methyl-N-(3,5-dioxo-1-phenyl-1,2,4-triazolidin-4-yl)valeramide In an analogous manner to that described in Example 43 but using phenylhydrazine in the place of methyl hydrazine there was obtained 2(R)-[1(S)-(hydroxycarbamoyl)-4-phenylbutyl]-4-methyl-N-(3,5-dioxo-1-phenyl-1,2,4-triazolidin-4-yl)valeramide in the form of a white solid.

MS: 482 (M+H)+.

HPLC: Gradient elution using solvent A containing 5% solvent B increasing to 95% solvent B over 15 minutes; flow rate 1 ml/minute. Retention time: 9.88 minutes. Solvent A: $H_2O$/0.1% TFA; solvent B: $CH_3CN$/0.085% TFA. Column type: HYPERPEP 300A.

EXAMPLE 47

N-(1-Benzyl-3,5-dioxo-1,2,4-triazolidin-4-yl)-2(R)-[1(S)-(hydroxycarbamoyl)-4-phenylbutyl]-4-methyl-valeramide In an analogous manner to that described in Example 43 but using benzyl hydrazine in the place of methyl hydrazine there was obtained N-(1-benzyl-3,5-dioxo-1,2,4-triazolidin-4-yl)-2(R)-[1(S)-(hydroxycarbamoyl)-4-phenylbutyl]-4-methylvaleramide in the form of a white solid.

MS: 496 $(M+H)^+$.

HPLC: Gradient elution using solvent A containing 5% solvent B increasing to 95% solvent B over 15 minutes; flow rate 1 ml/minute. Retention time: 9.87 minutes. Solvent A: $H_2O$/0.1% TFA; solvent B: $CH_3CN$/0.085% TFA. Column type: HYPERPEP 300A.

EXAMPLE 48

2(R)-[4-Cyclohexyl-1(S)-(hydroxycarbamoyl)butyl]-N-(2,4,6-trioxo-1,3,5-triazin-1-yl)-4-methylvaleramide A solution of 0.107 g of 2(R)-[4-cyclohexyl-1(S)-(benzyloxycarbamoyl)butyl]-N-(2,4,6-trioxo-1,3,5-triazin-1-yl)-4-methylvaleramide in 5 ml of methanol was hydrogenated in the presence of 0.01 g of 10% palladium-on-carbon for 2 hours. The mixture was filtered and evaporated and the residue was triturated with diethyl ether to give 0.026 g of 2(R)-[4-cyclohexyl-1(S)-(hydroxycarbamoyl)butyl]-N-(2,4,6-trioxo-1,3,5-triazin-1-yl)-4-methylvaleramide in the form of a white solid.

MS: 440 $(M+H)^+$.

HPLC: Gradient elution using solvent A containing 5% solvent B increasing to 95% solvent B over 15 minutes; flow rate 1 ml/minute. Retention time: 8.97 minutes. Solvent A: $H_2O$/0.1% TFA; solvent B: $CH_3CN$/0.085% TFA. Column type: HYPERPEP 306A.

The 2(R)-[4-cyclohexyl-1(S)-(benzyloxycarbamoyl)butyl]-N-(2,4,6-trioxo-1,3,5-triazin-1-yl)-4-methylvaleramide used as the starting material was prepared as follows:

(i) A solution of 0.500 g of 2(R)-[1(S)-(tert-butoxycarbonyl)-4-phenylbutyl]-4-methyl-N-(2,4,6-trioxo-1,3,5-triazin-1-yl)valeramide (prepared as described in Example 44, part (i)) in 7 ml of glacial acetic acid was hydrogenated in the presence of 0.05 g of platinum (IV) oxide for 1.5 hours. Filtration and evaporation gave a residue which was purified by flash column chromatography on silica gel using ethyl acetate/hexane (1:1) as the eluant to give 0.129 g of 2(R)-[4-cyclohexyl-1(S)-(tert-butoxycarbonyl)butyl]-N-(2,4,6-trioxo-1,3,5-triazin-1-yl)-4-methylvaleramide in the form of a white solid.

MS: 481 $(M+H)^+$.

(ii) In an analogous manner to that described in Example 34, parts (iv)–(v), but using 2(R)-[4-cyclohexyl-1(S)-(tert-butoxycarbonyl)butyl]-N-(2,4,6-trioxo-1,3,5-triazin-1-yl)-4-methylvaleramide in place of (E)-2(R)-[1(S)-(tert-(butyloxy)carbonyl)-4-phenylbut-3-enyl]-N-(3-benzyl-2-oxo-1-imidazolinyl)-4-methylvaleramide there was obtained 2(R)-[4-cyclohexyl-1(S)-(benzyloxycarbamoyl)butyl]-N-(2,4,6-trioxo-1,3,5-triazin-1-yl)-4-methylvaleramide in the form of a white solid.

EXAMPLE 49

N-(3-Benzyl-2,5-dioxo-1-imidazolidinyl)-2(R)-[1(S)-(hydroxycarbamoyl)-4-phenylbutyl]-4-methylvaleramide A solution of 1.1 g of N-(3-benzyl-2,5-dioxo-1-imidazolidinyl)-2(R)-[1(S)-(benzyloxycarbamoyl)-4-phenyl-3-butenyl]-4-methylvaleramide in 20 ml of methanol was hydrogenated in the presence of 0.100 g of 10% palladium-on-carbon for 3 hours. The mixture was filtered and evaporated and the residue was triturated with diethyl ether to give 0.444 g of N-(3-benzyl-2,5-dioxo-1-imidazolidinyl)-2(R)-[1(S)-(hydroxycarbamoyl)-4-phenylbutyl]-4-methylvaleramide in the form of a white solid.

MS: 495 $(M+H)^+$.

HPLC: Gradient elution using solvent A containing 5% solvent B increasing to 95% solvent B over 15 minutes; flow rate 1 ml/minute. Retention time: 10.72 minutes. Solvent A: $H_2O$/0.1% TFA; solvent B: $CH_3CN$/0.085% TFA. Column type: HYPERPEP 300A.

The N-(3-benzyl-2,5-dioxo-1-imidazolidinyl)-2(R)-[1(S)-(benzyloxycarbamoyl)-4-phenyl-3-butenyl]-4-methylvaleramide used as the starting material was prepared as follows:

(i) A solution of 0.772 g of (E)-2(S)-(tert-butoxycarbonyl)-1(R)-isobutyl-5-phenylpent-4-enyl-1,3,4-oxadiazol-2(3H)-one (prepared as described in Example 34, part (i)) in 10 ml of toluene was treated with 0.387 g of N-benzyl glycine ethyl ester and 0.278 ml of triethylamine and heated overnight at reflux temperature. The mixture was cooled then diluted with ethyl acetate and washed in sequence with 5% aqueous citric acid, 5% aqueous sodium hydrogen carbonate and saturated aqueous sodium chloride and then dried over anhydrous magnesium sulphate. Evaporation gave 0.918 g of N-(3-Benzyl-2,5-dioxo-1-imidazolidinyl)-2(R)-[1(S)-(tert-butoxycarbonyl)-4-phenyl-3-butenyl]-4-methylvaleramide in the form of a white foam.

MS: 534 $(M+H)^+$.

(ii) In an analogous manner to that described in Example 34, parts (iv)–(v), but using N-(3-benzyl-2,5-dioxo-1-imidazolidinyl)-2(R)-[1(S)-(tert-butoxycarbonyl)-4-phenyl-3-butenyl]-4-methylvaleramide in place of (E)-2(R)-[1(S)-(tert-(butyloxy)carbonyl)-4-phenylbut-3-enyl]-N-(3-benzyl-2-oxo-1-imidazolinyl)-4-methylvaleramide there was obtained N-(3-benzyl-2,5-dioxo-1-imidazolidinyl)-2(R)-[1(S)-(benzyloxycarbamoyl)-4-phenyl-3-butenyl]-4-methylvaleramide in the form of a clear oil.

MS: 583 $(M+H)^+$.

EXAMPLE 50

2(R)-[1(S)-(Hydroxycarbamoyl)-4-phenylbutyl]-4-methyl-N-[2,5-dioxo-3-[(2-pyridyl)methyl]-1-imidazolidinyl]valeramide In a manner analogous to that described in Example 49 but using N-2-pyridylmethyl glycine ethyl ester in place of N-benzyl glycine ethyl ester there was obtained 2(R)-[1(S)-(hydroxycarbamoyl)-4-phenylbutyl]-4-methyl-N-[2,5-dioxo-3-[(2-pyridyl)methyl]-1-imidazolidinyl]valeramide in the form of a white solid.

MS: 496 $(M+H)^+$.

HPLC: Gradient elution using solvent A containing 5% solvent B increasing to 95% solvent B over 15 minutes; flow rate 1 ml/minute. Retention time: 7.82 minutes. Solvent A: H₂O/0.1% TFA; solvent B: CH₃CN/0.085% TFA. Column type: HYPERPEP 308A.

EXAMPLE 51

2(R)-[2-Benzamido-1(R)-(hydroxycarbamoyl)ethyl]-N-(4(S)-isopropyl-2,5-dioxo-1-imidazolidinyl)-4-methylvaleramide A solution of 0.22 g of 2(R)-[2-benzamido-1(R)-[(tetrahydro-2(RS)-pyranyloxy)carbamoyl]ethyl]-N-(4(S)-isopropyl-2,5-dioxo-1-imidazolidinyl)-4-methylvaleramide in 5 ml of methanol was treated with 0.022 g of p-toluenesulphonic acid monohydrate. The mixture was stirred for 2.5 hours and evaporated. The residue was dissolved in ethyl acetate and washed with 5% aqueous sodium hydrogen carbonate and then saturated aqueous sodium chloride. The organic fraction was dried over anhydrous magnesium sulphate and evaporated. The residue was triturated with diethyl ether to give 0.14 g of 2(R)-[2-benzamido-1(R)-(hydroxycarbamoyl)ethyl]-N-( 4(S)-isopropyl-2,5-dioxo-1-imidazolidinyl)-4-methylvaleramide in the form of a white solid.

MS: 462 (M+H)⁺.

HPLC: Gradient elution using solvent A containing 5% solvent B increasing to 95% solvent B over 15 minutes; flow rate 1 ml/minute. Retention time: 7.94 minutes. Solvent A: H₂O/0.1% TFA; solvent B: CH₃CN/0.085% TFA. Column type: HYPERPEP 300A.

The 2(R)-[2-benzamido-1(R)-[(tetrahydro-2(RS)-pyranyloxy)carbamoyl]ethyl]-N-(4(S)-isopropyl-2,5-dioxo-1-imidazolidinyl)-4-methylvaleramide used as the starting material was prepared as follows:

(i) 14.64 g of 2(R)-[1(R)-(tert-butoxycarbonyl)-2-phthalimido-ethyl]-4-methylvaleric acid cyclohexylamine salt was partitioned between 40 ml of 1N sulphuric acid and 150 ml of ethyl acetate. The organic layer was washed three times with aqueous saturated sodium chloride and then dried over anhydrous magnesium sulphate. Evaporation gave an oil which was dissolved in 120 ml of ethanol and treated with 7.3 ml of hydrazine hydrate. The mixture was stirred at room temperature for 2 hours and the white precipitate that formed was removed by filtration. The filtrate was evaporated and the resulting residue was dissolved in 150 ml of dichloromethane and 15 ml of acetic acid. The mixture was stirred at room temperature for 1 hour and then filtered and evaporated to give 13.62 g of 2(R)-aminoethyl-[1(R)-(tert-butoxycarbonyl)]-4-methylvaleric acid acetic acid salt as a yellow oil.

(ii) A solution of 12.6 g of 2(R)-aminoethyl-[1(R)-(tert-butoxycarbonyl)]-4-methylvaleric acid acetic acid salt in 120 ml of dichloromethane was cooled to −10° C. under a nitrogen atmosphere and treated with 16 ml of triethylamine and a solution of 5.5 ml of benzoyl chloride dissolved in 20 ml of dichloromethane. After stirring at −10° C. for 0.5 hours the mixture was allowed to warm to room temperature and evaporated. The residue was dissolved in ether and filtered and then washed in sequence with 2M aqueous hydrogen chloride, water and 3×50 ml portions of 2% aqueous sodium hydrogen carbonate. The ether layer was diluted with hexane and washed again with 3×50 ml portions of 2% aqueous sodium hydrogen carbonate. The combined aqueous sodium hydrogen carbonate extracts were acidified with concentrated aqueous hydrogen chloride and then washed with ether. The ether layer was subsequently washed with water (2×) and saturated sodium chloride and then dried over anhydrous magnesium sulphate. Evaporation gave a residue which was purified by flash column chromatography on silica gel using ether/ hexane (1:1) for the elution to give 1.97 g of 2(R)-[2-benzamido-1(R)-(tert-butoxycarbonyl)ethyl]-4-methylvaleric acid in the form of a clear oil.

MS: 364 (M+H)⁺.

(iii) A solution of 1.9 g of 2(R)-[2-benzamido-1(R)-(tert-butoxycarbonyl)ethyl]-4-methylvaleric acid in 3 ml of dry dimethylformamide was cooled to 0° C. under a nitrogen atmosphere and treated with 2.61 g of benzyl carbazate and 1.20 g of 1-ethyl-3-(3-dimethylaminopropyl)carbodiimide hydrochloride. The mixture was allowed to warm to room temperature and then stirred overnight. The mixture was diluted with ethyl acetate and washed in sequence with water, 2M aqueous hydrogen chloride, water, 5% aqueous sodium hydrogen carbonate and saturated aqueous sodium chloride. Drying over anhydrous magnesium sulphate and evaporation gave 2.68 g of 2(R)-[2-benzamido-1(R)-(tert-butoxycarbonyl)ethyl]-2'-benzyloxycarbonyl-4-methylvalerohydrazide in the form of a white foam.

MS: 512 (M+H)⁺.

(iv) A solution of 0.81 g of 2(R)-[2-benzamido-1(R)-(tert-butoxycarbonyl)ethyl]-2'-benzyloxycarbonyl-4-methylvalerohydrazide in 10 ml of ethanol was hydrogenated in the presence of 0.080 g of 10% palladium-on-carbon for 4 hours. The catalyst was removed by filtration and evaporation gave 0.59 g of 2(R)-[2-benzamido-1(R)-(tert-butoxycarbonyl)ethyl]-4-methylvalerohydrazide in the form of a white solid.

MS: 378 (M+H)⁺.

(v) A solution of 0.55 g of 2(R)-[2-benzamido-1(R)-(tert-butoxycarbonyl)ethyl]-4-methylvalerohydrazide in 5 ml of pyridine was treated with 0.22 ml of methyl-(S)-(−)-2-isocyanato-3-methyl butyrate and stirred at room temperature for 2 hours. A further 0.044 ml of the isocyanate was added and stirring continued overnight. The mixture was evaporated and the residue was dissolved in ethyl acetate and washed in sequence with 2M aqueous hydrogen chloride, water, 5% aqueous sodium hydrogen carbonate and saturated aqueous sodium chloride. The ethyl acetate layer was dried over anhydrous magnesium sulphate and evaporated to give 0.85 g of 2(R)-[2-benzamido-1(R)-(tert-butoxycarbonyl)ethyl]-4-methyl-2'-[2(S)-(methyl-3-methyl butyrate)carbamoyl]valerohydrazide in the form of a white foam.

MS: 535 (M+H)⁺.

(vi) A solution of 0.78 g of 2(R)-[2-benzamido-1(R)-(tert-butoxycarbonyl)ethyl]-4-methyl-2'-[2(S)-(methyl-3-methyl butyrate)carbamoyl]valerohydrazide in 20 ml of toluene was treated with 0.2 ml of triethylamine and heated at reflux overnight. The mixture was diluted with ethyl acetate and washed in sequence with 2M aqueous hydrogen chloride, water, 5% aqueous sodium hydrogen carbonate and saturated aqueous sodium chloride. The ethyl acetate layer was dried over anhydrous magnesium sulphate and evaporated to give a residue which was purified by flash column chromatography on silica gel using ethyl acetate/hexane (2:1) for the elution to give 0.61 g of 2(R)-[2-benzamido-1(R)-(tert-butoxycarbonyl)ethyl]-N-(4(S)-isopropyl-2,5-dioxo-1-imidazolidinyl)-4-methylvaleramide in the form of a clear oil.

MS: 503 (M+H)⁺.

(vii) In a manner analagous to that described in Example 1, parts (vii)–(viii), but using 2(R)-[2-benzamido-1(R)-(tert-butoxycarbonyl)ethyl]-N-(4(S)-isopropyl-2,5-dioxo-1-imidazolidinyl)-4-methylvaleramide in place of (E)-2(R)-[1(S)-(tert-butoxycarbonyl)-4-phenyl-3-butenyl]-4-methyl-N-(2,5-dioxo-1-imidazolidinyl)valeramide there was obtained 2(R)-[2-benzamido-1(R)-[(tetrahydro-2(RS)-pyranyloxy)carbamoyl]ethyl]-N-(4(S)-isopropyl-2,5-dioxo-1-imidazolidinyl)-4-methylvaleramide in the form of a white solid.

MS: 462 (M+H)$^+$.

EXAMPLE 52

-[3-Benzyl-4(S)-(hydroxymethyl)-2,5-dioxo-1-imidazolidinyl]-2(R)-[1(S)-(hydroxycarbamoyl)-4-phenylbutyl]-4-methylvaleramide A solution of 0.077g of (E)-N-[3-benzyl-4(S)-(hydroxymethyl)-2,5-dioxo-1-imidazolidinyl]-2(R)-[1(S)-(benzyloxycarbamoyl)-4-phenyl-3-butenyl]-4-methylvaleramide in 10 ml of methanol was hydrogenated in the presence of 0.010 g of 10% palladium-on-carbon for 3 hours. The catalyst was removed by filtration and evaporation followed by trituration with diethyl ether gave 0.020 g of N-[3-benzyl-4(S)-(hydroxymethyl)-2,5-dioxo-1-imidazolidinyl]-2(R)-[1(S)-(hydroxycarbamoyl)-4-phenylbutyl]-4-methylvaleramide in the form of a white solid.

MS: 525 (M+H)$^+$.

HPLC: Gradient elution using solvent A containing 5% solvent B increasing to 95% solvent B over 15 minutes; flow rate 1 ml/minute. Retention time: 10.12 minutes. Solvent A: H$_2$O/0.1% TFA; solvent B: CH$_3$CN/0.085% TFA. Column type: HYPERPEP 300A.

The (E)-N-[3-benzyl-4(S)-(hydroxymethyl)-2,5-dioxo-1-imidazolidinyl]-2(R)-[1(S)-(benzyloxycarbamoyl)-4-phenyl-3-butenyl]-4-methylvaleramide used as the starting material was prepared in an analogous manner to that described in Example 49, parts (i)–(ii), but using N-benzyl-(L)-serine methyl ester in the place of N-benzyl glycine ethyl ester.

MS: 613 (M+H)$^+$.

EXAMPLE 53

N-(3-Benzyl-2,4,5-trioxo-1-imidazolidinyl]-2(R)-[1(S)-(hydroxycarbamoyl)-4-phenylbutyl]-4-methylvaleramide A solution of 0.076 g of (E)-2(R)-[1(S)-(benzyloxycarbamoyl)-4-phenyl-3-butenyl]-N-(3-benzyl-2,4,5-trioxo-1-imidazolidinyl]-4-methylvaleramide in 5 ml of methanol was hydrogenated in the presence of 0.025 g of 5% palladium-on-carbon for 6 hours. The catalyst was removed by filtration and the mixture evaporated. The residue was redissolved in 5 ml of methanol and hydrogenated in the presence of 0.020 g of 10% palladium-on-carbon for 3 hours. The catalyst was removed by filtration and the solvent was evaporated and the residue was then triturated with hexane and then with diethyl ether to give 0.022 g of N-(3-benzyl-2,4,5-trioxo-1-imidazolidinyl]-2(R)-[1(S)-(hydroxycarbamoyl)-4-phenylbutyl]-4-methylvaleramide in the form of a white solid.

MS: 509 (M+H)$^+$.

HPLC: Gradient elution using solvent A containing 5% solvent B increasing to 95% solvent B over 15 minutes; flow rate 1 ml/minute. Retention time: 11.65 minutes. Solvent A: H$_2$O/0.1% TFA; solvent B: CH$_3$CN/0.085% TFA. Column type: HYPERPEP 300A.

The (E)-2(R)-[1(S)-(benzyloxycarbamoyl)-4-phenyl-3-butenyl]-N-(3-benzyl-2,4,5-trioxo-1-imidazolidinyl]-4-methylvaleramide used as the starting material was prepared as follows:

(i) A solution of 1.09 g of (E)-2(R)-[1(S)-(tert-butoxycarbonyl)-4-phenyl-3-butenyl]-4-methylvalerohydrazide pentafluorophenol salt in 5 ml of pyridine was treated with 0.25 ml of benzyl isocyanate under a nitrogen atmosphere. The mixture was stirred for 2 hours at room temperature and then evaporated. The residue was dissolved in ethyl acetate and washed in sequence with 2M aqueous hydrogen chloride, water, 5% aqueous sodium hydrogen carbonate and saturated aqueous sodium chloride. The organic layer was dried over anhydrous magnesium sulphate and evaporated to give a yellow oil. This was dissolved in ethyl acetate and washed twice with 0.5% aqueous sodium hydroxide and then with saturated aqueous sodium chloride. The organic layer was again dried over anhydrous magnesium sulphate and evaporated to give 0.946 g of (E)-2(R)-[1(S)-(tert-butoxycarbonyl)-4-phenyl-3-butenyl]-2'-(benzyl)carbamoyl-4-methylvalerohydrazide in the form of a pale yellow foam.

MS: 987 (2M+H)$^+$.

(ii) A solution of 0.94 g of (E)-2(R)-[1(S)-(tert-butoxycarbonyl)-4-phenyl-3-butenyl]-2'-(benzyl)carbamoyl-4-methylvalerohydrazide in 10 ml of dichloromethane was cooled to 0° C. under a nitrogen atmosphere and treated with 0.4 ml of pyridine and 0.174 ml of oxalyl chloride. The mixture was stirred at 0° C. for 2 hours and then allowed to warm to room temperature overnight. The mixture was washed in sequence with 2M aqueous hydrogen chloride, water, 5% aqueous sodium hydrogen carbonate, and saturated aqueous sodium chloride. The organic fraction was dried over anhydrous magnesium sulphate and evaporated. The solid residue was recrystallized from ethyl acetate to give 0.69 g of (E)-2(R)-[1(S)-(tert-butoxycarbonyl)-4-phenyl-3-butenyl]-N-(3-benzyl-2,4,5-trioxo-1-imidazolidinyl]-4-methylvaleramide in the form of a white solid.

MS: 492 (M+H-tBu)$^+$.

(iii) In an analogous manner to that described in Example 1, parts (vi)–(viii), but using (E)-2(R)-[1(S)-(tert-butoxycarbonyl)-4-phenyl-3-butenyl]-N-(3-benzyl-2,4,5-trioxo-1-imidazolidinyl]-4-methylvaleramide and O-benzylhydroxylamine in place of (E)-2(R)-[1(S)-(tert-butoxycarbonyl)-4-phenyl-3-butenyl]-2'-glycinyl-4-methylvalerohydrazide and O-(tetrahydro-2H-pyran-2(RS)-yl)hydroxylamine respectively there was obtained (E)-2(R)-[1(S)-(benzyloxycarbamoyl)-4-phenyl-3-butenyl]-N-(3-benzyl-2,4,5-trioxo-1-imidazolidinyl]-4-methylvaleramide in the form of a white solid.

MS: 597 (M+H)$^+$.

EXAMPLE 54

(E)-N-(Tetrahydro-3-oxo-1,2,5-thiadiazol-2-yl)-2(R)-[1(S)-(hydroxycarbamoyl)-4-phenyl-3-butenyl]-4-methylvaleramide S,S-dioxide A solution of 0.082 g of (E)-N-(tetrahydro-3-oxo-1,2,5-thiadiazol-2-yl)-2(R)-[1(S)-[(tetrahydro-2(RS)-pyranyloxy)carbamoyl)-4-phenyl-3-butenyl]-4-methylvaleramide S,S-dioxide in 10 ml of methanol was treated with 0.008 g of p-toluenesulphonic acid monohydrate and stirred at room temperature for 2 hours. Evaporation of the solvent gave a residue which was purified by flash column chromatography on silica gel using methanol/dichloromethane (1:9) for the elution. Trituration of the purified material with diethyl ether gave 0.013 g of (E)-N-(tetrahydro-3-oxo-1,2,5thiadiazol-2-yl)-2(R)-[1(S)-(hydroxycarbamoyl)-4-phenyl-3-butenyl]-4-methylvaleramide S,S-dioxide in the form of a white solid.

MS: 439 (M+H)$^+$.

HPLC: Gradient elution using solvent A containing 5% solvent B increasing to 95% solvent B over 15 minutes; flow rate 1 ml/minute. Retention time: 10.89 minutes. Solvent A: H$_2$O/0.1% TFA; solvent B: CH$_3$CN/0.085% TFA. Column type: HYPERPEP 300A.

The (E)-N-(tetrahydro-3-oxo-1,2,5-thiadiazol-2-yl)-2(R)-[1(S)-[(tetrahydro-2(RS)-pyranyloxy)carbamoyl)-4-phenyl-3-butenyl]-4-methylvaleramide S,S-dioxide used as the starting material was prepared as follows:

(i) A solution of 1.08 g of (E)-2(R)-[1(S)-(tert-butoxycarbonyl)-4-phenyl-3-butenyl]-4-methylvalerohydrazide in 10 ml of dichloromethane was cooled to 0° C. under a nitrogen atmosphere and treated with 0.8 ml of pyridine and a solution of 1.5 g of N-(chlorosulphonyl)-glycine methyl ester in 5 ml of dichloromethane. The mixture was warmed to room temperature and stirred for 3 hours. The mixture was then diluted with ethyl acetate and washed with 2M aqueous hydrogen chloride and saturated aqueous sodium chloride. The organic layer was dried over anhydrous magnesium sulphate and evaporated and the residue was purified by flash column chromatography on silica gel using hexane/ethyl acetate (3:2) for the elution to give 0.831 g of methyl(E)-2-[[2-[2(R)-[1(S)-(tert-butoxycarbonyl)-4-phenyl-3-butenyl]-4-methylvaleryl]hydrazino]sulphonamido]acetate in the form of a solid.

MS: 512 (M+H)$^+$.

(ii) A solution of 0.431 g of methyl(E)-2-[[2-[2(R)-[1(S)-(tert-butoxycarbonyl)-4-phenyl-3-butenyl]-4-methylvaleryl]hydrazino]sulphonamido]acetate in 10 ml of tetrahydrofuran and 5 ml of methanol was treated with 0.040 g of lithium hydroxide monohydrate and the mixture was left to stir overnight. A further 0.020 g of lithium hydroxide monohydrate was added and stirring continued for 4 hours. The mixture was then diluted with water, acidified using 2M aqueous hydrogen chloride, and extracted with ethyl acetate. The ethyl acetate fraction was dried over anhydrous magnesium sulphate and evaporated to give 0.462 g of methyl (E)-2-[[2-[2(R)-[1(S)-(tert-butoxycarbonyl)-4-phenyl-3-butenyl]-4-methylvaleryl]hydrazino]sulphonamido]acetic acid as an oil.

MS: 498 (M+H)$^+$.

(iii) A solution of 0.462 g of methyl(E)-2-[[2-[2(R)-[1(S)-(tert-butoxycarbonyl)-4-phenyl-3-butenyl]-4-methylvaleryl]hydrazino]sulphonamido]acetic acid in 10 ml of dimethylformamide was treated with 0.177 g of 1-ethyl-3-(3-dimethylaminopropyl)carbodiimide hydrochloride and stirred at room temperature for 2.5 hours. The mixture was evaporated and the residue was dissolved in ethyl acetate and then washed with 1M aqueous hydrogen chloride and saturated aqueous sodium chloride. The ethyl acetate layer was dried over anhydrous magnesium sulphate and evaporated to give a residue which was purified by flash column chromatography on silica gel using ethyl acetate/hexane (1:1) for the elution to give 0.205 g of (E)-2(R)-[1(S)-[(tert-butoxycarbonyl)-4-phenyl-3-butenyl]-4-methyl-N-(tetrahydro-3-oxo-1,2,5-thiadiazol-2-yl)-valeramide S,S-dioxide in the form of a white solid.

MS: 480 (M+H)$^+$.

(iv) In an analogous manner to that described in Example 1, parts (vi)–(viii), but using (E)-2(R)-[1(S)-[(tert-butoxycarbonyl)-4-phenyl-3-butenyl]-4-methyl-N-(tetrahydro-3-oxo-1,2,5-thiadiazol-2-yl)-valeramide S,S-dioxide in place of (E)-2(R)-[1(S)-(tert-butoxycarbonyl)-4-phenyl-3-butenyl]-2'-glycinyl-4-methylvalerohydrazide there was obtained (E)-N-(tetrahydro-3-oxo-1,2,5-thiadiazol-2-yl)-2(R)-[1(S)-[(tetrahydro-2(RS)-pyranyloxy)carbamoyl)-4-phenyl-3-butenyl]-4-methylvaleramide S,S-dioxide in the form of a white solid.

MS: 523 (M+H)$^+$.

EXAMPLE 55

N-(Tetrahydro-3-oxo-1,2,5-thiadiazol-2-yl)-2(R)-[1(S)-(hydroxycarbamoyl)-4-phenylbutyl]-4-methylvaleramide S,S-dioxide A solution of 0.049 g of N-(tetrahydro-3-oxo-1,2,5-thiadiazol-2-yl)-2(R)-[1(S)-(benzyloxycarbamoyl)-4-phenyl-3-butenyl]-4-methylvaleramide S,S-dioxide in 10 ml of methanol was hydrogenated in the presence of 0.005 g of 10% palladium-on-carbon for 2.5 hours. The catalyst was removed by filtration and the solvent was evaporated to give a residue which was triturated with diethyl ether to give 0.033 g of N-(tetrahydro-3-oxo-1,2,5-thiadiazol-2-yl)-2(R)-[1(S)-(hydroxycarbamoyl)-4-phenylbutyl]-4-methylvaleramide S,S-dioxide in the form of a white solid.

MS: 441 (M+H)$^+$.

HPLC: Gradient elution using solvent A containing 5% solvent B increasing to 95% solvent B over 15 minutes; flow rate 1 ml/minute. Retention time: 8.72 minutes. Solvent A: H$_2$O/0.1% TFA; solvent B: CH$_3$CN/0.085% TFA. Column type: HYPERPEP 300A.

The N-(tetrahydro-3-oxo-1,2,5-thiadiazol-2-yl)-2(R)-[1(S)-(benzyloxycarbamoyl)-4-phenyl-3-butenyl]-4-methylvaleramide S,S-dioxide used as the starting material was prepared as follows:

In an analogous manner to that described in Example 1, parts (vi)–(viii), but using (E)-2(R)-[1(S)-[(tert-butoxycarbonyl)-4-phenyl-3-butenyl]-4-methyl-N-(tetrahydro-3-oxo-1,2,5-thiadiazol-2-yl)-valeramide S,S-dioxide (prepared as described in Example 54, part (iii)) and O-benzylhydroxylamine in place of (E)-2(R)-[1(S)-(tert-butoxycarbonyl)-4-phenyl-3-butenyl]-2'-glycinyl-4-methylvalerohydrazide and O-(tetrahydro-2H-pyran-2(RS)-yl)hydroxylamine respectively there was obtained N-(tetrahydro- 3-oxo-1,2,5-thiadiazol-2-yl)-2(R)-[1(S)-(benzyloxycarbamoyl)-4-phenyl-3-butenyl]-4-methylvaleramide S,S-dioxide in the form of a white solid.

MS: 529 (M+H)$^+$.

EXAMPLE 56

(E)-N-(3-Benzyl-2,4,5-trioxo-1-imidazolidinyl]-2(R)-[1(S)-(hydroxycarbamoyl)-4-phenyl-3-butenyl]-4-methylvaleramide A solution of 0.045 g of (E)-N-(3-benzyl-2,4,5-trioxo-1-imidazolidinyl]-2(R)-[1(S)-[(tetrahydro-2(RS)-pyranyloxy)carbamoyl]-4-phenyl-3-butenyl]-4-methylvaleramide in 2 ml of methanol was treated with 0.010 g of p-toluenesulphonic acid monohydrate and stirred at room temperature for 2 hours. The mixture was diluted with ethyl acetate and washed in sequence with 5% aqueous sodium hydrogen carbonate and saturated aqueous sodium chloride. The organic layer was dried over anhydrous magnesium sulphate and evaporated to give a residue which was triturated with diethyl ether to give 0.032 g of (E)-N-(3-benzyl- 2,4,5-trioxo-1-imidazolidinyl]-2(R)-[1(S)-(hydroxycarbamoyl)-4-phenyl-3-butenyl]-4-methylvaleramide in the form of a white solid.

MS: 507 (M+H)+.

HPLC: Gradient elution using solvent A containing 5% solvent B increasing to 95% solvent B over 15 minutes; flow rate 1 ml/minute. Retention time: 12.35 minutes. Solvent A: H$_2$O/0.1% TFA; solvent B: CH$_3$CN/0.085% TFA. Column type: HYPERSIL C19 BDS.

The (E)-N-(3-benzyl-2,4,5-trioxo-1-imidazolidinyl]-2(R)-[1(S)-[(tetrahydro-2(RS)-pyranyloxy)carbamoyl]-4-phenyl-3-butenyl]-4-methylvaleramide used as the starting material was prepared as follows:

In an analogous manner to that described in Example 1, parts (vi)–(viii), but using (E)-2(R)-[1(S)-(tert-butoxycarbonyl)-4-phenyl-3-butenyl]-N-(3-benzyl-2,4,5-trioxo-1-imidazolidinyl]-4-methylvaleramide (prepared as described in Example 53, part (ii)) in place of (E)-2(R)-[1(S)-(tert-butoxycarbonyl)-4-phenyl-3-butenyl]-2'-glycinyl-4-methylvalerohydrazide there was obtained (E)-N-(3-benzyl-2,4,5-trioxo-1-imidazolidinyl]-2(R)-[1(S)-[(tetrahydro-2(RS)-pyranyloxy)carbamoyl]-4-phenyl-3-butenyl]-4-methylvaleramide in the form of a white solid.

MS: 591 (M+H)+.

EXAMPLE 57

2(R)-[1(S)-(Hydroxycarbamoyl)-4-phenylbutyl]-N-[3-[2-(dimethylamino)ethyl]-2,5-dioxo-1-imidazolidinyl]-4-methylvaleramide A solution of 0.061 g of 2(R)-[1(S)-(benzyloxycarbamoyl)-4-phenylbutyl]-N-[3-[2-(dimethylamino)ethyl]-2,5-dioxo-1-imidazolidinyl]-4-methylvaleramide in 10 ml of methanol was hydrogenated in the presence of 0.005 g of 10% palladium-on-carbon for 3 hours. The catalyst was removed by filtration and evaporation gave 0.048 g of 2(R)-[1(S)-(Hydroxycarbamoyl)-4-phenylbutyl]-N-[3-[2-(dimethylamino)ethyl]-2,5-dioxo-1-imidazolidinyl]-4-methylvaleramide in the form of a white solid.

MS: 476 (M+H)+.

HPLC: Gradient elution using solvent A containing 5% solvent B increasing to 95% solvent B over 15 minutes; flow rate 1 ml/minute. Retention time: 7.63 minutes. Solvent A: H$_2$O/0.1% TFA; solvent B: CH$_3$CN/0.085% TFA. Column type: HYPERPEP 300A.

The 2(R)-[1(S)-(benzyloxycarbamoyl)-4-phenylbutyl]-N-[3-[2-(dimethylamino)ethyl]-2,5-dioxo-1-imidazolidinyl]-4-methylvaleramide used as the starting material was prepared as follows:

(i) A solution of 1.5 g of (E)-2(S)-(tert-butoxycarbonyl)-1(R)-isobutyl-5-phenylpent-4-enyl-1,3,4-oxadiazol-2(3H)-one (prepared as described in Example 34, part (i)) in 40 ml of toluene was treated with 1.1 g of N-[2-[[(1,1-dimethylethoxy)carbonyl]amino]ethyl]-glycine methyl ester and 1.1 ml of triethylamine and heated at reflux overnight. The mixture was cooled and diluted with ethyl acetate and then washed in sequence with 5% aqueous citric acid, 5% aqueous sodium hydrogen carbonate, and saturated aqueous sodium chloride. The organic layer was dried over anhydrous magnesium sulphate and evaporated to give a residue which was purified by flash column chromatography on silica gel using ethyl acetate/hexane (3:1) for the elution to give 0.475 g of (E)-2(R)-[1(S)-(tert-butoxycarbonyl)-4-phenyl-3-butenyl]-N-[2-[[(1,1-dimethylethoxy)carbonyl]amino]ethyl]-2,5-dioxo-1-imidazolidinyl]-4-methylvaleramide in the form of a white solid.

MS: 609 (M+Na)+.

(ii) A solution of 0.150 g of (E)-2(R)-[1(S)-(tert-butoxycarbonyl)-4-phenyl-3-butenyl]-N-[2-[[(1,1-dimethylethoxy)carbonyl]amino]ethyl]-2,5-dioxo-1-imidazolidinyl]-4-methylvaleramide in 2 ml of dichloromethane was treated with 2 ml of trifluoroacetic anhydride and stirred at room temperature under a nitrogen atmosphere for 2 hours. The solvent was removed by evaporation and the residue taken up in toluene. The toluene was removed by evaporation and this procedure was repeated to give 0.140 g of (E)-N-(2-aminoethyl)-2(R)-[1(S)-(carboxy)-4-phenyl-3-butenyl]-2,5-dioxo-1-imidazolidinyl]-4-methylvaleramide in the form of a white solid.

MS: 431 (M+H)+.

(iii) A solution of 0.140 g of (E)-N-(2-aminoethyl)-2(R)-[1(S)-(carboxy)-4-phenyl-3-butenyl]-2,5-dioxo-1-imidazolidinyl]-4-methylvaleramide in 10 ml of methanol was treated with 0.075 ml of a 30% w/v solution of formaldehyde in water and then hydrogenated overnight in the presence of 0.010 g of 10% palladium-on-carbon. A further 0.5 ml of a 30% w/v solution of formaldehyde in water was added to the mixture and hydrogenation continued for 24 hours in the presence of a further 0.010 g of 10% palladium-on-carbon. The catalyst was removed by filtration and the solvent was evaporated to give 0.151 g of 2(R)-[1(S)-(carboxy)-4-phenylbutyl]-N-[3-[2-(dimethylamino)ethyl]-2,5-dioxo-1-imidazolidinyl]-4-methylvaleramide in the form of a white solid.

MS: 461 (M+H)+.

(iv) A solution of 0.151 g of 2(R)-[1(S)-(carboxy)-4-phenylbutyl]-N-[3-[2-(dimethylamino)ethyl]-2,5-dioxo-1-imidazolidinyl]-4-methylvaleramide and 0.157 g of O-benzylhydroxylamine in 0.25 ml of dimethylformamide was treated with 0.054 mg of 1-ethyl-3-(3-dimethylaminopropyl)-carbodiimide hydrochloride and stirred at room temperature for 4 hours. The mixture was diluted with ethyl acetate and washed with 5% aqueous sodium hydrogen carbonate and saturated aqueous sodium chloride. The organic layer was dried over anhydrous magnesium sulfate and evaporated to give a residue which was purified by flash column chromatography on silica gel, using methanol/dichloromethane (5:95) for the elution, to give 0.061 g of 2(R)-[1(S)-(benzyloxycarbamoyl)-4-phenylbutyl]-N-[3-[2-(dimethylamino)ethyl]-2,5-dioxo-1-imidazolidinyl]-4-methylvaleramide in the form of a white foam.

MS: 566 (M+H)+.

EXAMPLE 58

1-(8-Acetyl-2,4-dioxo-1,3,8-triazaspiro[4.5]decan-3-yl)-2(R)-[1(S)-(hydroxycarbamoyl)-4-phenylbutyl]-4-methylvaleramide In a manner analogous to that described in Example 3 from 0.106 g of 1-(8-acetyl-2,4-dioxo-1,3,8-triazaspiro[4.5]decan-3-yl)-2(R)-[1(S)-[(tetrahydro-2(RS)-pyranyloxy)carbamoyl]-4-phenylbutyl]-4-methylvalerohydrazide there was obtained 0.035 g of 1-(8-acetyl-2,4-dioxo-1,3,8-triazaspiro[4.5]-decan-3-yl)-2(R)-[1(S)-(hydroxycarbamoyl)-4-phenylbutyl]-4-methylvaleramide in the form of an off-white solid.

MS: 516 (M+H)+.

HPLC: Gradient elution using solvent A containing 5% solvent B increasing to 95% solvent B over 15 minutes; flow rate 1 ml/minute. Retention time: 8.07 minutes. Solvent A: $H_2O/0.1\%$ TFA; solvent B: $CH_3CN/0.085\%$ TFA. Column type: HYPERPEP 300A.

The 1-(8-acetyl-2,4-dioxo-1,3,8-triazaspiro[4.5]decan-3-yl)-2(R)-[1(S)-[(tetrahydro-2(RS)-pyranyloxy)carbamoyl]-4-phenylbutyl]-4-methylvaleramide used as the starting material was prepared in a manner analogous to that described in Example 24, parts (i) and (ii) using acetic acid in place of N-(benzyloxycarbonyl)glycine in part (ii) and Example 1, parts (vii) and (viii).

MS: 600 (M+H)+.

EXAMPLE 59

2(R)-[1(S)-(Hydroxycarbamoyl)-4-phenylbutyl]-4-methyl-N-(8-methyl-2,4-dioxo-1,3,8-triazaspiro[4.5]decan-3-yl)valeramide In a manner analogous to that described in Example 7 from 0.13 g of 2(R)-[1(S)-(benzyloxycarbamoyl)-4-phenylbutyl]-4-methyl-N-(8-methyl-2,4-dioxo-1,3,8-triazaspiro[4.5]decan-3-yl)valeramide there was obtained 0.086 g of 2(R)-[1(S)-(hydroxycarbamoyl)-4-phenylbutyl]-4-methyl-N-(8-methyl-2,4-dioxo-1,3,8-triazaspiro[4.5]decan-3-yl)valeramide in the form of a white solid.

MS: 488 (M+H)+.

HPLC: Gradient elution using solvent A containing 5% solvent B increasing to 95% solvent B over 15 minutes; flow rate 1 ml/minute. Retention time: 7.53 minutes. Solvent A: $H_2O/0.1\%$ TFA; solvent B: $CH_3CN/0.085\%$ TFA. Column type: HYPERPEP 300A.

The 2(R)-[1(S)-(benzyloxycarbamoyl)-4-phenylbutyl]-4-methyl-N-(8-methyl-2,4-dioxo-1,3,8-triazaspiro[4.5]decan-3-yl)valeramide used as the starting material was prepared as follows:

(i) A mixture of 0.403 g of 2(R)-[1(S)-(tert-butoxycarbonyl)-4-phenylbutyl]-4-methyl-N-[2,4-dioxo-1,3,8-triazaspiro[4.5]decan-3-yl]valeramide, 0.145 ml of 38% aqueous formaldehyde solution and 0.093 g of 10% palladium-on-charcoal catalyst in 4 ml of methanol was shaken in a hydrogen atmosphere for 2 days. The catalyst was filtered off and the methanol evaporated. The residue was re-evaporated from toluene and the solid obtained triturated with diethyl ether. There was obtained 0.348 g of 2(R)-[1(S)-(tert-butoxycarbonyl)-4-phenylbutyl]-4-methyl-N-(8-methyl-2,4-dioxo-1,3,8-triazaspiro[4.5]decan-3-yl)valeramide in the form of a white solid.

MS: 529 (M+H)+.

(ii) In a manner analogous to that described in Example 1, parts (vii) and (viii) but using O-benzylhydroxylamine in place of O-(tetrahydro-2H-pyran-2(RS)-yl)hydroxylamine there was obtained 2R-[1(S)-(benzyloxycarbamoyl)-4-phenylbutyl]-4-methyl-N-(8-methyl-2,4-dioxo-1,3,8-triazaspiro[4.5]decan-3-yl)valeramide in the form of a white solid.

MS: 578 (M+H)+.

EXAMPLE 60

2(R)-[2-(4-Biphenylyl)-1(S)-(hydroxycarbamoyl)ethyl]-N-(2,5-dioxo-1-imidazolidinyl)-4-methylvaleramide In a manner analogous to that described in Example 3 from 0.097 g of 2(R)-[2-(4-biphenylyl)-1(S)-[(tetrahydro-2(RS)-pyranyloxy)carbamoyl]ethyl]-N-(2,5-dioxo-1-imidazolidinyl)-4-methylvaleramide there was obtained 0.067 g of 2(R)-[2-(4-biphenylyl)-1(S)-(hydroxycarbamoyl)ethyl]-N-(2,5-dioxo-1-imidazolidinyl)-4-methylvaleramide in the form of an off-white solid.

MS: 453 (M+H)+.

HPLC: Gradient elution using solvent A containing 5% solvent B increasing to 95% solvent B over 15 minutes; flow rate 1 ml/minute. Retention time: 9.06 minutes. Solvent A: $H_2O/0.1\%$ TFA; solvent B: $CH_3CN/0.085\%$ TFA. Column type: HYPERPEP 300A.

The 2(R)-[2-(4-biphenylyl)-1(S)-[(tetrahydro-2(RS)-pyranyloxy)carbamoyl]ethyl]-N-(2,5-dioxo-1-imidazolidinyl)-4-methylvaleramide used as the starting material was prepared as follows:

(i) In a manner analogous to that described in Example 7, part (i) starting from 2(R)-[2-(4-biphenylyl)-1(S)-(tert-butoxycarbonyl)ethyl]-4-methylvaleric acid (prepared according to the method in Broadhurst et. al. Eur.Pat.Appl. EP 497192 A2 920805. CAN 118:169601) there was obtained 2(R)-[2-(4-biphenylyl)-1(S)-(tert-butoxycarbonyl)ethyl]-4-methylvalerohydrazide in the form of a white solid.

MS: 411 (M+H)+.

(ii) In a manner analogous to that described in Example 7 part (ii) and Example 1 parts (vii) and (viii) starting from 2(R)-[2-(4-biphenylyl)-1(S)-(tert-butoxycarbonyl)ethyl]-4-methylvalerohydrazide and ethyl isocyanatoacetate there was obtained 2(R)-[2-(4-biphenylyl)-1(S)-[(tetrahydro-2(RS)-pyranyloxy)carbamoyl]ethyl]-N-(2,5-dioxo-1-imidazolidinyl)-4-methylvaleramide in the form of a white solid.

MS: 537 (M+H)+.

EXAMPLE 61

2(R)-[2-(2-Biphenylyl)-1(S)-(hydroxycarbamoyl)ethyl]-N-(2,5-dioxo-1-imidazolidinyl)-4-methylvaleramide In a manner analogous to that described in Example 3 from 0.04 g of 2(R)-[2-(2-biphenylyl)-1(S)-[(tetrahydro-2(RS)-pyranyloxy)carbamoyl]ethyl]-N-(2,5-dioxo-1-imidazolidinyl)-4-methylvaleramide there was obtained 0.021 g of 2(R)-[2-(2-biphenylyl)-1(S)-(hydroxycarbamoyl)ethyl]-N-(2,5-dioxo-1-imidazolidinyl)-4-methylvaleramide in the form of an off white solid.

MS: 453 (M+H)+.

HPLC: Gradient elution using solvent A containing 5% solvent B increasing to 95% solvent B over 15 minutes; flow rate 1 ml/minute. Retention time: 8.49 minutes. Solvent A: $H_2O/0.1\%$ TFA; solvent B: $CH_3CN/0.085\%$ TFA. Column type: HYPERPEP 300A.

The 2(R)-[2-(2-biphenylyl)-1(S)-[(tetrahydro-2(RS)-pyranyloxy)carbamoyl]ethyl]-N-(2,5-dioxo-1-imidazolidinyl)-4-methylvaleramide used as the starting material was prepared as follows:

(i) In a manner analogous to that described in Example 7, part (i) starting from 2(R)-[2-(2-biphenylyl)-1(S)-tert-butoxycarbonyl)ethyl-4-methylvaleric acid (prepared in a manner analogous to the method in Broadhurst et. al. Eur.Pat.Appl. EP 497192 A2 920805. CAN 118:169601) there was obtained 2(R)-[2-(2-biphenylyl)-1(S)-tert-butoxycarbonyl)ethyl]-4-methylvalerohydrazide in the form of a white solid.

MS: 411 (M+H)+.

(ii) In a manner analogous to that described in Example 7 part (ii) and Example 1 parts (vii) and (viii) starting from 2(R)-[2-(2-biphenylyl)-1(S)-(tert-butoxycarbonyl)ethyl]-4-methylvalerohydrazide and ethyl isocyanatoacetate there was obtained 2(R)-[2-(2-biphenylyl)-1(S)-[(tetrahydro-2 (RS)-pyranyloxy)carbamoyl]ethyl-N-(2,5-dioxo-1-imidazolidinyl)-4-methylvaleramide in the form of a white solid.

MS: 537 (M+H)$^+$.

EXAMPLE 62

2(R)-[1(S)-(Hydroxycarbamoyl)-4-phenylbutyl]-N-[4(RS)-(1(R)-hydroxyethyl)-2,5-dioxo-1-imidazolidinyl]-4-methylvaleramide In a manner analogous to that described in Example 3 from 0.729 g of 2(R)-[1(S)-[(tetrahydro-2(RS)-pyranyloxy) carbamoyl]-4-phenylbutyl]-N-[4(RS)-(1(R)-hydroxyethyl)-2,5-dioxo-1-imidazolidinyl]-4-methylvaleramide there was obtained 0.282 g of 2(R)-[1(S)-(hydroxycarbamoyl)-4-phenylbutyl]-N-[4(RS)-(1(R)-hydroxyethyl)-2,5-dioxo-1-imidazolidinyl]-4-methylvaleramide in the form of a white solid.

MS: 449 (M+H)$^+$.

HPLC: Gradient elution using solvent A containing 5% solvent B increasing to 95% solvent B over 15 minutes; flow rate 1 ml/minute. Retention time: 7.78 and 7.82 minutes. Solvent A: H$_2$O/0.1% TFA; solvent B: CH$_3$CN/0.085% TFA. Column type: HYPERPEP 300A.

The 2(R)-[1(S)-[(tetrahydro-2(RS)-pyranyloxy) carbonyl]-4-phenyl]-N-[4(RS)-(1(R)-hydroxyethyl)-2,5-dioxo-1-imidazolidinyl]-4-methylvaleramide used as the starting material was prepared in a manner analogous to that described in Example 7, part (ii) and Example 1, parts (vii) and (viii), starting from 2(R)-[1(S)-(tert-butoxycarbonyl)-4-phenylbutyl]-4-methylvalerohydrazide and methyl(RS)-2-isocyanato-3(R)-tert-butoxybutyrate.

MS: 533 (M+H)$^+$.

EXAMPLE 63

N-(1,2,3,5,6,7,8,8a(RS)-Octahydro-1,3-dioxoimidazo[1,5-a]pyrazin-2-yl)-2(R)-[1(S)-(hydroxycarbamoyl)-4-phenylbutyl]-4-methylvaleramide A solution of 0.160 g of (E)-N-(1,2,3,5,6,7,8,8a(RS)-octahydro-1,3-dioxoimidazo[1,5-a]pyrazin-2-yl)-2(R)-[1 (S)-(benzyloxycarbamoyl)-4-phenyl-3-butenyl]-4-methylvaleramide in 10 ml of methanol was hydrogenated for 3 hours in the presence of 0.02 g of 10% palladium-on-carbon. The catalyst was removed by filtration and evaporation of the solvent gave 0.120 g of N-(1,2,3,5,6,7,8,8a (RS)-octahydro-1,3-dioxoimidazo[1,5-a]pyrazin-2-yl)-2 (R)-[1(S)-(hydroxycarbamoyl)-4-phenylbutyl]-4-methylvaleramide in the form of a white solid.

MS: 460 (M+H)$^+$.

HPLC: Gradient elution using solvent A containing 5% solvent B increasing to 95% solvent B over 15 minutes; flow rate 1 ml/minute. Retention time: 7.93 minutes. Solvent A: H$_2$O/0.1% TFA; solvent B: CH$_3$CN/0.085% TFA. Column type: HYPERSIL C19 BDS.

The (E)-N-(1,2,3,5,6,7,8,8a(RS)-octahydro-1,3-dioxoimidazo[1,5-a]pyrazin-2-yl)-2(R)-[1(S)-(benzyloxycarbamoyl)-4-phenyl-3-butenyl]-4-methylvaleramide used as the starting material was prepared as follows:

(i) A solution of 0.733 g of (E)-2(S)-(tert-butoxycarbonyl)-1(R)-isobutyl-5-phenylpent-4-enyl-1,3,4-oxadiazol-2(3H)-one (prepared as described in Example 34, part (i)) and 0.467 g of 1-(1,1-dimethylethyl)-3-methyl ester 1,3-piperazine-dicarboxylic acid in 15 ml of toluene was treated with 0.53 ml of triethylamine and then heated overnight at reflux temperature. The solvent was evaporated and the residue dissolved in ethyl acetate and then washed in sequence with 5% aqueous citric acid, 5% aqueous sodium hydrogen carbonate, and brine. The organic layer was dried over anhydrous magnesium solvent and then evaporated. The residue was purified by flash column chromatography on silica gel, using ethyl acetate/hexane (1:3) for the elution, to give 0.618 g of (E)-N-(1,2,3,5,6,7,8,8a (RS)-7-(tert-butoxycarbonyl)-octahydro-1,3-dioxoimidazo [1,5-a]pyrazin-2-yl)-2(R)-[1(S)-(tert-butoxycarbonyl)-4-phenyl-3-butenyl]-4-methylvaleramide in the form of a white solid.

MS: 621 (M+Na)$^+$.

(ii) A solution of 0.618 g of (E)-N-(1,2,3,5,6,7,8,8a(RS)-7-(tert-butoxycarbonyl)-octahydro-1,3-dioxoimidazo[1,5-a] pyrazin-2-yl)-2(R)-[1(S)-(tert-butoxycarbonyl)-4-phenyl-3-butenyl]-4-methylvaleramide in 5 ml of dichloromethane was treated with 5 ml of trifluoroacetic acid and stirred under a nitrogen atmosphere for 1 hour. Evaporation gave 0.776 g of (E)-N-(1,2,3,5,6,7,8,8a(RS)-octahydro-1,3-dioxoimidazo [1,5-a]pyrazin-2-yl)-2(R)-[1(S)-(carboxy)-4-phenyl-3-butenyl]-4-methylvaleramide in the form of a white foam.

MS: 443 (M+H)$^+$.

(iii) A solution of 0.415 g of (E)-N-(1,2,3,5,6,7,8,8a(RS)-octahydro-1,3-dioxoimidazo[1,5-a]pyrazin-2-yl)-2(R)-[1 (S)-(carboxy)-4-phenyl-3-butenyl]-4-methylvaleramide in 0.25 ml of dimethylformamide was treated with 0.461 g of O-benzylhydroxylamine and 0.173 g of 1-ethyl-3-(3-dimethylaminopropyl)-carbodiimide hydrochloride and stirred at room temperature for 4 hours. Evaporation gave a residue which was dissolved in ethyl acetate and washed with 5% aqueous sodium hydrogen carbonate and saturated aqueous sodium chloride. Drying over anhydrous magnesium sulphate and evaporation gave a residue which was triturated with diethyl ether to give 0.160 g of (E)-N-(1,2, 3,5,6,7,8,8a(RS)-octahydro-1,3-dioxoimidazo[1,5-a] pyrazin-2-yl)-2(R)-[1(S)-(benzyloxycarbamoyl)-4-phenyl-3-butenyl]-4-methylvaleramide in the form of a white solid.

MS: 548 (M+H)$^+$.

EXAMPLE 64

N-(1,2,3,5,6,7,8,8a(RS)-Octahydro-7-methyl-1,3-dioxoimidazo[1,5-a]pyrazin-2-yl)-2(R)-[1(S)-(hydroxycarbamoyl)-4-phenylbutyl]-4-methylvaleramide A solution of 0.160 g of (E)-N-(1,2,3,5,6,7,8,8a(RS)-octahydro-7-methyl-1,3-dioxoimidazo[1,5-a]pyrazin-2-yl)-2(R)-[1(S)-(benzyloxycarbamoyl)-4-phenylbutyl]-4-methylvaleramide in 10 ml of methanol was hydrogenated for 4 hours in the presence of 0.02 g of 10% palladium-on-carbon. The catalyst was removed by filtration and evaporation of the solvent gave 0.115 g of N-(1,2,3,5,6,7,8,8a (RS)-octahydro-7 -methyl-1,3-dioxoimidazo[1,5-a]pyrazin-2-yl)-2(R)-[1(S)-(hydroxycarbamoyl)-4-phenylbutyl]-4-methylvaleramide in the form of a white solid.

MS: 474 (M+H)$^+$.

HPLC: Gradient elution using solvent A containing 5% solvent B increasing to 95% solvent B over 15 minutes; flow rate 1 ml/minute. Retention time: 8.06 minutes. Solvent A: H$_2$O/0.1% TFA; solvent B: CH$_3$CN/0.085% TFA. Column type: HYPERSIL C19 BDS.

The (E)-N-(1,2,3,5,6,7,8,8a(RS)-Octahydro-7-methyl-1, 3-dioxoimidazo[1,5-a]pyrazin-2-yl)-2(R)-[1(S)-(benzyloxycarbamoyl)-4-phenylbutyl]-4-methylvaleramide used as the starting material was prepared as follows:

(i) A solution of 0.361 g of (E)-N-(1,2,3,5,6,7,8,8a(RS)-octahydro-1,3-dioxoimidazo[1,5-a]pyrazin-2-yl)-2(R)-[1(S)-(carboxy)-4-phenyl-3-butenyl]-4-methylvaleramide (prepared as described in Example 63) in 10 ml of methanol was treated with 1 ml of 40% aqueous formaldehyde solution and then hydrogenated for 1 hour in the presence of 0.03 g of 10% palladium-on-carbon. The catalyst was removed by filtration and evaporation gave 0.395 g of (E)-N-(1,2,3, 5,6,7,8,8a(RS)-octahydro-7-methyl-1,3-dioxoimidazo[1,5-a]pyrazin-2-yl)-2(R)-[1(S)-(carboxy)-4-phenyl-3-butenyl]-4-methylvaleramide in the form of a clear oil.

MS: 459 (M+Na)$^+$.

(ii) A solution of 0.395 g of (E)-N-(1,2,3,5,6,7,8,8a(RS)-octahydro-7-methyl-1,3-dioxoimidazo[1,5-a]pyrazin-2-yl)-2(R)-[1(S)-(carboxy)-4-phenyl-3-butenyl]-4-methylvaleramide in 0.25 ml of dimethylformamide was treated with 0.400 g of O-benzylhydroxylamine and 0.150 g of 1-ethyl-3-(3-dimethylaminopropyl)-carbodiimide hydrochloride and stirred at room temperature overnight. Evaporation gave a residue which was dissolved in ethyl acetate and washed with 5% aqueous sodium hydrogen carbonate and saturated aqueous sodium chloride. Drying over anhydrous magnesium sulphate and evaporation gave a residue which was triturated with diethyl ether to give 0.165 g of (E)-N-(1,2,3,5,6,7,8,8a(RS)-octahydro-7-methyl-1,3-dioxoimidazo[1,5-a]pyrazin-2-yl)-2(R)-[1(S)-(benzyloxycarbamoyl)-4-phenylbutyl]-4-methylvaleramide in the form of a white solid.

MS: 564 (M+H)$^+$.

What is claimed is:

1. A hydrazine derivative, being a compound of the formula

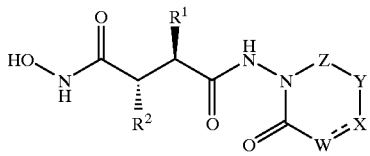
(I)

wherein the ring incorporating W, X, Y, and Z is selected from the group consisting of rings of formulae (a), (b), (c), (d), (e), (f), (g), (h), (i), (u),

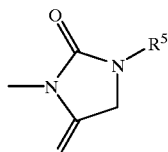
(a)

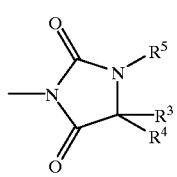
(b)

-continued

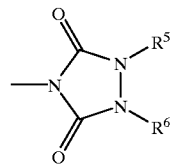
(c)

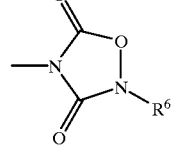
(d)

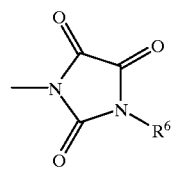
(e)

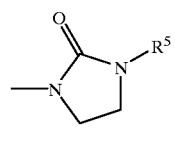
(f)

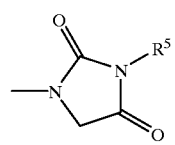
(g)

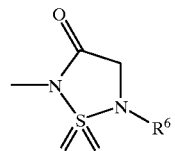
(h)

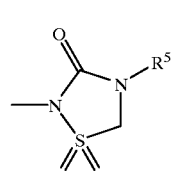
(i)

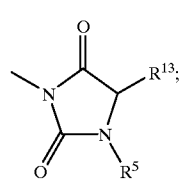
(u)

and $R^1$ is unsubstituted lower alkyl, unsubstituted lower alkenyl, unsubstituted lower cycloalkyl, unsubstituted lower cycloalkyl-lower alkyl, unsubstituted or substituted phenyl or naphthyl, or phenyl- or naphthyl-lower alkyl in which the phenyl or naphthyl is unsubstituted or substituted and the lower alkyl is unsubstituted;

$R^2$ is unsubstituted lower alkyl, unsubstituted lower alkenyl, unsubstituted lower cycloalkyl, unsubstituted lower cycloalkyl-lower alkyl, —V-phenyl or -naphthyl in which the phenyl or naphthyl is unsubstituted or substituted, —V-heterocyclyl in which the heterocyclyl is unsubstituted or substituted, or —$(CH_2)_q$—CH=$CR^8R^9$;

$R^3$, $R^4$, $R^5$, $R^6$ and $R^7$ are each independently hydrogen, unsubstituted or substituted lower alkyl, lower alkenyl, lower cycloalkyl, lower cycloalkyl-lower alkyl in which the lower alkyl is unsubstituted and the cycloalkyl is unsubstituted, unsubstituted or substituted phenyl or naphthyl, phenyl- or naphthyl-lower alkyl in which the phenyl or naphthyl is unsubstituted or substituted and the lower alkyl is unsubstituted, unsubstituted or substituted heterocyclyl or heterocyclyl-lower alkyl in which the heterocyclyl is unsubstituted or substituted and the lower alkyl is unsubstituted; except that $R^3$ and $R^4$ cannot both be hydrogen, or $R^3$ and $R^4$ together with the carbon atom to which they are attached form a saturated carbocyclic ring having from 3 to 8 ring atoms in which zero or one ring atom is a heteroatom selected from the groups consisting of N, O and S wherein the ring nitrogen is unsubstituted or substituted; or $R^5$ and $R^6$ or $R^5$ and $R^7$ together with the nitrogen atoms to which they are attached form a saturated carbocyclic ring having from 3 to 8 ring atoms; or $R^{11}$ and $R^{12}$ together with the sp² carbon atoms to which they are attached form a fused unsubstituted lower cycloalkenyl, unsubstituted or substituted phenyl or naphthyl or unsubstituted or substituted heteroaryl; or $R^5$ with either $R^{13}$ or $R^{14}$ together are lower alkylene in which zero or one $CH_2$ of the lower alkylene is replaced by a heteroatom selected from the group consisting of N, O and S wherein the N is unsubstituted or substituted; or either $R^6$ or $R^7$ with either $R^3$ or $R^4$ together are lower alkylene in which zero or one $CH_2$ of the lower alkylene is replaced by a heteroatom selected from the group consisting of N, O and S wherein the N is unsubstituted or substituted;

V is —$(CH_2)_r$—U—$(CH_2)_s$— in which r and s are each independently 0, 1, 2 or 3 and wherein U is absent or is —CH=CH—, —C≡C—, —S—, —O—, —NH—, NHCO—, —CONH—, —$SO_2$—, —$NHSO_2$—, —$SO_2NH$—, —NHCONH— or —$NHSO_2NH$—;

$R^8$ and $R^9$ together are lower alkylene in which zero or one $CH_2$ of the lower alkylene is replaced by a heteroatom selected from the group consisting of N,O and S wherein the N is unsubstituted or substituted; and q is 1 or 2;

or a mixture containing the compound and one or more optical isomers thereof, or a pharmaceutically acceptable salt of said compound or said mixture.

2. A compound of claim 1 wherein the ring incorporating W, X, Y, and Z is selected from the group consisting of rings of formulae (a), (b), (c), (e), (f), (g), (h), (r), and (u).

3. The hydrazine derivative according to claim 1, wherein the ring incorporating W, X, Y and Z is selected from the group consisting of rings of formulae (a) to (i) in which $R^3$, $R^4$, $R^5$, $R^6$ and $R^7$ have the significance given earlier except that if $R^3$ or $R^4$ is hydrogen the other is not hydrogen:

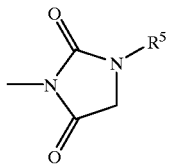
(a)

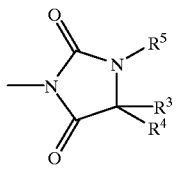
(b)

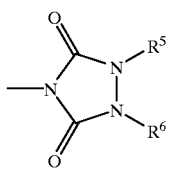
(c)

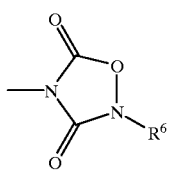
(d)

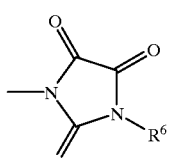
(e)

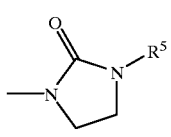
(f)

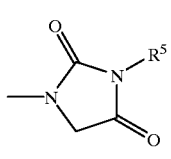
(g)

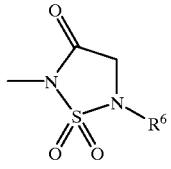
(h)

-continued (i)

4. The hydrazine derivative according to claim 1, wherein the ring incorporating W, X, Y and Z is selected from the group consisting of rings of formulae (a), (b), (r), and (u).

5. The hydrazine derivative according to claim 4, wherein the ring incorporating W, X, Y and Z is selected from the group consisting of rings of formulae (a).

6. The hydrazine derivative according to claim 1, wherein $R^1$ is lower alkyl.

7. The hydrazine derivative according to claim 6, wherein $R^1$ is isopropyl.

8. The hydrazine derivative according to claim 1, wherein $R^2$ is lower cycloalkyl-lower alkyl.

9. The hydrazine derivative according to claim 8, wherein $R^2$ is 3-cyclohexylpropyl.

10. The hydrazine derivative according to claim 1, wherein $R^2$ is —$(CH_2)_3$-aryl or —$CH_2$—CH=CH-aryl, in which each aryl is unsubstituted or substituted.

11. The hydrazine derivative according to claim 10, wherein aryl is unsubstituted phenyl.

12. The hydrazine derivative according to claim 1, wherein $R^2$ is phenylbenzyl.

13. The compound according to claim 1, selected from:
(E)-2(R)-[1(S)-(Hydroxycarbamoyl)-4-phenyl-3-butenyl]-4-methyl-N-(2,5-dioxo-1-imidazolidinyl)valeramide;
(E)-N-(hexahydro-2,6-dioxo-1-pyrimidinyl)-2(R)-[1(S)-(hydroxycarbamoyl)-4-phenyl-3-butenyl]-4-methylvaleramide;
2(R)-[4-cyclohexyl-1(S)-(hydroxycarbamoyl)butyl]-4-methyl-N-(2,5-dioxo-1-imidazolidinyl)valeramide;
(E)-N-(tetrahydro-3-oxo-2H-1,2,4-thiadiazin-2-yl)-2(R)-[1(S)-(hydroxycarbamoyl)-4-phenyl-3-butenyl]-4-methylvaleramide S,S-dioxide;
2(R)-[1(S)-(hydroxycarbamoyl)-4-phenylbutyl]-4-methyl-N-(2,6-dioxo-1-piperazinyl)valeramide;
2(R)-[1(S)-(Hydroxycarbamoyl)-4-phenylbutyl]-N-(4(S)-isopropyl-2,5-dioxo-1-imidazolidinyl)-4-methylvaleramide;
2(R)-[1(S)-(Hydroxycarbamoyl)-4-phenylbutyl]-4-methyl-N-[4(S)-(1(S)-methylpropyl)-2,5-dioxo-1-imidazolidinylvaleramide;
(E)-2(R)-[1(S)-(Hydroxycarbamoyl)-4-phenyl-3-butenyl]-N-[4(S)-(1(S)-methylpropyl)-2,5-dioxo-1-imidazolidinyl]-4-methylvaleramide;
2(R)-[1(S)-(Hydroxycarbamoyl)-4-phenylbutyl]-4-methyl-N-(2,5-dioxo-1-imidazolidinyl)valeramide; and
2(R)-[2-(4-Biphenylyl)-1(S)-(hydroxycarbamoyl)ethyl]-N-(2,5-dioxo-1-imidazolidinyl)-4-methylvaleramide.

14. The compound according to claim 1, selected from:
2(R)-[1(S)-(Hydroxycarbamoyl)-4-phenylbutyl]-4-methyl-N-[4(S)-[2-(methylthio)ethyl]-2,5-dioxo-1-imidazolidinyl]valeramide;
2(R)-[1(S)-(Hydroxycarbamoyl)-4-phenylbutyl]-N-[4(S)-(hydroxymethyl)-2,5-dioxo-1-imidazolidinyl]-4-methylvaleramide;
2(R)-[1(S)-(Hydroxycarbamoyl)-4-phenylbutyl]-N-(4(S)-isopropyl-5-oxo-2-thioxo-1-imidazolidinyl)-4-methylvaleramide;
(E)-2(R)-[1(S)-(Hydroxycarbamoyl)-4-phenyl-3-butenyl]-N-[4(S)-(hydroxymethyl)-2,5-dioxo-1-imidazolidinyl]-4-methylvaleramide;
Benzyl3-[2(R)-[1(S)-(hydroxycarbamoyl)-4-phenylbutyl]-4-methylvaleramido]-2, 4-dioxo-1,3,8-triazaspiro[4,5]decane-8-carboxylate;
N-(1,2,3,4-Tetrahydro-2,4-dioxothieno[3,2-d]pyrimidin-3-yl)-2(R)-[1(S)-(hydroxycarbamoyl)-4-phenylbutyl]-4-methylvaleramide;
N-(1,2,3,4-Tetrahydro-2,4-dioxothieno[3,4-d]pyrimidin-3-yl)-2(R)-[1(S)-(hydroxycarbamoyl)-4-phenylbutyl]-4-methylvaleramide;
2(R)-[1(S)-(Hydroxycarbamoyl)-4-phenylbutyl]-N-[4(S)-methoxymethyl)-2,5-dioxo-1-imidazolidinyl]-4-methylvaleramide; and
1-(8-Acetyl-2,4-dioxo-1,3,8-triazaspiro[4.5]decan-3-yl)-2(R)-[1(S)-(hydroxycarbamoyl)-4-phenylbutyl]-4-methylvaleramide.

15. A process for manufacturing the hydrazine derivative of claim 1, which process comprises cleaving off the protecting group $R^{10}$ from the corresponding precursor wherein the precursor is a compound of the formula (II)

wherein $R^1$, $R^2$, W, X, Y and Z have the significance given in claim 1 and $R^{10}$ is a protecting group;

or a mixture containing the compound of formula II and one or more optical isomers thereof.

16. The process of claim 15, further comprising converting the hydrazine derivative produced in claim 15 to a pharmaceutically acceptable salt thereof.

* * * * *

UNITED STATES PATENT AND TRADEMARK OFFICE
CERTIFICATE OF CORRECTION

PATENT NO. : 6,281,363 B1  
DATED : August 28, 2001  
INVENTOR(S) : Michael Broadhurst, William Henry Johnson and Daryl Simon Walter Page 1 of 2

It is certified that error appears in the above-identified patent and that said Letters Patent is hereby corrected as shown below:

Column 79, claim 1,  
Line 50, after "(i)" insert -- (r) --  
Lines 60-65, replace

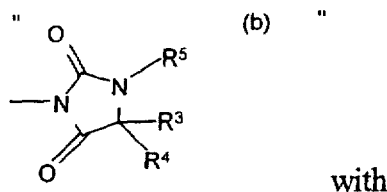

with

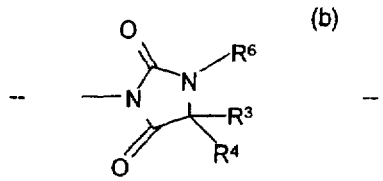

Column 80, claim 1,  
Line 53, insert

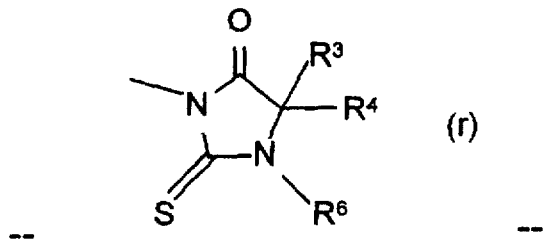

Column 81, claim 1,  
Line 11, replace ", $R^6$ and $R^7$" with -- $R^6$ --  
Line 30, delete "or $R^5$ and $R^7$"  
Lines 33-37, delete "or $R^{11}$ and $R^{12}$ together with the $sp^2$ carbon atoms to which they are attached form a fused unsubstituted lower cycloalkenyl, unsubstituted or substituted phenyl or naphthyl or unsubstituted or substituted heteroaryl;"

UNITED STATES PATENT AND TRADEMARK OFFICE
CERTIFICATE OF CORRECTION

PATENT NO.   : 6,281,363 B1
DATED        : August 28, 2001
INVENTOR(S)  : Michael Broadhurst, William Henry Johnson and Daryl Simon Walter It is certified that error appears in the above-identified patent and that said Letters Patent is hereby corrected as shown below:

Column 81, claim 3,
Line 2, replace ", $R^6$ and $R^7$" with -- $R^6$ --
Lines 14-20, replace

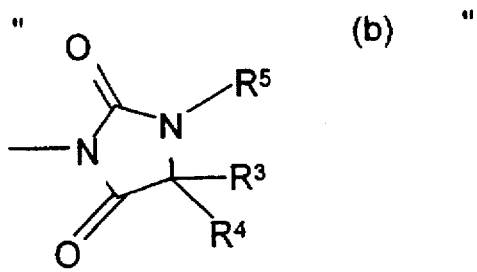
(b)

Signed and Sealed this

Sixteenth Day of April, 2002

Attest:

JAMES E. ROGAN
Attesting Officer   Director of the United States Patent and Trademark Office